(12) United States Patent
Fafard et al.

(10) Patent No.: US 9,969,756 B2
(45) Date of Patent: May 15, 2018

(54) CARBOSILANE SUBSTITUTED AMINE PRECURSORS FOR DEPOSITION OF SI-CONTAINING FILMS AND METHODS THEREOF

(71) Applicants: American Air Liquide, Inc., Fremont, CA (US); L'Air Liquide, Société Anonyme pour l'Etude et l'Exploitation des Procédés Georges Claude, Paris (FR)

(72) Inventors: Claudia Fafard, Newark, DE (US); Venkateswara R. Pallem, Hockessin, DE (US); Jean-Marc Girard, Versailles (FR)

(73) Assignees: L'Air Liquide, Société Anonyme pour l'Etude et l'Exploitation des Procédés George Claude, Paris (FR); American Air Liquide, Inc., Fremont, CA (US)

(*) Notice: Subject to any disclaimer, the term of this patent is extended or adjusted under 35 U.S.C. 154(b) by 0 days. days.

(21) Appl. No.: 15/512,968

(22) PCT Filed: Sep. 23, 2015

(86) PCT No.: PCT/US2015/051678
§ 371 (c)(1),
(2) Date: Mar. 21, 2017

(87) PCT Pub. No.: WO2016/049154
PCT Pub. Date: Mar. 31, 2016

(65) Prior Publication Data
US 2017/0291915 A1   Oct. 12, 2017

Related U.S. Application Data

(60) Provisional application No. 62/054,198, filed on Sep. 23, 2014.

(51) Int. Cl.
*H01L 21/02* (2006.01)
*C07F 7/10* (2006.01)
(Continued)

(52) U.S. Cl.
CPC .......... *C07F 7/10* (2013.01); *C07F 7/08* (2013.01); *C23C 16/24* (2013.01);
(Continued)

(58) Field of Classification Search
CPC ......... H01L 21/02118; H01L 21/02123; H01L 21/0228; H01L 21/02532
See application file for complete search history.

(56) References Cited

U.S. PATENT DOCUMENTS 4,833,107 A   5/1989  Kaya et al.
6,489,030 B1  12/2002 Wu et al.
(Continued)

FOREIGN PATENT DOCUMENTS

CN   103881101   6/2014
EP   1 640 404   3/2006
(Continued)

OTHER PUBLICATIONS

Aylett, B.J. et al., "The preparation and some properties of disilylamine," Inorg. Chem. 1966 5(1) 167.
(Continued)

*Primary Examiner* — Jaehwan Oh
(74) *Attorney, Agent, or Firm* — Patricia E. McQueeney

(57) ABSTRACT

Disclosed are Si-containing film forming compositions comprising carbosilane substituted amine precursors. The carbosilane substituted amine precursors have the formula $(R^1)_aN(-SiHR^2-CH_2-SiH_2R^3)_{3-a}$, wherein a=0 or 1; $R^1$ is H, a C1 to C6 alkyl group, or a halogen; $R^2$ and $R^3$ is each independently H; a halogen; an alkoxy group having the formula OR', wherein R' is an alkyl group (C1 to C6); or an alkylamino group having the formula $NR''_2$, wherein each R" is independently H, a C1-C6 alkyl group, a C1-C6 alkenyl group, or a C3-C10 aryl or heterocycle group. Also disclosed are methods of synthesizing the carbosilane sub-
(Continued)

stituted amine precursors and their use for deposition processes.

20 Claims, 1 Drawing Sheet

(51) Int. Cl.
    C07F 7/08    (2006.01)
    C23C 16/24    (2006.01)
    C23C 16/455    (2006.01)

(52) U.S. Cl.
    CPC .... *C23C 16/45553* (2013.01); *H01L 21/0228* (2013.01); *H01L 21/02123* (2013.01); *H01L 21/02532* (2013.01)

(56) References Cited

U.S. PATENT DOCUMENTS

| | | |
|---|---|---|
| 6,940,173 B2 | 9/2005 | Cohen et al. |
| 8,497,391 B2 | 7/2013 | Ohno et al. |
| 2003/0017635 A1 | 1/2003 | Apen et al. |
| 2006/0012014 A1 | 1/2006 | Chen et al. |
| 2008/0124815 A1 | 5/2008 | Malone et al. |
| 2009/0061199 A1 | 3/2009 | Egami et al. |
| 2010/0034789 A1* | 2/2010 | De La Mata De La Mata ............... A61K 47/48192 424/93.21 |
| 2010/0252917 A1* | 10/2010 | Karkkainen ........... C08G 77/52 257/629 |
| 2014/0030448 A1 | 1/2014 | Bowen et al. |
| 2014/0158580 A1 | 6/2014 | Xiao et al. |
| 2015/0147484 A1* | 5/2015 | Nguyen .................. C23C 16/36 427/535 |
| 2015/0246937 A1 | 9/2015 | Xiao et al. |

FOREIGN PATENT DOCUMENTS

| | | |
|---|---|---|
| EP | 2 048 700 | 4/2009 |
| EP | 2 818 474 | 12/2014 |
| JP | 4196246 | 12/2008 |
| KR | 2014 0087908 | 7/2014 |
| WO | WO 2004 030071 | 4/2004 |
| WO | WO 2005 093126 | 10/2005 |

OTHER PUBLICATIONS

Blandez, J.F. et al., "Palladium nanoparticles supported on graphene as catalysts for the dehydrogenative coupling of hydrosilanes and amines," Catal. Sci. Technol. 2015 (5) 1969, 2167-2173.

Elsässer, R. et al., "Nematic dendrimers based on carbosilazane cores" Angewandte Chemie Int. Ed., vol. 40, issue 14, Jul. 16, 2001, 2688-2690.

Guruvenket, S. et al., "Atmospheric-pressure plasma-enhanced chemical vapor deposition of a-SiCN—H films: role of precursors on the film growth and properties," ACS Applied Materials and Interfaces 2012, 4, 5293-5299.

Hizawa et al., "Synthesis of alkyl and alkoxy derivatives of hexachlorodisihnethylene and their hydrolysis," The Journal of the Society of Chemical Industry, Japan, vol. 59 (1956) No. 11 p. 1359-1363.

Hvolbaek, B. et al., "Catalytic activity of Au nanoparticles," Nanotoday, Aug. 2007, vol. 2, No. 4, 14-156.

Jansen, M. et al., "Preparation and characterization of the carbosilazanes bis[tris)methylamino)silyl]methane and bis[tris(phenylamino)silyl]methane," Z. Naturforsch. 52 b, 707-710 (1997).

Lin, C. et al., "Size effect of gold nanoparticles in catalytic reduction of p-nitrophenol with NaBH4," Molecules 2013, 18, 12609-12620.

Liu, H.Q. et al., "Dehydrocoupling of ammonia and silanes catalyzed by dimethyltitanocene," Organometallics 1992, 11, 822-827.

Morrison, J.A. et al., "Synthesis and characterization of the (halosilyl)methylsilanes," Journal of Organometallic Chemistry, 91 (1975) 163-168.

Passarelli, V. et al., "Aminolysis of the Si—Cl bond and ligand exchange reaction between silicon amido derivatives and $SiCl_4$: synthetic applications and kinetic investigations," Dalton Transl 2003, 413-419.

Ringleb, F. et al., "Preparation of Pd—MgO model catalysts by deposition of Pd from aqueous precursor solutions onto Ag(001)-supported MgO(001) thin films," Applied Catalysis A: General 474 (2014) 186-193.

Schuh, H. et al., "Disilanyl-amines—compounds comprising the structural unit Si—Si—N, as single-source precursors for plasma-enhanced chemical vapour deposition (PE-CVD) of silicon nitride," Z. Anorg. Allg. Chem. 619 (1993) 1347-1352.

Shatnawi, M. et al., "Formation of Si—C—N ceramics from melamine-carbosilazane single source precursors," Journal of Solid State Chemistry, vol. 181, issue 1, Jan. 2008, 150-157.

Topchiev, A.B. et al., "Synthesis of compounds with silazine links," Doklady Akademii Nauk SSSR, 1956,109, 787-90.

Topchiev, A.B. et al., Issled. v Obl. Kremniiorgan. Soedin., Sintez i Fiz.-Khim. Svoistva, Akad. Nauk SSSR, Inst. Neftekhim. Sinteza, Sb. Statei, 1962, 130-45.

Xie, W. et al., "[(NHC)Yb{N(SiMe$_3$)$_2$}$_2$]-catalyzed cross-dehydrogenative coupling of silanes with amines," Angew. Chem. Int. Ed. 2012 51 11141-11144 and Angew. Chem. 2012 124 11303-11306, DOI: 10.1002/ange.201205317.

International Search Report and Written Opinion for corresponding PCT/US2015/051678, dated Jan. 7, 2016.

International Search Report and Written Opinion for related PCT/US2016/025011, dated Jul. 7, 2016.

* cited by examiner

CARBOSILANE SUBSTITUTED AMINE PRECURSORS FOR DEPOSITION OF SI-CONTAINING FILMS AND METHODS THEREOF

CROSS REFERENCE TO RELATED APPLICATIONS

The present application is a 371 of International PCT Application PCT/US2015/051678 filed Sep. 23, 2015, which claims the benefit of U.S. Provisional Application Ser. No. 62/054,198 filed Sep. 23, 2014, each of which is herein incorporated by reference in its entirety for all purposes.

TECHNICAL FIELD

Disclosed are Si-containing film forming compositions comprising carbosilane substituted amine precursors. The carbosilane substituted amine precursors have the formula $(R^1)_a N(-SiHR^2-CH_2-SiH_2R^3)_{3-a}$, wherein a=0 or 1; $R^1$ is H, a C1 to C6 alkyl group, or a halogen; $R^2$ and $R^3$ is each independently H; a halogen; an alkoxy group having the formula OR', wherein R' is an alkyl group (C1 to C6); or an alkylamino group having the formula $NR''_2$, wherein each R" is independently H, a C1-C6 alkyl group, a C1-C6 alkenyl group, or a C3-C10 aryl or heterocycle group. Also disclosed are methods of synthesizing the carbosilane substituted amine precursors and their use for deposition processes.

BACKGROUND

Si-containing thin films are used widely in the semiconductor, photovoltaic, LCD-TFT, flat panel-type device, refactory material, or aeronautic industries. Si-containing thin films may be used, for example, as dielectric materials having electrical properties which may be insulating ($SiO_2$, SiN, SiC, SiCN, SiCOH, $MSiO_x$, wherein M is Hf, Zr, Ti, Nb, Ta, or Ge and x is 0-4). Si-containing thin films may also be used as conducting films, such as metal silicides or metal silicon nitrides. Due to the strict requirements imposed by downscaling of electrical device architectures towards the nanoscale (especially below 28 nm node), increasingly fine-tuned molecular precursors are required which meet the requirements of volatility (for vapor processes), lower process temperatures, reactivity with various oxidants and low film contamination, in addition to high deposition rates, conformality and consistency of films produced.

Trisilylamine $[N(SiH_3)_3]$ has been used for vapor deposition of silicon nitride and silicon oxynitride films (see, e.g., WO2004/030071 to Dussarrat et al.).

Hizawa and Nojimoto (Kogyo Kagaku Zasshi, 1956, 59, 1359-63) describe the synthesis of $(Me_3SiCH_2SiMe_2)_2NH$ from the reaction of $Me_3SiCH_2SiMe_2Cl$ and $NH_3$.

Topchiev et als. (Doklady Akademii Nauk SSSR, 1956, 109, 787-90 and Issled. v Obl. Kremniiorgan. Soedin., Sintez i Fiz.-Khim. Svoistva, Akad. Nauk SSSR, Inst. Neftekhim. Sinteza, Sb. Statei, 1962, 130-45) disclose the addition of Br at 5-10° C., and finally at 60-80° C. to $R_3SiCH_2SiR_2H$ yielded $R_3SiCH_2SiR_2Br$, where R=Me, Et, Pr, or Bu. These in $Et_2O$ or MePh were treated with $NH_3$, secondary derivatives being prepared in refluxing MePh, yielding the amine derivatives $(R_3SiCH_2SiR_2)_2NH$, and $R_3SiCH_2SiR_2NH_2$. The secondary derivatives are best prepared from the primary amine derivatives and the mono-Br derivatives by refluxing in MePh followed by passage of $NH_3$ 10 hrs.

O'Neill et al. (U.S. Pat. App. Pub. No. 2015/0087139) disclose five classes of organoaminosilane precursors, including $H_3Si-R^3-SiH_2-NR^1-SiH_2-R^3-SiH_3$, wherein $R^1$ is a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, or a $C_5$ to $C_{10}$ aryl group and $R^3$ is a linear or branched $C_1$ to $C_{10}$ alkylene group, a linear or branched $C_3$ to $C_6$ alkynylene group, a $C_3$ to $C_{10}$ cyclic alkylene group, a $C_3$ to $C_{10}$ hetero-cyclic alkylene group, a $C_5$ to $C_{10}$ arylene group, or a $C_5$ to $C_{10}$ hetero arylene group.

Despite the wide range of choices available for the deposition of Si containing films, additional precursors are continuously sought to provide device engineers the ability to tune manufacturing process requirements and achieve films with desirable electrical and physical properties.

Notation and Nomenclature

Certain abbreviations, symbols, and terms are used throughout the following description and claims, and include:

As used herein, the indefinite article "a" or "an" means one or more.

As used herein, the terms "approximately" or "about" mean±10% of the value stated.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x (NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the term "aryl" refers to aromatic ring compounds where one hydrogen atom has been removed from the ring. As used herein, the term "heterocycle" refers to a cyclic compound that has atoms of at least two different elements (not including H), such as C and S and/or N, as members of its ring.

As used herein, the term "carbosilane" refers to a linear or branched molecule with a backbone having alternate Si and C atoms and at least one Si—C—Si unit; the acronym "DSP" stands for disilapropane, and, more particularly $H_3Si-CH_2-SiH_3$ or its ligand analog $H_2Si-CH_2-SiH_3$; the term "carbosilane substituted amine precursor" refers to a $NR_3$ molecule wherein at least one R is, and preferably 2 or 3 Rs are, a carbosilane ligand.

As used herein, the abbreviation "Me" refers to a methyl group; the abbreviation "Et" refers to an ethyl group; the abbreviation "Pr" refers to any propyl group (i.e., n-propyl or isopropyl); the abbreviation "iPr" refers to an isopropyl group; the abbreviation "Bu" refers to any butyl group (n-butyl, iso-butyl, t-butyl, sec-butyl); the abbreviation "tBu" refers to a tert-butyl group; the abbreviation "sBu" refers to a sec-butyl group; the abbreviation "iBu" refers to an iso-butyl group; the abbreviation "Ph" refers to a phenyl group; the abbreviation "Am" refers to any amyl group (iso-amyl, sec-amyl, tert-amyl); the abbreviation "Cy" refers to a cyclic alkyl group (cyclobutyl, cyclopentyl, cyclohexyl, etc.).

As used herein, the acronym "SRO" stands for a Strontium Ruthenium Oxide film; the acronym "HCDS" stands for hexachlorodisilane ($Si_2Cl_6$); and the acronym "PCDS" stands for pentachlorodisilane ($Si_2HCl_5$).

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

SUMMARY

Figure 1:
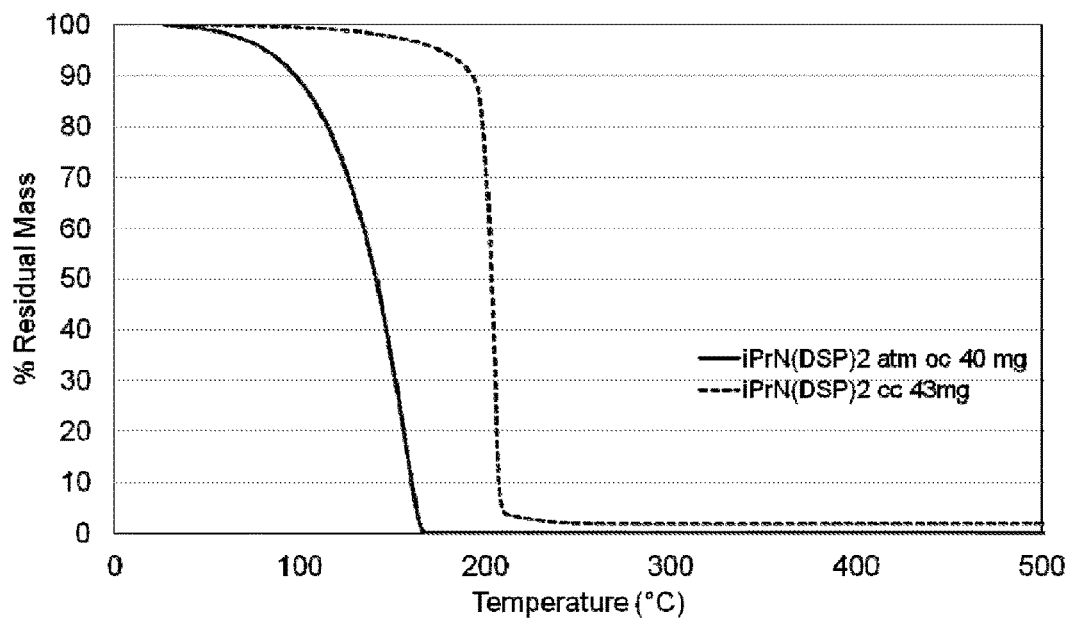
FIG. 1 is a thermogravimetric analysis (TGA) graph demonstrating the percentage of weight loss with temperature change for of iPrN(—$SiH_2$—$CH_2$—$SiH_3$)$_2$.

Disclosed are Si-containing film forming compositions comprising carbosilane substituted amine precursors having the formula ($R^1$)$_a$N(—$SiHR^2$—$CH_2$—$SiH_2R^3$)$_{3-a}$, wherein a=0 or 1; $R^1$ is H, a C1 to C6 alkyl group, or a halogen; $R^2$ and $R^3$ is each independently H, a halogen, an alkoxy group having the formula OR', wherein R' is an alkyl group (C1 to C6), or an alkylamino group having the formula NR''$_2$, wherein each R'' is independently H, a C1-C6 alkyl group, a C1-C6 alkenyl group, or a C3-C10 aryl or heterocycle group. The disclosed precursors may include one or more of the following aspects:
  a=0;
  the formula being N(—$SiHR^2$—$CH_2$—$SiH_2R^3$)$_3$;
  $R^2$=H;
  the formula being N(—$SiH_2$—$CH_2$—$SiH_2R_3$)$_3$;
  the precursor being N($SiH_2$—$CH_2$—$SiH_3$)$_3$;
  the precursor being N($SiH_2$—$CH_2$—$SiH_2$(Cl))$_3$;
  the precursor being N($SiH_2$—$CH_2$—$SiH_2$(Br))$_3$;
  the precursor being N($SiH_2$—$CH_2$—$SiH_2$(I))$_3$;
  the precursor being N($SiH_2$—$CH_2$—$SiH_2$($NH_2$))$_3$;
  the precursor being N($SiH_2$—$CH_2$—$SiH_2$($NMe_2$))$_3$;
  the precursor being N($SiH_2$—$CH_2$—$SiH_2$(NMeEt))$_3$;
  the precursor being N($SiH_2$—$CH_2$—$SiH_2$($NEt_2$))$_3$;
  the precursor being N($SiH_2$—$CH_2$—$SiH_2$($NnPr_2$))$_3$;
  the precursor being N($SiH_2$—$CH_2$—$SiH_2$($NiPr_2$))$_3$;
  the precursor being N($SiH_2$—$CH_2$—$SiH_2$($NBu_2$))$_3$;
  the precursor being N($SiH_2$—$CH_2$—$SiH_2$($NiBu_2$))$_3$;
  the precursor being N($SiH_2$—$CH_2$—$SiH_2$($NtBu_2$))$_3$;
  the precursor being N($SiH_2$—$CH_2$—$SiH_2$($NAm_2$))$_3$;
  the precursor being N($SiH_2$—$CH_2$—$SiH_2$(NCyPentyl$_2$))$_3$;
  the precursor being N($SiH_2$—$CH_2$—$SiH_2$(Nhexyl$_2$))$_3$;
  the precursor being N($SiH_2$—$CH_2$—$SiH_2$(NCyHex$_2$))$_3$;
  the precursor being N($SiH_2$—$CH_2$—$SiH_2$(NMeH))$_3$;
  the precursor being N($SiH_2$—$CH_2$—$SiH_2$(NEtH))$_3$;
  the precursor being N($SiH_2$—$CH_2$—$SiH_2$(NnPrH))$_3$;
  the precursor being N($SiH_2$—$CH_2$—$SiH_2$(NiPrH))$_3$;
  the precursor being N($SiH_2$—$CH_2$—$SiH_2$(NBuH))$_3$;
  the precursor being N($SiH_2$—$CH_2$—$SiH_2$(NiBuH))$_3$;
  the precursor being N($SiH_2$—$CH_2$—$SiH_2$(NtBuH))$_3$;
  the precursor being N($SiH_2$—$CH_2$—$SiH_2$(NAmH))$_3$;
  the precursor being N($SiH_2$—$CH_2$—$SiH_2$(OH))$_3$;
  the precursor being N($SiH_2$—$CH_2$—$SiH_2$(OMe))$_3$;
  the precursor being N($SiH_2$—$CH_2$—$SiH_2$(OEt))$_3$;
  the precursor being N($SiH_2$—$CH_2$—$SiH_2$(OnPr))$_3$;
  the precursor being N($SiH_2$—$CH_2$—$SiH_2$(OiPr))$_3$;
  the precursor being N($SiH_2$—$CH_2$—$SiH_2$(OBu))$_3$;
  the precursor being N($SiH_2$—$CH_2$—$SiH_2$(OiBu))$_3$;
  the precursor being N($SiH_2$—$CH_2$—$SiH_2$(OtBu))$_3$;
  the precursor being N($SiH_2$—$CH_2$—$SiH_2$(OAm))$_3$;
  the precursor being N($SiH_2$—$CH_2$—$SiH_2$(OHexyl))$_3$;
  the precursor being N($SiH_2$—$CH_2$—$SiH_2$(Cl))$_2$($SiH_2$—$CH_2SiH_3$);
  the precursor being N($SiH_2$—$CH_2$—$SiH_2$(Br))$_2$($SiH_2$—$CH_2SiH_3$);
  the precursor being N($SiH_2$—$CH_2$—$SiH_2$(I))$_2$($SiH_2$—$CH_2SiH_3$);
  the precursor being N($SiH_2$—$CH_2$—$SiH_2$($NH_2$))$_2$($SiH_2$—$CH_2SiH_3$);
  the precursor being N($SiH_2$—$CH_2$—$SiH_2$($NMe_2$))$_2$($SiH_2$—$CH_2SiH_3$);
  the precursor being N($SiH_2$—$CH_2$—$SiH_2$(NMeEt))$_2$($SiH_2$—$CH_2SiH_3$);
  the precursor being N($SiH_2$—$CH_2$—$SiH_2$($NEt_2$))$_2$($SiH_2$—$CH_2SiH_3$);
  the precursor being N($SiH_2$—$CH_2$—$SiH_2$($NnPr_2$))$_2$($SiH_2$—$CH_2SiH_3$);
  the precursor being N($SiH_2$—$CH_2$—$SiH_2$($NiPr_2$))$_2$($SiH_2$—$CH_2SiH_3$);
  the precursor being N($SiH_2$—$CH_2$—$SiH_2$($NBu_2$))$_2$($SiH_2$—$CH_2SiH_3$);
  the precursor being N($SiH_2$—$CH_2$—$SiH_2$($NiBu_2$))$_2$($SiH_2$—$CH_2SiH_3$);
  the precursor being N($SiH_2$—$CH_2$—$SiH_2$($NtBu_2$))$_2$($SiH_2$—$CH_2SiH_3$);
  the precursor being N($SiH_2$—$CH_2$—$SiH_2$(NHtBu))$_2$($SiH_2$—$CH_2SiH_3$);
  the precursor being N($SiH_2$—$CH_2$—$SiH_2$($NAm_2$))$_2$($SiH_2$—$CH_2SiH_3$);
  the precursor being N($SiH_2$—$CH_2$—$SiH_2$(NHAm))$_2$($SiH_2$—$CH_2SiH_3$);
  the precursor being N($SiH_2$—$CH_2$—$SiH_2$(NCyPentyl$_2$))$_2$($SiH_2$—$CH_2SiH_3$);
  the precursor being N($SiH_2$—$CH_2$—$SiH_2$(Nhexyl$_2$))$_2$($SiH_2$—$CH_2SiH_3$);
  the precursor being N($SiH_2$—$CH_2$—$SiH_2$(NCyHex$_2$))$_2$($SiH_2$—$CH_2SiH_3$);
  the precursor being N($SiH_2$—$CH_2$—$SiH_2$(NMeH))$_2$($SiH_2$—$CH_2SiH_3$);
  the precursor being N($SiH_2$—$CH_2$—$SiH_2$(NEtH))$_2$($SiH_2$—$CH_2SiH_3$);
  the precursor being N($SiH_2$—$CH_2$—$SiH_2$(NnPrH))$_2$($SiH_2$—$CH_2SiH_3$);
  the precursor being N($SiH_2$—$CH_2$—$SiH_2$(NiPrH))$_2$($SiH_2$—$CH_2SiH_3$);
  the precursor being N($SiH_2$—$CH_2$—$SiH_2$(OH))$_2$($SiH_2$—$CH_2SiH_3$);
  the precursor being N($SiH_2$—$CH_2$—$SiH_2$(OMe))$_2$($SiH_2$—$CH_2SiH_3$);

the precursor being N(SiH$_2$—CH$_2$—SiH$_2$(OEt))$_2$(SiH$_2$—CH$_2$SiH$_3$);
the precursor being N(SiH$_2$—CH$_2$—SiH$_2$(OnPr))$_2$(SiH$_2$—CH$_2$SiH$_3$);
the precursor being N(SiH$_2$—CH$_2$—SiH$_2$(OiPr))$_2$(SiH$_2$—CH$_2$SiH$_3$);
the precursor being N(SiH$_2$—CH$_2$—SiH$_2$(OBu))$_2$(SiH$_2$—CH$_2$SiH$_3$);
the precursor being N(SiH$_2$—CH$_2$—SiH$_2$(OiBu))$_2$(SiH$_2$—CH$_2$SiH$_3$);
the precursor being N(SiH$_2$—CH$_2$—SiH$_2$(OtBu))$_2$(SiH$_2$—CH$_2$SiH$_3$);
the precursor being N(SiH$_2$—CH$_2$—SiH$_2$(OAm))$_2$(SiH$_2$—CH$_2$SiH$_3$);
the precursor being N(SiH$_2$—CH$_2$—SiH$_2$(OHexyl))$_2$(SiH$_2$—CH$_2$SiH$_3$);
the precursor being N(SiH$_2$—CH$_2$—SiH$_2$(Cl))(SiH$_2$—CH$_2$SiH$_3$)$_2$;
the precursor being N(SiH$_2$—CH$_2$—SiH$_2$(Br))(SiH$_2$—CH$_2$SiH$_3$)$_2$;
the precursor being N(SiH$_2$—CH$_2$—SiH$_2$(I))(SiH$_2$—CH$_2$SiH$_3$)$_2$;
the precursor being N(SiH$_2$—CH$_2$—SiH$_2$(NH$_2$))(SiH$_2$—CH$_2$SiH$_3$)$_2$;
the precursor being N(SiH$_2$—CH$_2$—SiH$_2$(NMe$_2$))(SiH$_2$—CH$_2$SiH$_3$)$_2$;
the precursor being N(SiH$_2$—CH$_2$—SiH$_2$(NMeEt))(SiH$_2$—CH$_2$SiH$_3$)$_2$;
the precursor being N(SiH$_2$—CH$_2$—SiH$_2$(NEt$_2$))(SiH$_2$—CH$_2$SiH$_3$)$_2$;
the precursor being N(SiH$_2$—CH$_2$—SiH$_2$(NnPr$_2$))(SiH$_2$—CH$_2$SiH$_3$)$_2$;
the precursor being N(SiH$_2$—CH$_2$—SiH$_2$(NiPr$_2$))(SiH$_2$—CH$_2$SiH$_3$)$_2$;
the precursor being N(SiH$_2$—CH$_2$—SiH$_2$(NBu$_2$))(SiH$_2$—CH$_2$SiH$_3$)$_2$;
the precursor being N(SiH$_2$—CH$_2$—SiH$_2$(NiBu$_2$))(SiH$_2$—CH$_2$SiH$_3$)$_2$;
the precursor being N(SiH$_2$—CH$_2$—SiH$_2$(NtBu$_2$))(SiH$_2$—CH$_2$SiH$_3$)$_2$;
the precursor being N(SiH$_2$—CH$_2$—SiH$_2$(NHtBu))(SiH$_2$—CH$_2$SiH$_3$)$_2$;
the precursor being N(SiH$_2$—CH$_2$—SiH$_2$(NAm$_2$))(SiH$_2$—CH$_2$SiH$_3$)$_2$;
the precursor being N(SiH$_2$—CH$_2$—SiH$_2$(NHAm))(SiH$_2$—CH$_2$SiH$_3$)$_2$;
the precursor being N(SiH$_2$—CH$_2$—SiH$_2$(NCyPentyl$_2$))(SiH$_2$—CH$_2$SiH$_3$)$_2$;
the precursor being N(SiH$_2$—CH$_2$—SiH$_2$(Nhexyl$_2$))(SiH$_2$—CH$_2$SiH$_3$)$_2$;
the precursor being N(SiH$_2$—CH$_2$—SiH$_2$(NCyHex$_2$))(SiH$_2$—CH$_2$SiH$_3$)$_2$;
the precursor being N(SiH$_2$—CH$_2$—SiH$_2$(NMeH))(SiH$_2$—CH$_2$SiH$_3$)$_2$;
the precursor being N(SiH$_2$—CH$_2$—SiH$_2$(NEtH))(SiH$_2$—CH$_2$SiH$_3$)$_2$;
the precursor being N(SiH$_2$—CH$_2$—SiH$_2$(NnPrH))(SiH$_2$—CH$_2$SiH$_3$)$_2$;
the precursor being N(SiH$_2$—CH$_2$—SiH$_2$(NiPrH))(SiH$_2$—CH$_2$SiH$_3$)$_2$;
the precursor being N(SiH$_2$—CH$_2$—SiH$_2$(OH))(SiH$_2$—CH$_2$SiH$_3$)$_2$;
the precursor being N(SiH$_2$—CH$_2$—SiH$_2$(OMe))(SiH$_2$—CH$_2$SiH$_3$)$_2$;
the precursor being N(SiH$_2$—CH$_2$—SiH$_2$(OEt))(SiH$_2$—CH$_2$SiH$_3$)$_2$;
the precursor being N(SiH$_2$—CH$_2$—SiH$_2$(OnPr))(SiH$_2$—CH$_2$SiH$_3$)$_2$;
the precursor being N(SiH$_2$—CH$_2$—SiH$_2$(OiPr))(SiH$_2$—CH$_2$SiH$_3$)$_2$;
the precursor being N(SiH$_2$—CH$_2$—SiH$_2$(OBu))(SiH$_2$—CH$_2$SiH$_3$)$_2$;
the precursor being N(SiH$_2$—CH$_2$—SiH$_2$(OiBu))(SiH$_2$—CH$_2$SiH$_3$)$_2$;
the precursor being N(SiH$_2$—CH$_2$—SiH$_2$(OtBu))(SiH$_2$—CH$_2$SiH$_3$)$_2$;
the precursor being N(SiH$_2$—CH$_2$—SiH$_2$(OAm))(SiH$_2$—CH$_2$SiH$_3$)$_2$;
the precursor being N(SiH$_2$—CH$_2$—SiH$_2$(OHexyl))(SiH$_2$—CH$_2$SiH$_3$)$_2$;
$R^3$=H;
the formula being N(—SiHR$^2$—CH$_2$—SiH$_3$)$_3$;
the precursor being N(Si(H)(Cl)—CH$_2$—SiH$_3$)$_3$;
the precursor being N(Si(H)(Br)—CH$_2$—SiH$_3$)$_3$;
the precursor being N(Si(H)(I)—CH$_2$—SiH$_3$)$_3$;
the precursor being N(Si(H)(NH$_2$)—CH$_2$—SiH$_3$)$_3$;
the precursor being N(Si(H)(NMe$_2$)-CH$_2$—SiH$_3$)$_3$;
the precursor being N(Si(H)(NEtMe)-CH$_2$—SiH$_3$)$_3$;
the precursor being N(Si(H)(NEt$_2$)-CH$_2$—SiH$_3$)$_3$;
the precursor being N(Si(H)(NnPr$_2$)—CH$_2$—SiH$_3$)$_3$;
the precursor being N(Si(H)(NiPr$_2$)—CH$_2$—SiH$_3$)$_3$;
the precursor being N(Si(H)(NBu$_2$)-CH$_2$—SiH$_3$)$_3$;
the precursor being N(Si(H)(NiBu$_2$)-CH$_2$—SiH$_3$)$_3$;
the precursor being N(Si(H)(NtBu$_2$)-CH$_2$—SiH$_3$)$_3$;
the precursor being N(Si(H)(NHtBu)-CH$_2$—SiH$_3$)$_3$;
the precursor being N(Si(H)(NAm$_2$)—CH$_2$—SiH$_3$)$_3$;
the precursor being N(Si(H)(NHAm)—CH$_2$—SiH$_3$)$_3$;
the precursor being N(Si(H)(NCyPentyl$_2$)-CH$_2$—SiH$_3$)$_3$;
the precursor being N(Si(H)(Nhexyl$_2$)—CH$_2$—SiH$_3$)$_3$;
the precursor being N(Si(H)(NCyHex$_2$)-CH$_2$—SiH$_3$)$_3$;
the precursor being N(Si(H)(NMeH)—CH$_2$—SiH$_3$)$_3$;
the precursor being N(Si(H)(NEtH)—CH$_2$—SiH$_3$)$_3$;
the precursor being N(Si(H)(NnPrH)—CH$_2$—SiH$_3$)$_3$;
the precursor being N(Si(H)(NiPrH)—CH$_2$—SiH$_3$)$_3$;
the precursor being N(Si(H)(NBuH)—CH$_2$—SiH$_3$)$_3$;
the precursor being N(Si(H)(NtBuH)—CH$_2$—SiH$_3$)$_3$;
the precursor being N(Si(H)(OH)—CH$_2$—SiH$_3$)$_3$;
the precursor being N(Si(H)(OMe)-CH$_2$—SiH$_3$)$_3$;
the precursor being N(Si(H)(OEt)-CH$_2$—SiH$_3$)$_3$;
the precursor being N(Si(H)(OnPr)—CH$_2$—SiH$_3$)$_3$;
the precursor being N(Si(H)(OiPr)—CH$_2$—SiH$_3$)$_3$;
the precursor being N(Si(H)(OBu)-CH$_2$—SiH$_3$)$_3$;
the precursor being N(Si(H)(OiBu)-CH$_2$—SiH$_3$)$_3$;
the precursor being N(Si(H)(OtBu)-CH$_2$—SiH$_3$)$_3$;
the precursor being N(Si(H)(OAm)—CH$_2$—SiH$_3$)$_3$;
the precursor being N(Si(H)(OHexyl)-CH$_2$—SiH$_3$)$_3$;
the precursor being N(Si(H)(Cl)—CH$_2$—SiH$_3$)$_2$(SiH$_2$—CH$_2$SiH$_3$);
the precursor being N(Si(H)(Br)—CH$_2$—SiH$_3$)$_2$(SiH$_2$—CH$_2$SiH$_3$);
the precursor being N(Si(H)(I)—CH$_2$—SiH$_3$)$_2$(SiH$_2$—CH$_2$SiH$_3$);
the precursor being N(Si(H)(NH$_2$)—CH$_2$—SiH$_3$)$_2$(SiH$_2$—CH$_2$SiH$_3$);
the precursor being N(Si(H)(NMe$_2$)-CH$_2$—SiH$_3$)$_2$(SiH$_2$—CH$_2$SiH$_3$);
the precursor being N(Si(H)(NMeEt)-CH$_2$—SiH$_3$)$_2$(SiH$_2$—CH$_2$SiH$_3$);
the precursor being N(Si(H)(NEt$_2$)-CH$_2$—SiH$_3$)$_2$(SiH$_2$—CH$_2$SiH$_3$);
the precursor being N(Si(H)(NnPr$_2$)—CH$_2$—SiH$_3$)$_2$(SiH$_2$—CH$_2$SiH$_3$);

the precursor being N(Si(H)(NiPr$_2$)—CH$_2$—SiH$_3$)$_2$ (SiH$_2$—CH$_2$SiH$_3$);
the precursor being N(Si(H)(NBu$_2$)-CH$_2$—SiH$_3$)$_2$ (SiH$_2$—CH$_2$SiH$_3$);
the precursor being N(Si(H)(NiBu$_2$)-CH$_2$—SiH$_3$)$_2$ (SiH$_2$—CH$_2$SiH$_3$);
the precursor being N(Si(H)(NtBu$_2$)-CH$_2$—SiH$_3$)$_2$ (SiH$_2$—CH$_2$SiH$_3$);
the precursor being N(Si(H)(NHtBu)—CH$_2$—SiH$_3$)$_2$ (SiH$_2$—CH$_2$SiH$_3$);
the precursor being N(Si(H)(NAm$_2$)—CH$_2$—SiH$_3$)$_2$ (SiH$_2$—CH$_2$SiH$_3$);
the precursor being N(Si(H)(NHAm)—CH$_2$—SiH$_3$)$_2$ (SiH$_2$—CH$_2$SiH$_3$);
the precursor being N(Si(H)(NCyPentyl$_2$)-CH$_2$—SiH$_3$)$_2$ (SiH$_2$—CH$_2$SiH$_3$);
the precursor being N(Si(H)(Nhexyl$_2$)-CH$_2$—SiH$_3$)$_2$ (SiH$_2$—CH$_2$SiH$_3$);
the precursor being N(Si(H)(NCyHex$_2$)-CH$_2$—SiH$_3$)$_2$ (SiH$_2$—CH$_2$SiH$_3$);
the precursor being N(Si(H)(NMeH)—CH$_2$—SiH$_3$)$_2$ (SiH$_2$—CH$_2$SiH$_3$);
the precursor being N(Si(H)(NEtH)—CH$_2$—SiH$_3$)$_2$ (SiH$_2$—CH$_2$SiH$_3$);
the precursor being N(Si(H)(NnPrH)—CH$_2$—SiH$_3$)$_2$ (SiH$_2$—CH$_2$SiH$_3$);
the precursor being N(Si(H)(NiPrH)—CH$_2$—SiH$_3$)$_2$ (SiH$_2$—CH$_2$SiH$_3$);
the precursor being N(Si(H)(OH)—CH$_2$—SiH$_3$)$_2$(SiH$_2$—CH$_2$SiH$_3$),
the precursor being N(Si(H)(OMe)-CH$_2$—SiH$_3$)$_2$(SiH$_2$—CH$_2$SiH$_3$);
the precursor being N(Si(H)(OEt)-CH$_2$—SiH$_3$)$_2$(SiH$_2$—CH$_2$SiH$_3$);
the precursor being N(Si(H)(OnPr)—CH$_2$—SiH$_3$)$_2$ (SiH$_2$—CH$_2$SiH$_3$);
the precursor being N(Si(H)(OiPr)—CH$_2$—SiH$_3$)$_2$ (SiH$_2$—CH$_2$SiH$_3$);
the precursor being N(Si(H)(OBu)-CH$_2$—SiH$_3$)$_2$(SiH$_2$—CH$_2$SiH$_3$);
the precursor being N(Si(H)(OiBu)-CH$_2$—SiH$_3$)$_2$(SiH$_2$—CH$_2$SiH$_3$);
the precursor being N(Si(H)(OtBu)-CH$_2$—SiH$_3$)$_2$(SiH$_2$—CH$_2$SiH$_3$);
the precursor being N(Si(H)(OAm)—CH$_2$—SiH$_3$)$_2$ (SiH$_2$—CH$_2$SiH$_3$);
the precursor being N(Si(H)(OHexyl)-CH$_2$—SiH$_3$)$_2$ (SiH$_2$—CH$_2$SiH$_3$);
the precursor being N(Si(H)(Cl)—CH$_2$—SiH$_3$)(SiH$_2$—CH$_2$SiH$_3$)$_2$;
the precursor being N(Si(H)(Br)—CH$_2$—SiH$_3$)(SiH$_2$—CH$_2$SiH$_3$)$_2$;
the precursor being N(Si(H)(I)—CH$_2$—SiH$_3$)(SiH$_2$—CH$_2$SiH$_3$)$_2$;
the precursor being N(Si(H)(NH$_2$)—CH$_2$—SiH$_3$)(SiH$_2$—CH$_2$SiH$_3$)$_2$;
the precursor being N(Si(H)(NMe$_2$)-CH$_2$—SiH$_3$)(SiH$_2$—CH$_2$SiH$_3$)$_2$;
the precursor being N(Si(H)(NMeEt)-CH$_2$—SiH$_3$)(SiH$_2$—CH$_2$SiH$_3$)$_2$;
the precursor being N(Si(H)(NEt$_2$)-CH$_2$—SiH$_3$)(SiH$_2$—CH$_2$SiH$_3$)$_2$;
the precursor being N(Si(H)(NnPr$_2$)—CH$_2$—SiH$_3$)(SiH$_2$—CH$_2$SiH$_3$)$_2$;
the precursor being N(Si(H)(NiPr$_2$)—CH$_2$—SiH$_3$)(SiH$_2$—CH$_2$SiH$_3$)$_2$;
the precursor being N(Si(H)(NBu$_2$)-CH$_2$—SiH$_3$)(SiH$_2$—CH$_2$SiH$_3$)$_2$;
the precursor being N(Si(H)(NiBu$_2$)-CH$_2$—SiH$_3$)(SiH$_2$—CH$_2$SiH$_3$)$_2$;
the precursor being N(Si(H)(NtBu$_2$)-CH$_2$—SiH$_3$)(SiH$_2$—CH$_2$SiH$_3$)$_2$;
the precursor being N(Si(H)(NHtBu)-CH$_2$—SiH$_3$)(SiH$_2$—CH$_2$SiH$_3$)$_2$;
the precursor being N(Si(H)(NAm$_2$)—CH$_2$—SiH$_3$)(SiH$_2$—CH$_2$SiH$_3$)$_2$;
the precursor being N(Si(H)(NHAm)—CH$_2$—SiH$_3$)(SiH$_2$—CH$_2$SiH$_3$)$_2$;
the precursor being N(Si(H)(NCyPentyl$_2$)-CH$_2$—SiH$_3$)(SiH$_2$—CH$_2$SiH$_3$)$_2$;
the precursor being N(Si(H)(Nhexyl$_2$)-CH$_2$—SiH$_3$)(SiH$_2$—CH$_2$SiH$_3$)$_2$;
the precursor being N(Si(H)(NCyHex$_2$)-CH$_2$—SiH$_3$)(SiH$_2$—CH$_2$SiH$_3$)$_2$;
the precursor being N(Si(H)(NMeH)—CH$_2$—SiH$_3$)(SiH$_2$—CH$_2$SiH$_3$)$_2$;
the precursor being N(Si(H)(NEtH)—CH$_2$—SiH$_3$)(SiH$_2$—CH$_2$SiH$_3$)$_2$;
the precursor being N(Si(H)(NnPrH)—CH$_2$—SiH$_3$)(SiH$_2$—CH$_2$SiH$_3$)$_2$;
the precursor being N(Si(H)(NiPrH)—CH$_2$—SiH$_3$)(SiH$_2$—CH$_2$SiH$_3$)$_2$;
the precursor being N(Si(H)(OH)—CH$_2$—SiH$_3$)(SiH$_2$—CH$_2$SiH$_3$)$_2$;
the precursor being N(Si(H)(OMe)-CH$_2$—SiH$_3$)(SiH$_2$—CH$_2$SiH$_3$)$_2$;
the precursor being N(Si(H)(OEt)-CH$_2$—SiH$_3$)(SiH$_2$—CH$_2$SiH$_3$)$_2$;
the precursor being N(Si(H)(OnPr)—CH$_2$—SiH$_3$)(SiH$_2$—CH$_2$SiH$_3$)$_2$;
the precursor being N(Si(H)(OiPr)—CH$_2$—SiH$_3$)(SiH$_2$—CH$_2$SiH$_3$)$_2$;
the precursor being N(Si(H)(OBu)-CH$_2$—SiH$_3$)(SiH$_2$—CH$_2$SiH$_3$)$_2$;
the precursor being (Si(H)(OiBu)-CH$_2$—SiH$_3$)(SiH$_2$—CH$_2$SiH$_3$)$_2$;
the precursor being N(Si(H)(OtBu)-CH$_2$—SiH$_3$)(SiH$_2$—CH$_2$SiH$_3$)$_2$;
the precursor being N(Si(H)(OAm)—CH$_2$—SiH$_3$)(SiH$_2$—CH$_2$SiH$_3$)$_2$;
the precursor being N(Si(H)(OHexyl)-CH$_2$—SiH$_3$)(SiH$_2$—CH$_2$SiH$_3$)$_2$;
a=1;
the formula is R$^1$N(—SiHR$^2$—CH$_2$—SiH$_2$R$^3$)$_2$;
the formula being R$^1$N(—SiH$_2$—CH$_2$—SiH$_2$R$_3$)$_2$;
R$^1$ being H;
the precursor being HN(SiH$_2$—CH$_2$SiH$_3$)$_2$;
the precursor being HN(SiH$_2$—CH$_2$—SiH$_2$(Cl))$_2$;
the precursor being HN(SiH$_2$—CH$_2$—SiH$_2$(Br))$_2$;
the precursor being HN(SiH$_2$—CH$_2$—SiH$_2$(I))$_2$;
the precursor being HN(SiH$_2$—CH$_2$—SiH$_2$(NH$_2$))$_2$;
the precursor being HN(SiH$_2$—CH$_2$—SiH$_2$(NMe$_2$))$_2$;
the precursor being HN(SiH$_2$—CH$_2$—SiH$_2$(NMeH))$_2$;
the precursor being HN(SiH$_2$—CH$_2$—SiH$_2$(NEtH))$_2$;
the precursor being HN(SiH$_2$—CH$_2$—SiH$_2$(NMeEt))$_2$;
the precursor being HN(SiH$_2$—CH$_2$—SiH$_2$(NiPrH))$_2$;
the precursor being HN(SiH$_2$—CH$_2$—SiH$_2$(OMe))$_2$;
the precursor being HN(SiH$_2$—CH$_2$—SiH$_2$(OEt))$_2$;
the precursor being (Cl)N(SiH$_2$—CH$_2$SiH$_3$)$_2$;
the precursor being (Br)N(SiH$_2$—CH$_2$SiH$_3$)$_2$;
the precursor being (I)N(SiH$_2$—CH$_2$SiH$_3$)$_2$;
the precursor being (Me)N(SiH$_2$—CH$_2$SiH$_3$)$_2$;
the precursor being (Et)N(SiH$_2$—CH$_2$SiH$_3$)$_2$;

the precursor being (nPr)N(SiH$_2$—CH$_2$SiH$_3$)$_2$;
the precursor being (iPr)N(SiH$_2$—CH$_2$SiH$_3$)$_2$;
the precursor being (Bu)N(SiH$_2$—CH$_2$SiH$_3$)$_2$;
the precursor being (iBu)N(SiH$_2$—CH$_2$SiH$_3$)$_2$;
the precursor being (tBu)N(SiH$_2$—CH$_2$SiH$_3$)$_2$;
the precursor being (amyl)N(SiH$_2$—CH$_2$SiH$_3$)$_2$;
the precursor being (hexyl)N(SiH$_2$—CH$_2$SiH$_3$)$_2$;
the precursor being (Me)N(SiH$_2$—CH$_2$—SiH$_2$(Cl))$_2$;
the precursor being (Et)N(SiH$_2$—CH$_2$—SiH$_2$(Cl))$_2$;
the precursor being (nPr)N(SiH$_2$—CH$_2$—SiH$_2$(Cl))$_2$;
the precursor being (iPr)N(SiH$_2$—CH$_2$—SiH$_2$(Cl))$_2$;
the precursor being (Bu)N(SiH$_2$—CH$_2$—SiH$_2$(Cl))$_2$;
the precursor being (iBu)N(SiH$_2$—CH$_2$—SiH$_2$(Cl))$_2$;
the precursor being (tBu)N(SiH$_2$—CH$_2$—SiH$_2$(Cl))$_2$;
the precursor being (amyl)N(SiH$_2$—CH$_2$—SiH$_2$(Cl))$_2$;
the precursor being (hexyl)N(SiH$_2$—CH$_2$—SiH$_2$(Cl))$_2$;
the precursor being (Me)N(SiH$_2$—CH$_2$—SiH$_2$(Br))$_2$;
the precursor being (Et)N(SiH$_2$—CH$_2$—SiH$_2$(Br))$_2$;
the precursor being (nPr)N(SiH$_2$—CH$_2$—SiH$_2$(Br))$_2$;
the precursor being (iPr)N(SiH$_2$—CH$_2$—SiH$_2$(Br))$_2$;
the precursor being (Bu)N(SiH$_2$—CH$_2$—SiH$_2$(Br))$_2$;
the precursor being (iBu)N(SiH$_2$—CH$_2$—SiH$_2$(Br))$_2$;
the precursor being (tBu)N(SiH$_2$—CH$_2$—SiH$_2$(Br))$_2$;
the precursor being (amyl)N(SiH$_2$—CH$_2$—SiH$_2$(Br))$_2$;
the precursor being (hexyl)N(SiH$_2$—CH$_2$—SiH$_2$(Br))$_2$;
the precursor being (Me)N(SiH$_2$—CH$_2$—SiH$_2$(I))$_2$;
the precursor being (Et)N(SiH$_2$—CH$_2$—SiH$_2$(I))$_2$;
the precursor being (nPr)N(SiH$_2$—CH$_2$—SiH$_2$(I))$_2$;
the precursor being (iPr)N(SiH$_2$—CH$_2$—SiH$_2$(I))$_2$;
the precursor being (Bu)N(SiH$_2$—CH$_2$—SiH$_2$(I))$_2$;
the precursor being (iBu)N(SiH$_2$—CH$_2$—SiH$_2$(I))$_2$;
the precursor being (tBu)N(SiH$_2$—CH$_2$—SiH$_2$(I))$_2$;
the precursor being (amyl)N(SiH$_2$—CH$_2$—SiH$_2$(I))$_2$;
the precursor being (hexyl)N(SiH$_2$—CH$_2$—SiH$_2$(I))$_2$;
the precursor being (Me)N(SiH$_2$—CH$_2$—SiH$_2$(NH$_2$))$_2$;
the precursor being (Et)N(SiH$_2$—CH$_2$—SiH$_2$(NH$_2$))$_2$;
the precursor being (nPr)N(SiH$_2$—CH$_2$—SiH$_2$(NH$_2$))$_2$;
the precursor being (iPr)N(SiH$_2$—CH$_2$—SiH$_2$(NH$_2$))$_2$;
the precursor being (Bu)N(SiH$_2$—CH$_2$—SiH$_2$(NH$_2$))$_2$;
the precursor being (iBu)N(SiH$_2$—CH$_2$—SiH$_2$(NH$_2$))$_2$;
the precursor being (tBu)N(SiH$_2$—CH$_2$—SiH$_2$(NH$_2$))$_2$;
the precursor being (amyl)N(SiH$_2$—CH$_2$—SiH$_2$(NH$_2$))$_2$;
the precursor being (hexyl)N(SiH$_2$—CH$_2$—SiH$_2$(NH$_2$))$_2$;
the precursor being (Me)N(SiH$_2$—CH$_2$—SiH$_2$(NMe$_2$))$_2$;
the precursor being (Et)N(SiH$_2$—CH$_2$—SiH$_2$(NMe$_2$))$_2$;
the precursor being (nPr)N(SiH$_2$—CH$_2$—SiH$_2$(NMe$_2$))$_2$;
the precursor being (iPr)N(SiH$_2$—CH$_2$—SiH$_2$(NMe$_2$))$_2$;
the precursor being (Bu)N(SiH$_2$—CH$_2$—SiH$_2$(NMe$_2$))$_2$;
the precursor being (iBu)N(SiH$_2$—CH$_2$—SiH$_2$(NMe$_2$))$_2$;
the precursor being (tBu)N(SiH$_2$—CH$_2$—SiH$_2$(NMe$_2$))$_2$;
the precursor being (amyl)N(SiH$_2$—CH$_2$—SiH$_2$(NMe$_2$))$_2$;
the precursor being (hexyl)N(SiH$_2$—CH$_2$—SiH$_2$(NMe$_2$))$_2$;
the precursor being (Me)N(SiH$_2$—CH$_2$—SiH$_2$(NMeH))$_2$;
the precursor being (Et)N(SiH$_2$—CH$_2$—SiH$_2$(NMeH))$_2$;
the precursor being (nPr)N(SiH$_2$—CH$_2$—SiH$_2$(NMeH))$_2$;
the precursor being (iPr)N(SiH$_2$—CH$_2$—SiH$_2$(NMeH))$_2$;
the precursor being (Bu)N(SiH$_2$—CH$_2$—SiH$_2$(NMeH))$_2$;
the precursor being (iBu)N(SiH$_2$—CH$_2$—SiH$_2$(NMeH))$_2$;
the precursor being (tBu)N(SiH$_2$—CH$_2$—SiH$_2$(NMeH))$_2$;
the precursor being (amyl)N(SiH$_2$—CH$_2$—SiH$_2$(NMeH))$_2$;
the precursor being (hexyl)N(SiH$_2$—CH$_2$—SiH$_2$(NMeH))$_2$;
the precursor being (Me)N(SiH$_2$—CH$_2$—SiH$_2$(NMeEt))$_2$;
the precursor being (Et)N(SiH$_2$—CH$_2$—SiH$_2$(NMeEt))$_2$;
the precursor being (nPr)N(SiH$_2$—CH$_2$—SiH$_2$(NMeEt))$_2$;
the precursor being (iPr)N(SiH$_2$—CH$_2$—SiH$_2$(NMeEt))$_2$;
the precursor being (Bu)N(SiH$_2$—CH$_2$—SiH$_2$(NMeEt))$_2$;
the precursor being (iBu)N(SiH$_2$—CH$_2$—SiH$_2$(NMeEt))$_2$;
the precursor being (tBu)N(SiH$_2$—CH$_2$—SiH$_2$(NMeEt))$_2$;
the precursor being (amyl)N(SiH$_2$—CH$_2$—SiH$_2$(NMeEt))$_2$;
the precursor being (hexyl)N(SiH$_2$—CH$_2$—SiH$_2$(NMeEt))$_2$;
the precursor being (Me)N(SiH$_2$—CH$_2$—SiH$_2$(NEtH))$_2$;
the precursor being (Et)N(SiH$_2$—CH$_2$—SiH$_2$(NEtH))$_2$;
the precursor being (nPr)N(SiH$_2$—CH$_2$—SiH$_2$(NEtH))$_2$;
the precursor being (iPr)N(SiH$_2$—CH$_2$—SiH$_2$(NEtH))$_2$;
the precursor being (Bu)N(SiH$_2$—CH$_2$—SiH$_2$(NEtH))$_2$;
the precursor being (iBu)N(SiH$_2$—CH$_2$—SiH$_2$(NEtH))$_2$;
the precursor being (tBu)N(SiH$_2$—CH$_2$—SiH$_2$(NEtH))$_2$;
the precursor being (amyl)N(SiH$_2$—CH$_2$—SiH$_2$(NEtH))$_2$;
the precursor being (hexyl)N(SiH$_2$—CH$_2$—SiH$_2$(NEtH))$_2$;
the precursor being (Me)N(SiH$_2$—CH$_2$—SiH$_2$(NiPrH))$_2$;
the precursor being (Et)N(SiH$_2$—CH$_2$—SiH$_2$(NiPrH))$_2$;
the precursor being (nPr)N(SiH$_2$—CH$_2$—SiH$_2$(NiPrH))$_2$;
the precursor being (iPr)N(SiH$_2$—CH$_2$—SiH$_2$(NiPrH))$_2$;
the precursor being (Bu)N(SiH$_2$—CH$_2$—SiH$_2$(NiPrH))$_2$;
the precursor being (iBu)N(SiH$_2$—CH$_2$—SiH$_2$(NiPrH))$_2$;
the precursor being (tBu)N(SiH$_2$—CH$_2$—SiH$_2$(NiPrH))$_2$;
the precursor being (amyl)N(SiH$_2$—CH$_2$—SiH$_2$(NiPrH))$_2$;
the precursor being (hexyl)N(SiH$_2$—CH$_2$—SiH$_2$(NiPrH))$_2$;
the precursor being (Me)N(SiH$_2$—CH$_2$—SiH$_2$(OMe))$_2$;
the precursor being (Et)N(SiH$_2$—CH$_2$—SiH$_2$(OMe))$_2$;
the precursor being (nPr)N(SiH$_2$—CH$_2$—SiH$_2$(OMe))$_2$;
the precursor being (iPr)N(SiH$_2$—CH$_2$—SiH$_2$(OMe))$_2$;
the precursor being (Bu)N(SiH$_2$—CH$_2$—SiH$_2$(OMe))$_2$;
the precursor being (iBu)N(SiH$_2$—CH$_2$—SiH$_2$(OMe))$_2$;
the precursor being (tBu)N(SiH$_2$—CH$_2$—SiH$_2$(OMe))$_2$;
the precursor being (amyl)N(SiH$_2$—CH$_2$—SiH$_2$(OMe))$_2$;
the precursor being (hexyl)N(SiH$_2$—CH$_2$—SiH$_2$(OMe))$_2$;
the precursor being (Me)N(SiH$_2$—CH$_2$—SiH$_2$(OEt))$_2$;
the precursor being (Et)N(SiH$_2$—CH$_2$—SiH$_2$(OEt))$_2$;
the precursor being (nPr)N(SiH$_2$—CH$_2$—SiH$_2$(OEt))$_2$;
the precursor being (iPr)N(SiH$_2$—CH$_2$—SiH$_2$(OEt))$_2$;
the precursor being (Bu)N(SiH$_2$—CH$_2$—SiH$_2$(OEt))$_2$;
the precursor being (iBu)N(SiH$_2$—CH$_2$—SiH$_2$(OEt))$_2$;
the precursor being (tBu)N(SiH$_2$—CH$_2$—SiH$_2$(OEt))$_2$;
the precursor being (amyl)N(SiH$_2$—CH$_2$—SiH$_2$(OEt))$_2$;
the precursor being (hexyl)N(SiH$_2$—CH$_2$—SiH$_2$(OEt))$_2$;
the formula being R$^1$N(—SiHR$^2$—CH$_2$—SiH$_3$)$_2$;
the precursor being HN(Si(H)(Cl)—CH$_2$—SiH$_3$)$_2$;
the precursor being (Me)N(Si(H)(Cl)—CH$_2$—SiH$_3$)$_2$;
the precursor being (Et)N(Si(H)(Cl)—CH$_2$—SiH$_3$)$_2$;
the precursor being (nPr)N(Si(H)(Cl)—CH$_2$—SiH$_3$)$_2$;
the precursor being (iPr)N(Si(H)(Cl)—CH$_2$—SiH$_3$)$_2$;
the precursor being (Bu)N(Si(H)(Cl)—CH$_2$—SiH$_3$)$_2$;
the precursor being (iBu)N(Si(H)(Cl)—CH$_2$—SiH$_3$)$_2$;
the precursor being (tBu)N(Si(H)(Cl)—CH$_2$—SiH$_3$)$_2$;

the precursor being (amyl)N(Si(H)(Cl)—CH$_2$—SiH$_3$)$_2$;
the precursor being (hexyl)N(Si(H)(Cl)—CH$_2$—SiH$_3$)$_2$;
the precursor being HN(Si(H)(Br)—CH$_2$—SiH$_3$)$_2$;
the precursor being (Me)N(Si(H)(Br)—CH$_2$—SiH$_3$)$_2$;
the precursor being (Et)N(Si(H)(Br)—CH$_2$—SiH$_3$)$_2$;
the precursor being (nPr)N(Si(H)(Br)—CH$_2$—SiH$_3$)$_2$;
the precursor being (iPr)N(Si(H)(Br)—CH$_2$—SiH$_3$)$_2$;
the precursor being (Bu)N(Si(H)(Br)—CH$_2$—SiH$_3$)$_2$;
the precursor being (iBu)N(Si(H)(Br)—CH$_2$—SiH$_3$)$_2$;
the precursor being (tBu)N(Si(H)(Br)—CH$_2$—SiH$_3$)$_2$;
the precursor being (amyl)N(Si(H)(Br)—CH$_2$—SiH$_3$)$_2$;
the precursor being (hexyl)N(Si(H)(Br)—CH$_2$—SiH$_3$)$_2$;
the precursor being HN(Si(H)(I)—CH$_2$—SiH$_3$)$_2$;
the precursor being (Me)N(Si(H)(I)—CH$_2$—SiH$_3$)$_2$;
the precursor being (Et)N(Si(H)(I)—CH$_2$—SiH$_3$)$_2$;
the precursor being (nPr)N(Si(H)(I)—CH$_2$—SiH$_3$)$_2$;
the precursor being (iPr)N(Si(H)(I)—CH$_2$—SiH$_3$)$_2$;
the precursor being (Bu)N(Si(H)(I)—CH$_2$—SiH$_3$)$_2$;
the precursor being (iBu)N(Si(H)(I)—CH$_2$—SiH$_3$)$_2$;
the precursor being (tBu)N(Si(H)(I)—CH$_2$—SiH$_3$)$_2$;
the precursor being (amyl)N(Si(H)(I)—CH$_2$—SiH$_3$)$_2$;
the precursor being (hexyl)N(Si(H)(I)—CH$_2$—SiH$_3$)$_2$;
the precursor being HN(Si(H)(NH$_2$)—CH$_2$—SiH$_3$)$_2$;
the precursor being (Me)N(Si(H)(NH$_2$)—CH$_2$—SiH$_3$)$_2$;
the precursor being (Et)N(Si(H)(NH$_2$)—CH$_2$—SiH$_3$)$_2$;
the precursor being (nPr)N(Si(H)(NH$_2$)—CH$_2$—SiH$_3$)$_2$;
the precursor being (iPr)N(Si(H)(NH$_2$)—CH$_2$—SiH$_3$)$_2$;
the precursor being (Bu)N(Si(H)(NH$_2$)—CH$_2$—SiH$_3$)$_2$;
the precursor being (iBu)N(Si(H)(NH$_2$)—CH$_2$—SiH$_3$)$_2$;
the precursor being (tBu)N(Si(H)(NH$_2$)—CH$_2$—SiH$_3$)$_2$;
the precursor being (amyl)N(Si(H)(NH$_2$)—CH$_2$—SiH$_3$)$_2$;
the precursor being (hexyl)N(Si(H)(NH$_2$)—CH$_2$—SiH$_3$)$_2$;
the precursor being HN(Si(H)(NMe$_2$)-CH$_2$—SiH$_3$)$_2$;
the precursor being (Me)N(Si(H)(NMe$_2$)-CH$_2$—SiH$_3$)$_2$;
the precursor being (Et)N(Si(H)(NMe$_2$)-CH$_2$—SiH$_3$)$_2$;
the precursor being (nPr)N(Si(H)(NMe$_2$)-CH$_2$—SiH$_3$)$_2$;
the precursor being (iPr)N(Si(H)(NMe$_2$)-CH$_2$—SiH$_3$)$_2$;
the precursor being (Bu)N(Si(H)(NMe$_2$)-CH$_2$—SiH$_3$)$_2$;
the precursor being (iBu)N(Si(H)(NMe$_2$)-CH$_2$—SiH$_3$)$_2$;
the precursor being (tBu)N(Si(H)(NMe$_2$)-CH$_2$—SiH$_3$)$_2$;
the precursor being (amyl)N(Si(H)(NMe$_2$)-CH$_2$—SiH$_3$)$_2$;
the precursor being (hexyl)N(Si(H)(NMe$_2$)-CH$_2$—SiH$_3$)$_2$;
the precursor being HN(Si(H)(NMeEt)-CH$_2$—SiH$_3$)$_2$;
the precursor being (Me)N(Si(H)(NMeEt)-CH$_2$—SiH$_3$)$_2$;
the precursor being (Et)N(Si(H)(NMeEt)-CH$_2$—SiH$_3$)$_2$;
the precursor being (nPr)N(Si(H)(NMeEt)-CH$_2$—SiH$_3$)$_2$;
the precursor being (iPr)N(Si(H)(NMeEt)-CH$_2$—SiH$_3$)$_2$;
the precursor being (Bu)N(Si(H)(NMeEt)-CH$_2$—SiH$_3$)$_2$;
the precursor being (iBu)N(Si(H)(NMeEt)-CH$_2$—SiH$_3$)$_2$;
the precursor being (tBu)N(Si(H)(NMeEt)-CH$_2$—SiH$_3$)$_2$;
the precursor being (amyl)N(Si(H)(NMeEt)-CH$_2$—SiH$_3$)$_2$;
the precursor being (hexyl)N(Si(H)(NMeEt)-CH$_2$—iH$_3$)$_2$;
the precursor being HN(Si(H)(NMeH)—CH$_2$—SiH$_3$)$_2$;
the precursor being (Me)N(Si(H)(NMeH)—CH$_2$—SiH$_3$)$_2$;
the precursor being (Et)N(Si(H)(NMeH)—CH$_2$—SiH$_3$)$_2$;
the precursor being (nPr)N(Si(H)(NMeH)—CH$_2$—SiH$_3$)$_2$;
the precursor being (iPr)N(Si(H)(NMeH)—CH$_2$—SiH$_3$)$_2$;
the precursor being (Bu)N(Si(H)(NMeH)—CH$_2$—SiH$_3$)$_2$;
the precursor being (iBu)N(Si(H)(NMeH)—CH$_2$—SiH$_3$)$_2$;
the precursor being (tBu)N(Si(H)(NMeH)—CH$_2$—SiH$_3$)$_2$;
the precursor being (amyl)N(Si(H)(NMeH)—CH$_2$—SiH$_3$)$_2$;
the precursor being (hexyl)N(Si(H)(NMeH)—CH$_2$—SiH$_3$)$_2$;
the precursor being HN(Si(H)(NEtH)—CH$_2$—SiH$_3$)$_2$;
the precursor being (Me)N(Si(H)(NEtH)—CH$_2$—SiH$_3$)$_2$;
the precursor being (Et)N(Si(H)(NEtH)—CH$_2$—SiH$_3$)$_2$;
the precursor being (nPr)N(Si(H)(NEtH)—CH$_2$—SiH$_3$)$_2$;
the precursor being (iPr)N(Si(H)(NEtH)—CH$_2$—SiH$_3$)$_2$;
the precursor being (Bu)N(Si(H)(NEtH)—CH$_2$—SiH$_3$)$_2$;
the precursor being (iBu)N(Si(H)(NEtH)—CH$_2$—SiH$_3$)$_2$;
the precursor being (tBu)N(Si(H)(NEtH)—CH$_2$—SiH$_3$)$_2$;
the precursor being (amyl)N(Si(H)(NEtH)—CH$_2$—SiH$_3$)$_2$;
the precursor being (hexyl)N(Si(H)(NEtH)—CH$_2$—SiH$_3$)$_2$;
the precursor being HN(Si(H)(NiPrH)—CH$_2$—SiH$_3$)$_2$;
the precursor being (Me)N(Si(H)(NiPrH)—CH$_2$—SiH$_3$)$_2$;
the precursor being (Et)N(Si(H)(NiPrH)—CH$_2$—SiH$_3$)$_2$;
the precursor being (nPr)N(Si(H)(NiPrH)—CH$_2$—SiH$_3$)$_2$;
the precursor being (iPr)N(Si(H)(NiPrH)—CH$_2$—SiH$_3$)$_2$;
the precursor being (Bu)N(Si(H)(NiPrH)—CH$_2$—SiH$_3$)$_2$;
the precursor being (iBu)N(Si(H)(NiPrH)—CH$_2$—SiH$_3$)$_2$;
the precursor being (tBu)N(Si(H)(NiPrH)—CH$_2$—SiH$_3$)$_2$;
the precursor being (amyl)N(Si(H)(NiPrH)—CH$_2$—SiH$_3$)$_2$;
the precursor being (hexyl)N(Si(H)(NiPrH)—CH$_2$—SiH$_3$)$_2$;
the precursor being HN(Si(H)(NtBuH)—CH$_2$—SiH$_3$)$_2$;
the precursor being (Me)N(Si(H)(NtBuH)—CH$_2$—SiH$_3$)$_2$;
the precursor being (Et)N(Si(H)(NtBuH)—CH$_2$—SiH$_3$)$_2$;
the precursor being (nPr)N(Si(H)(NtBuH)—CH$_2$—SiH$_3$)$_2$;
the precursor being (iPr)N(Si(H)(NtBuH)—CH$_2$—SiH$_3$)$_2$;
the precursor being (Bu)N(Si(H)(NtBuH)—CH$_2$—SiH$_3$)$_2$;
the precursor being (iBu)N(Si(H)(NtBuH)—CH$_2$—SiH$_3$)$_2$;
the precursor being (tBu)N(Si(H)(NtBuH)—CH$_2$—SiH$_3$)$_2$;
the precursor being (amyl)N(Si(H)(NtBuH)—CH$_2$—SiH$_3$)$_2$;
the precursor being (hexyl)N(Si(H)(NtBuH)—CH$_2$—SiH$_3$)$_2$;
the precursor being HN(Si(H)(OEt)-CH$_2$—SiH$_3$)$_2$;
the precursor being (Me)N(Si(H)(OEt)-CH$_2$—SiH$_3$)$_2$;
the precursor being (Et)N(Si(H)(OEt)-CH$_2$—SiH$_3$)$_2$;
the precursor being (nPr)N(Si(H)(OEt)-CH$_2$—SiH$_3$)$_2$;
the precursor being (iPr)N(Si(H)(OEt)-CH$_2$—SiH$_3$)$_2$;
the precursor being (Bu)N(Si(H)(OEt)-CH$_2$—SiH$_3$)$_2$;
the precursor being (iBu)N(Si(H)(OEt)-CH$_2$—SiH$_3$)$_2$;
the precursor being (tBu)N(Si(H)(OEt)-CH$_2$—SiH$_3$)$_2$;
the precursor being (amyl)N(Si(H)(OEt)-CH$_2$—SiH$_3$)$_2$;
the precursor being (hexyl)N(Si(H)(OEt)-CH$_2$—SiH$_3$)$_2$;
the precursor being HN(SiH$_2$—CH$_2$—SiH$_2$(Cl))(SiH$_2$—CH$_2$SiH$_3$);

the precursor being MeN(SiH$_2$—CH$_2$—SiH$_2$(Cl))(SiH$_2$—CH$_2$SiH$_3$);
the precursor being EtN(SiH$_2$—CH$_2$—SiH$_2$(Cl))(SiH$_2$—CH$_2$SiH$_3$);
the precursor being iPrN(SiH$_2$—CH$_2$—SiH$_2$(Cl))(SiH$_2$—CH$_2$SiH$_3$);
the precursor being (Cl)N(SiH$_2$—CH$_2$—SiH$_2$(Cl))(SiH$_2$—CH$_2$SiH$_3$);
the precursor being (Br)N(SiH$_2$—CH$_2$—SiH$_2$(Cl))(SiH$_2$—CH$_2$SiH$_3$);
the precursor being (I)N(SiH$_2$—CH$_2$—SiH$_2$(Cl))(SiH$_2$—CH$_2$SiH$_3$);
the precursor being HN(SiH$_2$—CH$_2$—SiH$_2$(Br))(SiH$_2$—CH$_2$SiH$_3$);
the precursor being MeN(SiH$_2$—CH$_2$—SiH$_2$(Br))(SiH$_2$—CH$_2$SiH$_3$);
the precursor being EtN(SiH$_2$—CH$_2$—SiH$_2$(Br))(SiH$_2$—CH$_2$SiH$_3$);
the precursor being iPrN(SiH$_2$—CH$_2$—SiH$_2$(Br))(SiH$_2$—CH$_2$SiH$_3$);
the precursor being (Cl)N(SiH$_2$—CH$_2$—SiH$_2$(Br))(SiH$_2$—CH$_2$SiH$_3$);
the precursor being (Br)N(SiH$_2$—CH$_2$—SiH$_2$(Br))(SiH$_2$—CH$_2$SiH$_3$);
the precursor being (I)N(SiH$_2$—CH$_2$—SiH$_2$(Br))(SiH$_2$—CH$_2$SiH$_3$);
the precursor being HN(SiH$_2$—CH$_2$—SiH$_2$(I))(SiH$_2$—CH$_2$SiH$_3$);
the precursor being MeN(SiH$_2$—CH$_2$—SiH$_2$(I))(SiH$_2$—CH$_2$SiH$_3$);
the precursor being EtN(SiH$_2$—CH$_2$—SiH$_2$(I))(SiH$_2$—CH$_2$SiH$_3$);
the precursor being iPrN(SiH$_2$—CH$_2$—SiH$_2$(I))(SiH$_2$—CH$_2$SiH$_3$);
the precursor being (Cl)N(SiH$_2$—CH$_2$—SiH$_2$(I))(SiH$_2$—CH$_2$SiH$_3$);
the precursor being (Br)N(SiH$_2$—CH$_2$—SiH$_2$(I))(SiH$_2$—CH$_2$SiH$_3$);
the precursor being (I)N(SiH$_2$—CH$_2$—SiH$_2$(I))(SiH$_2$—CH$_2$SiH$_3$);
the precursor being HN(SiH$_2$—CH$_2$—SiH$_2$(NH$_2$))(SiH$_2$—CH$_2$SiH$_3$);
the precursor being MeN(SiH$_2$—CH$_2$—SiH$_2$(NH$_2$))(SiH$_2$—CH$_2$SiH$_3$);
the precursor being EtN(SiH$_2$—CH$_2$—SiH$_2$(NH$_2$))(SiH$_2$—CH$_2$SiH$_3$);
the precursor being iPrN(SiH$_2$—CH$_2$—SiH$_2$(NH$_2$))(SiH$_2$—CH$_2$SiH$_3$);
the precursor being (Cl)N(SiH$_2$—CH$_2$—SiH$_2$(NH$_2$))(SiH$_2$—CH$_2$SiH$_3$);
the precursor being (Br)N(SiH$_2$—CH$_2$—SiH$_2$(NH$_2$))(SiH$_2$—CH$_2$SiH$_3$);
the precursor being (I)N(SiH$_2$—CH$_2$—SiH$_2$(NH$_2$))(SiH$_2$—CH$_2$SiH$_3$);
the precursor being HN(SiH$_2$—CH$_2$—SiH$_2$(NMe$_2$))(SiH$_2$—CH$_2$SiH$_3$);
the precursor being MeN(SiH$_2$—CH$_2$—SiH$_2$(NMe$_2$))(SiH$_2$—CH$_2$SiH$_3$);
the precursor being EtN(SiH$_2$—CH$_2$—SiH$_2$(NMe$_2$))(SiH$_2$—CH$_2$SiH$_3$);
the precursor being iPrN(SiH$_2$—CH$_2$—SiH$_2$(NMe$_2$))(SiH$_2$—CH$_2$SiH$_3$);
the precursor being (Cl)N(SiH$_2$—CH$_2$—SiH$_2$(NMe$_2$))(SiH$_2$—CH$_2$SiH$_3$);
the precursor being (Br)N(SiH$_2$—CH$_2$—SiH$_2$(NMe$_2$))(SiH$_2$—CH$_2$SiH$_3$);
the precursor being (I)N(SiH$_2$—CH$_2$—SiH$_2$(NMe$_2$))(SiH$_2$—CH$_2$SiH$_3$);
the precursor being HN(SiH$_2$—CH$_2$—SiH$_2$(OMe))(SiH$_2$—CH$_2$SiH$_3$);
the precursor being MeN(SiH$_2$—CH$_2$—SiH$_2$(OMe))(SiH$_2$—CH$_2$SiH$_3$);
the precursor being EtN(SiH$_2$—CH$_2$—SiH$_2$(OMe))(SiH$_2$—CH$_2$SiH$_3$);
the precursor being iPrN(SiH$_2$—CH$_2$—SiH$_2$(OMe))(SiH$_2$—CH$_2$SiH$_3$);
the precursor being (Cl)N(SiH$_2$—CH$_2$—SiH$_2$(OMe))(SiH$_2$—CH$_2$SiH$_3$);
the precursor being (Br)N(SiH$_2$—CH$_2$—SiH$_2$(OMe))(SiH$_2$—CH$_2$SiH$_3$);
the precursor being (I)N(SiH$_2$—CH$_2$—SiH$_2$(OMe))(SiH$_2$—CH$_2$SiH$_3$);
the precursor being HN(SiH$_2$—CH$_2$—SiH$_2$(OEt))(SiH$_2$—CH$_2$SiH$_3$);
the precursor being MeN(SiH$_2$—CH$_2$—SiH$_2$(OEt))(SiH$_2$—CH$_2$SiH$_3$);
the precursor being EtN(SiH$_2$—CH$_2$—SiH$_2$(OEt))(SiH$_2$—CH$_2$SiH$_3$);
the precursor being iPrN(SiH$_2$—CH$_2$—SiH$_2$(OEt))(SiH$_2$—CH$_2$SiH$_3$);
the precursor being (Cl)N(SiH$_2$—CH$_2$—SiH$_2$(OEt))(SiH$_2$—CH$_2$SiH$_3$);
the precursor being (Br)N(SiH$_2$—CH$_2$—SiH$_2$(OEt))(SiH$_2$—CH$_2$SiH$_3$);
the precursor being (I)N(SiH$_2$—CH$_2$—SiH$_2$(OEt))(SiH$_2$—CH$_2$SiH$_3$);
the precursor being HN(Si(H)(Cl)—CH$_2$—SiH$_3$)(SiH$_2$—CH$_2$SiH$_3$);
the precursor being MeN(Si(H)(Cl)—CH$_2$—SiH$_3$)(SiH$_2$—CH$_2$SiH$_3$);
the precursor being EtN(Si(H)(Cl)—CH$_2$—SiH$_3$)(SiH$_2$—CH$_2$SiH$_3$);
the precursor being iPrN(Si(H)(Cl)—CH$_2$—SiH$_3$)(SiH$_2$—CH$_2$SiH$_3$);
the precursor being (Cl)N(Si(H)(Cl)—CH$_2$—SiH$_3$)(SiH$_2$—CH$_2$SiH$_3$);
the precursor being (Br)N(Si(H)(Cl)—CH$_2$—SiH$_3$)(SiH$_2$—CH$_2$SiH$_3$);
the precursor being (I)N(Si(H)(Cl)—CH$_2$—SiH$_3$)(SiH$_2$—CH$_2$SiH$_3$);
the precursor being HN(Si(H)(Br)—CH$_2$—SiH$_3$)(SiH$_2$—CH$_2$SiH$_3$);
the precursor being MeN(Si(H)(Br)—CH$_2$—SiH$_3$)(SiH$_2$—CH$_2$SiH$_3$);
the precursor being EtN(Si(H)(Br)—CH$_2$—SiH$_3$)(SiH$_2$—CH$_2$SiH$_3$);
the precursor being iPrN(Si(H)(Br)—CH$_2$—SiH$_3$)(SiH$_2$—CH$_2$SiH$_3$);
the precursor being (Cl)N(Si(H)(Br)—CH$_2$—SiH$_3$)(SiH$_2$—CH$_2$SiH$_3$);
the precursor being (Br)N(Si(H)(Br)—CH$_2$—SiH$_3$)(SiH$_2$—CH$_2$SiH$_3$);
the precursor being (I)N(Si(H)(Br)—CH$_2$—SiH$_3$)(SiH$_2$—CH$_2$SiH$_3$);
the precursor being HN(Si(H)(I)—CH$_2$—SiH$_3$)(SiH$_2$—CH$_2$SiH$_3$);
the precursor being MeN(Si(H)(I)—CH$_2$—SiH$_3$)(SiH$_2$—CH$_2$SiH$_3$);
the precursor being EtN(Si(H)(I)—CH$_2$—SiH$_3$)(SiH$_2$—CH$_2$SiH$_3$);
the precursor being iPrN(Si(H)(I)—CH$_2$—SiH$_3$)(SiH$_2$—CH$_2$SiH$_3$);

the precursor being (Cl)N(Si(H)(I)—CH$_2$—SiH$_3$) (SiH$_2$—CH$_2$SiH$_3$);
the precursor being (Br)N(Si(H)(I)—CH$_2$—SiH$_3$) (SiH$_2$—CH$_2$SiH$_3$);
the precursor being (I)N(Si(H)(I)—CH$_2$—SiH$_3$)(SiH$_2$—CH$_2$SiH$_3$);
the precursor being HN(Si(H)(NH$_2$)—CH$_2$—SiH$_3$) (SiH$_2$—CH$_2$SiH$_3$);
the precursor being MeN(Si(H)(NH$_2$)—CH$_2$—SiH$_3$) (SiH$_2$—CH$_2$SiH$_3$);
the precursor being EtN(Si(H)(NH$_2$)—CH$_2$—SiH$_3$) (SiH$_2$—CH$_2$SiH$_3$);
the precursor being iPrN(Si(H)(NH$_2$)—CH$_2$—SiH$_3$) (SiH$_2$—CH$_2$SiH$_3$);
the precursor being (Cl)N(Si(H)(NH$_2$)—CH$_2$—SiH$_3$) (SiH$_2$—CH$_2$SiH$_3$);
the precursor being (Br)N(Si(H)(NH$_2$)—CH$_2$—SiH$_3$) (SiH$_2$—CH$_2$SiH$_3$);
the precursor being (I)N(Si(H)(NH$_2$)—CH$_2$—SiH$_3$) (SiH$_2$—CH$_2$SiH$_3$);
the precursor being HN(Si(H)(NMe$_2$)-CH$_2$—SiH$_3$) (SiH$_2$—CH$_2$SiH$_3$);
the precursor being MeN(Si(H)(NMe$_2$)-CH$_2$—SiH$_3$) (SiH$_2$—CH$_2$SiH$_3$);
the precursor being EtN(Si(H)(NMe$_2$)-CH$_2$—SiH$_3$) (SiH$_2$—CH$_2$SiH$_3$);
the precursor being iPrN(Si(H)(NMe$_2$)-CH$_2$—SiH$_3$) (SiH$_2$—CH$_2$SiH$_3$);
the precursor being (Cl)N(Si(H)(NMe$_2$)-CH$_2$—SiH$_3$) (SiH$_2$—CH$_2$SiH$_3$);
the precursor being (Br)N(Si(H)(NMe$_2$)-CH$_2$—SiH$_3$) (SiH$_2$—CH$_2$SiH$_3$);
the precursor being (I)N(Si(H)(NMe$_2$)-CH$_2$—SiH$_3$) (SiH$_2$—CH$_2$SiH$_3$);
the precursor being HN(Si(H)(OMe)-CH$_2$—SiH$_3$) (SiH$_2$—CH$_2$SiH$_3$);
the precursor being MeN(Si(H)(OMe)-CH$_2$—SiH$_3$) (SiH$_2$—CH$_2$SiH$_3$);
the precursor being EtN(Si(H)(OMe)-CH$_2$—SiH$_3$) (SiH$_2$—CH$_2$SiH$_3$);
the precursor being iPrN(Si(H)(OMe)-CH$_2$—SiH$_3$) (SiH$_2$—CH$_2$SiH$_3$);
the precursor being (Cl)N(Si(H)(OMe)-CH$_2$—SiH$_3$) (SiH$_2$—CH$_2$SiH$_3$);
the precursor being (Br)N(Si(H)(OMe)-CH$_2$—SiH$_3$) (SiH$_2$—CH$_2$SiH$_3$);
the precursor being (I)N(Si(H)(OMe)-CH$_2$—SiH$_3$) (SiH$_2$—CH$_2$SiH$_3$);
the precursor being HN(Si(H)(OEt)-CH$_2$—SiH$_3$)(SiH$_2$—CH$_2$SiH$_3$);
the precursor being MeN(Si(H)(OEt)-CH$_2$—SiH$_3$) (SiH$_2$—CH$_2$SiH$_3$);
the precursor being EtN(Si(H)(OEt)-CH$_2$—SiH$_3$)(SiH$_2$—CH$_2$SiH$_3$);
the precursor being iPrN(Si(H)(OEt)-CH$_2$—SiH$_3$) (SiH$_2$—CH$_2$SiH$_3$);
the precursor being (Cl)N(Si(H)(OEt)-CH$_2$—SiH$_3$) (SiH$_2$—CH$_2$SiH$_3$);
the precursor being (Br)N(Si(H)(OEt)-CH$_2$—SiH$_3$) (SiH$_2$—CH$_2$SiH$_3$);
the precursor being (I)N(Si(H)(OEt)-CH$_2$—SiH$_3$) (SiH$_2$—CH$_2$SiH$_3$);
the Si-containing film forming composition comprising between approximately 0.1 molar % and approximately 50 molar % of the carbosilane substituted amine precursor;
the Si-containing film forming composition comprising between approximately 93% w/w to approximately 100% w/w of the carbosilane substituted amine precursor;
the Si-containing film forming composition comprising between approximately 99% w/w to approximately 100% w/w of the carbosilane substituted amine precursor;
the Si-containing film forming composition comprising between approximately 0% w/w and 5% w/w of hexane, substituted hexane, pentane, substituted pentane, dimethyl ether, or anisole;
the Si-containing film forming composition comprising between approximately 0 ppmw and 200 ppm of Cl;
further comprising a solvent;
the solvent being selected from the group consisting of $C_1$-$C_{16}$ hydrocarbons, THF, DMO, ether, pyridine, and combinations thereof;
the solvent being a $C_1$-$C_{16}$ hydrocarbons;
the solvent being tetrahydrofuran (THF);
the solvent being dimethyl oxalate (DMO);
the solvent being ether;
the solvent being pyridine;
the solvent being ethanol; or
the solvent being isopropanol.

Also disclosed are methods of deposition a Si-containing layer on a substrate. The vapor of any of the Si-containing film forming compositions disclosed above is introduced into a reactor having a substrate disposed therein. At least part of the carbosilane substituted amine precursor is deposited onto the substrate to form a Si-containing layer using a deposition method. The disclosed methods may include one or more of the following aspects:

introducing into the reactor a vapor comprising a second precursor;
the second precursor comprising an element selected from the group consisting of group 2, group 13, group 14, transition metal, lanthanides, and combinations thereof;
the element of the second precursor being selected from Mg, Ca, Sr, Ba, Zr, Hf, Ti, Nb, Ta, Al, Si, Ge, Y, or lanthanides;
introducing a co-reactant into the reactor;
the co-reactant being selected from the group consisting of $O_2$, $O_3$, $H_2O$, $H_2O_2$, NO, $NO_2$, a carboxylic acid, radicals thereof, and combinations thereof;
the co-reactant being plasma treated oxygen;
the co-reactant being ozone;
the Si-containing layer being a silicon oxide layer;
the co-reactant being selected from the group consisting of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkysilanes (such as $Me_2SiH_2$, $Et_2SiH_2$, $MeSiH_3$, $EtSiH_3$), hydrazines (such as $N_2H_4$, $MeHNNH_2$, MeHNNHMe), organic amines (such as $NMeH_2$, $NEtH_2$, $NMe_2H$, $NEt_2H$, $NMe_3$, $NEt_3$, $(SiMe_3)_2NH$), pyrazoline, pyridine, B-containing molecules (such as $B_2H_6$, 9-borabicylo[3,3,1]none, trimethylboron, triethylboron, borazine), alkyl metals (such as trimethylaluminum, triethylaluminum, dimethylzinc, diethylzinc), radical species thereof, and mixtures thereof.
the co-reactant being selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;
the co-reactant being HCDS or PCDS;

the vapor deposition process being a chemical vapor deposition process;
the vapor deposition process being an atomic layer deposition (ALD) process;
the vapor deposition process being a spatial ALD process;
the vapor deposition process being a chemical vapor deposition process;
the silicon-containing layer being Si;
the silicon-containing layer being $SiO_2$;
the silicon-containing layer being SiC;
the silicon-containing layer being SiN;
the silicon-containing layer being SiON;
the silicon-containing layer being SiCN; and
the silicon-containing layer being SiCOH.

Also disclosed are methods of forming Si-containing films on substrates. A solution comprising any of the Si-containing film forming compositions disclosed above is contacted with the substrate and the Si-containing film formed via a spin coating, spray coating, dip coating, or slit coating technique to form the Si-containing film. The disclosed methods may include the following aspects:
the Si-containing film forming composition comprising ethanol;
the Si-containing film forming composition comprising isopropanol;
forming the Si-containing film via a spin coating technique;
forming the Si-containing film via a spray coating technique;
forming the Si-containing film via a dip coating technique;
forming the Si-containing film via a slit coating technique;
annealing the Si-containing film; or
laser treating the Si-containing film.

DETAILED DESCRIPTION OF PREFERRED EMBODIMENTS

Disclosed are Si-containing film forming compositions comprising carbosilane substituted amine precursors. Also disclosed are methods of synthesizing the carbosilane substituted amine precursors and methods of using the same to deposit silicon-containing films for manufacturing semiconductors.

The disclosed carbosilane substituted amine precursors have the formula $(R^1)_aN(-SiHR^2-CH_2-SiH_2R^3)_{3-a}$, wherein a=0 or 1: $R^1$ is H, an alkyl group (C1 to C6) or a halogen (Cl, Br or I); $R^2$ and/or $R^3$ is independently H, a halogen (Cl, Br or I), an alkoxy group having the formula OR', wherein R' is an alkyl group (C1 to C6), or an alkylamino group having the formula $NR''_2$, wherein each R'' is independently H, a C1-C6 alkyl group, a C1-C6 alkenyl group, or a C3-C10 aryl or heterocycle group.

When a=0, the disclosed carbosilane substituted amine precursor has the following formula:

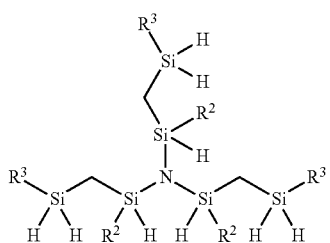

wherein $R^2$ and $R^3$ are each independently a H, a halogen (Cl, Br or I), an alkoxy group (OR'), wherein R' is an alkyl group (C1 to C6), or an alkylamino group having the formula $NR''_2$, wherein each R'' is independently H, a C1-C6 alkyl group, a C1-C6 alkenyl group, or a C3-C10 aryl or heterocycle group. The R'' of the alkylamino group may be joined to form a cyclic chain on the N atom. For example, $NR''_2$ may form pyridine, pyrole, pyrrolidine, or imidazole ring structures. The minimum of 5 Hs on each ($-SiHR^2-CH_2-SiH_2R^3$) group may provide improved volatility.

When a=0 and $R^2$ and $R^3$=H, the carbosilane substituted amine precursor is $N(SiH_2-CH_2-SiH_3)_3$.

Exemplary precursors wherein a=0 and $R^2$=H include $N(SiH_2-CH_2-SiH_2(Cl))_3$, $N(SiH_2-CH_2-SiH_2(Br))_3$, $N(SiH_2-CH_2-SiH_2(I))_3$, $N(SiH_2-CH_2-SiH_2(NH_2))_3$, $N(SiH_2-CH_2-SiH_2(NMe_2))_3$, $N(SiH_2-CH_2-SiH_2(NMeEt))_3$, $N(SiH_2-CH_2-SiH_2(NEt_2))_3$, $N(SiH_2-CH_2-SiH_2(NnPr_2))_3$, $N(SiH_2-CH_2-SiH_2(NiPr_2))_3$, $N(SiH_2-CH_2-SiH_2(NBu_2))_3$, $N(SiH_2-CH_2-SiH_2(NiBu_2))_3$, $N(SiH_2-CH_2-SiH_2(NtBu_2))_3$, $N(SiH_2-CH_2-SiH_2(NAm_2))_3$, $N(SiH_2-CH_2-SiH_2(NCyPentyl_2))_3$, $N(SiH_2-CH_2-SiH_2(Nhexyl_2))_3$, $N(SiH_2-CH_2-SiH_2(NCyHex_2))_3$, $N(SiH_2-CH_2-SiH_2(NMeH))_3$, $N(SiH_2-CH_2-SiH_2(NEtH))_3$, $N(SiH_2-CH_2-SiH_2(NnPrH))_3$, $N(SiH_2-CH_2-SiH_2(NiPrH))_3$, $N(SiH_2-CH_2-SiH_2(NBuH))_3$, $N(SiH_2-CH_2-SiH_2(NiBuH))_3$, $N(SiH_2-CH_2-SiH_2(NtBuH))_3$, $N(SiH_2-CH_2-SiH_2(NAmH))_3$, $N(SiH_2-CH_2-SiH_2(pyridine))_3$, $N(SiH_2-CH_2-SiH_2(pyrole))_3$, $N(SiH_2-CH_2-SiH_2(pyrrolidine))_3$, $N(SiH_2-CH_2-SiH_2(imidazole))_3$, $N(SiH_2-CH_2-SiH_2(OH))_3$, $N(SiH_2-CH_2-SiH_2(OMe))_3$, $N(SiH_2-CH_2-SiH_2(OEt))_3$, $N(SiH_2-CH_2-SiH_2(OnPr))_3$, $N(SiH_2-CH_2-SiH_2(OiPr))_3$, $N(SiH_2-CH_2-SiH_2(OBu))_3$, $N(SiH_2-CH_2-SiH_2(OiBu))_3$, $N(SiH_2-CH_2-SiH_2(OtBu))_3$, $N(SiH_2-CH_2-SiH_2(OAm))_3$, and $N(SiH_2-CH_2-SiH_2(OHexyl))_3$.

Exemplary precursors wherein a=0 and $R^3$=H include $N(Si(H)(Cl)-CH_2-SiH_3)_3$, $N(Si(H)(Br)-CH_2-SiH_3)_3$, $N(Si(H)(I)-CH_2-SiH_3)_3$, $N(Si(H)(NH_2)-CH_2-SiH_3)_3$, $N(Si(H)(NMe_2)-CH_2-SiH_3)_3$, $N(Si(H)(NEtMe)-CH_2-SiH_3)_3$, $N(Si(H)(NEt_2)-CH_2-SiH_3)_3$, $N(Si(H)(NnPr_2)-CH_2-SiH_3)_3$, $N(Si(H)(NiPr_2)-CH_2-SiH_3)_3$, $N(Si(H)(NBu_2)-CH_2-SiH_3)_3$, $N(Si(H)(NiBu_2)-CH_2-SiH_3)_3$, $N(Si(H)(NtBu_2)-CH_2-SiH_3)_3$, $N(Si(H)(NHtBu)-CH_2-SiH_3)_3$, $N(Si(H)(NAm_2)-CH_2-SiH_3)_3$, $N(Si(H)(NHAm)-CH_2-SiH_3)_3$, $N(Si(H)(NCyPentyl_2)-CH_2-SiH_3)_3$, $N(Si(H)(Nhexyl_2)-CH_2-SiH_3)_3$, $N(Si(H)(NCyHex_2)-CH_2-SiH_3)_3$, $N(Si(H)(NMeH)-CH_2-SiH_3)_3$, $N(Si(H)(NEtH)-CH_2-SiH_3)_3$, $N(Si(H)(NnPrH)-CH_2-SiH_3)_3$, $N(Si(H)(NiPrH)-CH_2-SiH_3)_3$, $N(Si(H)(NBuH)-CH_2-SiH_3)_3$, $N(Si(H)(NtBuH)-CH_2-SiH_3)_3$, $N(Si(H)(pyridine)-CH_2-SiH_3)_3$, $N(Si(H)(pyrole)-CH_2-SiH_3)_3$, $N(Si(H)(pyrrolidine)-CH_2-SiH_3)_3$, $N(Si(H)(imidazole)-CH_2-SiH_3)_3$, $N(Si(H)(OH)-CH_2-SiH_3)_3$, $N(Si(H)(OMe)-CH_2-SiH_3)_3$, $N(Si(H)(OEt)-CH_2-SiH_3)_3$, $N(Si(H)(OnPr)-CH_2-SiH_3)_3$, $N(Si(H)(OiPr)-CH_2-SiH_3)_3$, $N(Si(H)(OBu)-CH_2-SiH_3)_3$, $N(Si(H)(OiBu)-CH_2-SiH_3)_3$, $N(Si(H)(OtBu)-CH_2-SiH_3)_3$, $N(Si(H)(OAm)-CH_2-SiH_3)_3$, and $N(Si(H)(OHexyl)-CH_2-SiH_3)_3$.

The disclosed carbosilane substituted amine precursor may also include mixed carbosilane ligands, such as, $N(Si(H)(Cl)-CH_2-SiH_3)_2(SiH_2-CH_2SiH_3)$, $N(Si(H)(Br)-CH_2-SiH_3)_2(SiH_2-CH_2SiH_3)$, $N(Si(H)(I)-CH_2-SiH_3)_2(SiH_2-CH_2SiH_3)$, $N(Si(H)(NH_2)-CH_2-SiH_3)_2(SiH_2-CH_2SiH_3)$, $N(Si(H)(NMe_2)-CH_2-SiH_3)_2(SiH_2-CH_2SiH_3)$, $N(Si(H)(NMeEt)-CH_2-SiH_3)_2(SiH_2-CH_2SiH_3)$, $N(Si(H)(NEt_2)-CH_2-SiH_3)_2(SiH_2-CH_2SiH_3)$, $N(Si(H)(NnPr_2)-CH_2-SiH_3)_2(SiH_2-CH_2SiH_3)$, $N(Si(H)

(NiPr$_2$)—CH$_2$—SiH$_3$)$_2$(SiH$_2$—CH$_2$SiH$_3$), N(Si(H)(NBu$_2$)-CH$_2$—SiH$_3$)$_2$(SiH$_2$—CH$_2$SiH$_3$), N(Si(H)(NiBu$_2$)-CH$_2$—SiH$_3$)$_2$(SiH$_2$—CH$_2$SiH$_3$), N(Si(H)(NtBu$_2$)-CH$_2$—SiH$_3$)$_2$(SiH$_2$—CH$_2$SiH$_3$), N(Si(H)(NHtBu)-CH$_2$—SiH$_3$)$_2$(SiH$_2$—CH$_2$SiH$_3$), N(Si(H)(NAm$_2$)—CH$_2$—SiH$_3$)$_2$(SiH$_2$—CH$_2$SiH$_3$), N(Si(H)(NHAm)—CH$_2$—SiH$_3$)$_2$(SiH$_2$—CH$_2$SiH$_3$), N(Si(H)(NCyPentyl$_2$)-CH$_2$—SiH$_3$)$_2$(SiH$_2$—CH$_2$SiH$_3$), N(Si(H)(Nhexyl$_2$)-CH$_2$—SiH$_3$)$_2$(SiH$_2$—CH$_2$SiH$_3$), N(Si(H)(NCyHex$_2$)-CH$_2$—SiH$_3$)$_2$(SiH$_2$—CH$_2$SiH$_3$), N(Si(H)(NMeH)—CH$_2$—SiH$_3$)$_2$(SiH$_2$—CH$_2$SiH$_3$), N(Si(H)(NEtH)—CH$_2$—SiH$_3$)$_2$(SiH$_2$—CH$_2$SiH$_3$), N(Si(H)(NnPrH)—CH$_2$—SiH$_3$)$_2$(SiH$_2$—CH$_2$SiH$_3$), N(Si(H)(NiPrH)—CH$_2$—SiH$_3$)$_2$(SiH$_2$—CH$_2$SiH$_3$), N(Si(H)(OH)—CH$_2$—SiH$_3$)$_2$(SiH$_2$—CH$_2$SiH$_3$), N(Si(H)(OMe)-CH$_2$—SiH$_3$)$_2$(SiH$_2$—CH$_2$SiH$_3$), N(Si(H)(OEt)-CH$_2$—SiH$_3$)$_2$(SiH$_2$—CH$_2$SiH$_3$), N(Si(H)(OnPr)—CH$_2$—SiH$_3$)$_2$(SiH$_2$—CH$_2$SiH$_3$), N(Si(H)(OiPr)—CH$_2$—SiH$_3$)$_2$(SiH$_2$—CH$_2$SiH$_3$), N(Si(H)(OBu)-CH$_2$—SiH$_3$)$_2$(SiH$_2$—CH$_2$SiH$_3$), N(Si(H)(OiBu)-CH$_2$—SiH$_3$)$_2$(SiH$_2$—CH$_2$SiH$_3$), N(Si(H)(OtBu)-CH$_2$—SiH$_3$)$_2$(SiH$_2$—CH$_2$SiH$_3$), N(Si(H)(OAm)—CH$_2$—SiH$_3$)$_2$(SiH$_2$—CH$_2$SiH$_3$), N(Si(H)(OHexyl)-CH$_2$—SiH$_3$)$_2$(SiH$_2$—CH$_2$SiH$_3$), N(Si(H)(Cl)—CH$_2$—SiH$_3$)(SiH$_2$—CH$_2$SiH$_3$)$_2$, N(Si(H)(Br)—CH$_2$—SiH$_3$)(SiH$_2$—CH$_2$SiH$_3$)$_2$, N(Si(H)(I)—CH$_2$—SiH$_3$)(SiH$_2$—CH$_2$SiH$_3$)$_2$, N(Si(H)(NH$_2$)—CH$_2$—SiH$_3$)(SiH$_2$—CH$_2$SiH$_3$)$_2$, N(Si(H)(NMe$_2$)-CH$_2$—SiH$_3$)(SiH$_2$—CH$_2$SiH$_3$)$_2$, N(Si(H)(NMeEt)-CH$_2$—SiH$_3$)(SiH$_2$—CH$_2$SiH$_3$)$_2$, N(Si(H)(NEt$_2$)-CH$_2$—SiH$_3$)(SiH$_2$—CH$_2$SiH$_3$)$_2$, N(Si(H)(NnPr$_2$)—CH$_2$—SiH$_3$)(SiH$_2$—CH$_2$SiH$_3$)$_2$, N(Si(H)(NiPr$_2$)—CH$_2$—SiH$_3$)(SiH$_2$—CH$_2$SiH$_3$)$_2$, N(Si(H)(NBu$_2$)-CH$_2$—SiH$_3$)(SiH$_2$—CH$_2$SiH$_3$)$_2$, N(Si(H)(NiBu$_2$)-CH$_2$—SiH$_3$)(SiH$_2$—CH$_2$SiH$_3$)$_2$, N(Si(H)(NtBu$_2$)-CH$_2$—SiH$_3$)(SiH$_2$—CH$_2$SiH$_3$)$_2$, N(Si(H)(NHtBu)-CH$_2$—SiH$_3$)(SiH$_2$—CH$_2$SiH$_3$)$_2$, N(Si(H)(NAm$_2$)—CH$_2$—SiH$_3$)(SiH$_2$—CH$_2$SiH$_3$)$_2$, N(Si(H)(NHAm)—CH$_2$—SiH$_3$)(SiH$_2$—CH$_2$SiH$_3$)$_2$, N(Si(H)(NCyPentyl$_2$)-CH$_2$—SiH$_3$)(SiH$_2$—CH$_2$SiH$_3$)$_2$, N(Si(H)(Nhexyl$_2$)-CH$_2$—SiH$_3$)(SiH$_2$—CH$_2$SiH$_3$)$_2$, N(Si(H)(NCyHex$_2$)-CH$_2$—SiH$_3$)(SiH$_2$—CH$_2$SiH$_3$)$_2$, N(Si(H)(NMeH)—CH$_2$—SiH$_3$)(SiH$_2$—CH$_2$SiH$_3$)$_2$, N(Si(H)(NEtH)—CH$_2$—SiH$_3$)(SiH$_2$—CH$_2$SiH$_3$)$_2$, N(Si(H)(NnPrH)—CH$_2$—SiH$_3$)(SiH$_2$—CH$_2$SiH$_3$)$_2$, N(Si(H)(NiPrH)—CH$_2$—SiH$_3$)(SiH$_2$—CH$_2$SiH$_3$)$_2$, N(Si(H)(OH)—CH$_2$—SiH$_3$)(SiH$_2$—CH$_2$SiH$_3$)$_2$, N(Si(H)(OMe)-CH$_2$—SiH$_3$)(SiH$_2$—CH$_2$SiH$_3$)$_2$, N(Si(H)(OEt)-CH$_2$—SiH$_3$)(SiH$_2$—CH$_2$SiH$_3$)$_2$, N(Si(H)(OnPr)—CH$_2$—SiH$_3$)(SiH$_2$—CH$_2$SiH$_3$)$_2$, N(Si(H)(OiPr)—CH$_2$—SiH$_3$)(SiH$_2$—CH$_2$SiH$_3$)$_2$, N(Si(H)(OBu)-CH$_2$—SiH$_3$)(SiH$_2$—CH$_2$SiH$_3$)$_2$, N(Si(H)(OiBu)-CH$_2$—SiH$_3$)(SiH$_2$—CH$_2$SiH$_3$)$_2$, N(Si(H)(OtBu)-CH$_2$—SiH$_3$)(SiH$_2$—CH$_2$SiH$_3$)$_2$, N(Si(H)(OAm)—CH$_2$—SiH$_3$)(SiH$_2$—CH$_2$SiH$_3$)$_2$, N(Si(H)(OHexyl)-CH$_2$—SiH$_3$)(SiH$_2$—CH$_2$SiH$_3$)$_2$, N(SiH$_2$—CH$_2$—SiH$_2$(Cl))$_2$(SiH$_2$—CH$_2$SiH$_3$), N(SiH$_2$—CH$_2$—SiH$_2$(Br))$_2$(SiH$_2$—CH$_2$SiH$_3$), N(SiH$_2$—CH$_2$—SiH$_2$(I))$_2$(SiH$_2$—CH$_2$SiH$_3$), N(SiH$_2$—CH$_2$—SiH$_2$(NH$_2$))$_2$(SiH$_2$—CH$_2$SiH$_3$), N(SiH$_2$—CH$_2$—SiH$_2$(NMe$_2$))$_2$(SiH$_2$—CH$_2$SiH$_3$), N(SiH$_2$—CH$_2$—SiH$_2$(NMeEt))$_2$(SiH$_2$—CH$_2$SiH$_3$), N(SiH$_2$—CH$_2$—SiH$_2$(NEt$_2$))$_2$(SiH$_2$—CH$_2$SiH$_3$), N(SiH$_2$—CH$_2$—SiH$_2$(NnPr$_2$))$_2$(SiH$_2$—CH$_2$SiH$_3$), N(SiH$_2$—CH$_2$—SiH$_2$(NiPr$_2$))$_2$(SiH$_2$—CH$_2$SiH$_3$), N(SiH$_2$—CH$_2$—SiH$_2$(NBu$_2$))$_2$(SiH$_2$—CH$_2$SiH$_3$), N(SiH$_2$—CH$_2$—SiH$_2$(NiBu$_2$))$_2$(SiH$_2$—CH$_2$SiH$_3$), N(SiH$_2$—CH$_2$—SiH$_2$(NtBu$_2$))$_2$(SiH$_2$—CH$_2$SiH$_3$), N(SiH$_2$—CH$_2$—SiH$_2$(NHtBu))$_2$(SiH$_2$—CH$_2$SiH$_3$), N(SiH$_2$—CH$_2$—SiH$_2$(NAm$_2$))$_2$(SiH$_2$—CH$_2$SiH$_3$), N(SiH$_2$—CH$_2$—SiH$_2$(NHAm))$_2$(SiH$_2$—CH$_2$SiH$_3$), N(SiH$_2$—CH$_2$—SiH$_2$(NCyPentyl$_2$))$_2$(SiH$_2$—CH$_2$SiH$_3$), N(SiH$_2$—CH$_2$—SiH$_2$(Nhexyl$_2$))$_2$(SiH$_2$—CH$_2$SiH$_3$), N(SiH$_2$—CH$_2$—SiH$_2$(NCyHex$_2$))$_2$(SiH$_2$—CH$_2$SiH$_3$), N(SiH$_2$—CH$_2$—SiH$_2$(NMeH))$_2$(SiH$_2$—CH$_2$SiH$_3$), N(SiH$_2$—CH$_2$—SiH$_2$(NEtH))$_2$(SiH$_2$—CH$_2$SiH$_3$), N(SiH$_2$—CH$_2$—SiH$_2$(NnPrH))$_2$(SiH$_2$—CH$_2$SiH$_3$), N(SiH$_2$—CH$_2$—SiH$_2$(NiPrH))$_2$(SiH$_2$—CH$_2$SiH$_3$), N(SiH$_2$—CH$_2$—SiH$_2$(OH))$_2$(SiH$_2$—CH$_2$SiH$_3$), N(SiH$_2$—CH$_2$—SiH$_2$(OMe))$_2$(SiH$_2$—CH$_2$SiH$_3$), N(SiH$_2$—CH$_2$—SiH$_2$(OEt))$_2$(SiH$_2$—CH$_2$SiH$_3$), N(SiH$_2$—CH$_2$—SiH$_2$(OnPr))$_2$(SiH$_2$—CH$_2$SiH$_3$), N(SiH$_2$—CH$_2$—SiH$_2$(OiPr))$_2$(SiH$_2$—CH$_2$SiH$_3$), N(SiH$_2$—CH$_2$—SiH$_2$(OBu))$_2$(SiH$_2$—CH$_2$SiH$_3$), N(SiH$_2$—CH$_2$—SiH$_2$(OiBu))$_2$(SiH$_2$—CH$_2$SiH$_3$), N(SiH$_2$—CH$_2$—SiH$_2$(OtBu))$_2$(SiH$_2$—CH$_2$SiH$_3$), N(SiH$_2$—CH$_2$—SiH$_2$(OAm))$_2$(SiH$_2$—CH$_2$SiH$_3$), N(SiH$_2$—CH$_2$—SiH$_2$(OHexyl))$_2$(SiH$_2$—CH$_2$SiH$_3$), N(SiH$_2$—CH$_2$—SiH$_2$(Cl))(SiH$_2$—CH$_2$SiH$_3$)$_2$, N(SiH$_2$—CH$_2$—SiH$_2$(Br))(SiH$_2$—CH$_2$SiH$_3$)$_2$, N(SiH$_2$—CH$_2$—SiH$_2$(I))(SiH$_2$—CH$_2$SiH$_3$)$_2$, N(SiH$_2$—CH$_2$—SiH$_2$(NH$_2$))(SiH$_2$—CH$_2$SiH$_3$)$_2$, N(SiH$_2$—CH$_2$—SiH$_2$(NMe$_2$))(SiH$_2$—CH$_2$SiH$_3$)$_2$, N(SiH$_2$—CH$_2$—SiH$_2$(NMeEt))(SiH$_2$—CH$_2$SiH$_3$)$_2$, N(SiH$_2$—CH$_2$—SiH$_2$(NEt$_2$))(SiH$_2$—CH$_2$SiH$_3$)$_2$, N(SiH$_2$—CH$_2$—SiH$_2$(NnPr$_2$))(SiH$_2$—CH$_2$SiH$_3$)$_2$, N(SiH$_2$—CH$_2$—SiH$_2$(NiPr$_2$))(SiH$_2$—CH$_2$SiH$_3$)$_2$, N(SiH$_2$—CH$_2$—SiH$_2$(NBu$_2$))(SiH$_2$—CH$_2$SiH$_3$)$_2$, N(SiH$_2$—CH$_2$—SiH$_2$(NiBu$_2$))(SiH$_2$—CH$_2$SiH$_3$)$_2$, N(SiH$_2$—CH$_2$—SiH$_2$(NtBu$_2$))(SiH$_2$—CH$_2$SiH$_3$)$_2$, N(SiH$_2$—CH$_2$—SiH$_2$(NHtBu))(SiH$_2$—CH$_2$SiH$_3$)$_2$, N(SiH$_2$—CH$_2$—SiH$_2$(NAm$_2$))(SiH$_2$—CH$_2$SiH$_3$)$_2$, N(SiH$_2$—CH$_2$—SiH$_2$(NHAm))(SiH$_2$—CH$_2$SiH$_3$)$_2$, N(SiH$_2$—CH$_2$—SiH$_2$(NCyPentyl$_2$))(SiH$_2$—CH$_2$SiH$_3$)$_2$, N(SiH$_2$—CH$_2$—SiH$_2$(Nhexyl$_2$))(SiH$_2$—CH$_2$SiH$_3$)$_2$, N(SiH$_2$—CH$_2$—SiH$_2$(NCyHex$_2$))(SiH$_2$—CH$_2$SiH$_3$)$_2$, N(SiH$_2$—CH$_2$—SiH$_2$(NMeH))(SiH$_2$—CH$_2$SiH$_3$)$_2$, N(SiH$_2$—CH$_2$—SiH$_2$(NEtH))(SiH$_2$—CH$_2$SiH$_3$)$_2$, N(SiH$_2$—CH$_2$—SiH$_2$(NnPrH))(SiH$_2$—CH$_2$SiH$_3$)$_2$, N(SiH$_2$—CH$_2$—SiH$_2$(NiPrH))(SiH$_2$—CH$_2$SiH$_3$)$_2$, N(SiH$_2$—CH$_2$—SiH$_2$(OH))(SiH$_2$—CH$_2$SiH$_3$)$_2$, N(SiH$_2$—CH$_2$—SiH$_2$(OMe))(SiH$_2$—CH$_2$SiH$_3$)$_2$, N(SiH$_2$—CH$_2$—SiH$_2$(OEt))(SiH$_2$—CH$_2$SiH$_3$)$_2$, N(SiH$_2$—CH$_2$—SiH$_2$(OnPr))(SiH$_2$—CH$_2$SiH$_3$)$_2$, N(SiH$_2$—CH$_2$—SiH$_2$(OiPr))(SiH$_2$—CH$_2$SiH$_3$)$_2$, N(SiH$_2$—CH$_2$—SiH$_2$(OBu))(SiH$_2$—CH$_2$SiH$_3$)$_2$, N(SiH$_2$—CH$_2$—SiH$_2$(OiBu))(SiH$_2$—CH$_2$SiH$_3$)$_2$, N(SiH$_2$—CH$_2$—SiH$_2$(OtBu))(SiH$_2$—CH$_2$SiH$_3$)$_2$, N(SiH$_2$—CH$_2$—SiH$_2$(OAm))(SiH$_2$—CH$_2$SiH$_3$)$_2$, and N(SiH$_2$—CH$_2$—SiH$_2$(OHexyl))(SiH$_2$—CH$_2$SiH$_3$)$_2$. The disclosed mixed ligand tris(1,3-disilapropane)amine precursors may provide the desired combination of reactivity and minimized film contamination.

The tris(1,3-disilapropane)amine precursors [N(—SiHR$^2$—CH$_2$—SiH$_2$R$^3$)$_3$] may be synthesized at temperatures from −78° C. to 20° C. by mixing or dissolving 1-halo-1,3-disilapropane, 1,1-dihalo-1,3-disilapropane or 1,3-dihalo-1,3-disilapropane in a non-polar solvent. 1-halo-1,3-disilapropane may be synthesized as described in J. Organomet. Chem. 92, 1975 163-168. 1,1-dihalo-1,3-disilapropane or 1,3-dihalo-1,3-disilapropane may be synthesized according to the same method by changing the stoichiometry of the reagents. Ammonia is slowly added to the mixture or bubbled into the solution to form the N(—SiHR$^2$—CH$_2$—SiH$_2$R$^3$)$_3$ compound, wherein each R$^2$ and R$^3$ is independently H or a halogen (Cl, Br or I).

In another alternative, the N(—SiHR$^2$—CH$_2$—SiH$_2$R$^3$)$_3$ precursors, where each R$^2$ and R$^3$ is independently H or a halogen (Cl, Br or I), may be formed from N(SiH$_2$—CH$_2$—SiH$_3$)$_3$; a disproportionation catalyst, such as nBu$_4$PCl, nBu$_4$NCl, or a weakly basic anion exchange resin containing dialkylamino groups; and the appropriate R$_n$SiX$_{4-n}$ source (wherein n=0-3, R=H or an alkyl group, and X=Cl, Br or I). N(SiH$_2$—CH$_2$—SiH$_3$)$_3$ may be synthesized by reacting NH$_3$ with 1-Cl—SiH$_2$—CH$_2$—SiH$_3$, which may be synthesized according to the method disclosed in J. Organomet. Chem. 92, 1975 163-168.

The halide groups (Cl, Br or I) on the disilapropane chain may then be substituted as necessary. For example, the halide group may be substituted by an amide group by reacting with a primary or secondary amine (NH$_2$R or NHR$_2$) in excess in a non-polar solvent at temperatures (approximately −78° C. to 20° C.), thus producing the desired compound.

Alternatively, the halide group may be substituted by an alkoxy group by reacting with the appropriate alcohol in the presence of a base such as pyridine in a non-polar solvent at low temperatures (approximately −78° C. to 20° C.), thus producing the desired compound.

In another alternative, the halide groups (Cl, Br or I) on the disilapropane chain may be substituted using the appropriate lithium amide. The lithium amide may be formed by combining alkyl lithium with a primary or secondary amine (NH$_2$R or NHR$_2$) in a solvent, such as ether or any other polar solvents, at low temperatures (approximately −78° C. to 20° C.) to form lithium amide. The lithium amide may be isolated and reacted with N(—SiHR$^2$—CH$_2$—SiH$_2$R$^3$), where R$^2$ and R$^3$ are independently H or a halogen (Cl, Br, I) to form the desired compound. Alternatively, the lithium amide solution may be added to N(—SiHR$^2$—CH$_2$—SiH$_2$R$^3$), where R$^2$ and R$^3$ are independently H or a halogen (Cl, Br or I), to form the desired compound.

The reactants are commercially available or may be synthesized according to J. Organomet. Chem. 92, 1975 163-168.

When a=1, the disclosed carbosilane substituted amine precursor has the following formula:

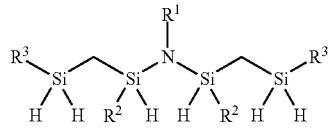

wherein R$^1$ can be H, an alkyl group or a halogen (Cl, Br or I); each R$^2$ and R$^3$ is independently H, a halogen (Cl, Br or I), an alkoxy group (OR') wherein R' is an alkyl group (C1 to C6) or an alkylamino group having the formula NR"$_2$, wherein each R" is independently H, a C1-C6 alkyl group, a C1-C6 alkenyl group, or a C3-C10 aryl or heterocycle group. The R" of the alkylamino group may be joined to form a cyclic chain on the N atom. For example, NR"$_2$ may form pyridine, pyrole, pyrrolidine, or imidazole ring structures.

Exemplary precursors wherein a=1 and R$^1$=H include (H)N(SiH$_2$—CH$_2$SiH$_3$)$_2$, HN(SiH$_2$—CH$_2$—SiH$_2$(Cl))$_2$, HN(SiH$_2$—CH$_2$—SiH$_2$(Br))$_2$, HN(SiH$_2$—CH$_2$—SiH$_2$(I))$_2$, HN(SiH$_2$—CH$_2$—SiH$_2$(NH$_2$))$_2$, HN(SiH$_2$—CH$_2$—SiH$_2$(NMe$_2$))$_2$, HN(SiH$_2$—CH$_2$—SiH$_2$(NMeH))$_2$, HN(SiH$_2$—CH$_2$—SiH$_2$(NEtH))$_2$, HN(SiH$_2$—CH$_2$—SiH$_2$(NMeEt))$_2$, HN(SiH$_2$—CH$_2$—SiH$_2$(NiPrH))$_2$, HN(SiH$_2$—CH$_2$—SiH$_2$(pyridine))$_2$, HN(SiH$_2$—CH$_2$—SiH$_2$(pyrole))$_2$, HN(SiH$_2$—CH$_2$—SiH$_2$(pyrrolidine))$_2$, HN(SiH$_2$—CH$_2$—SiH$_2$(imidazole))$_2$, HN(SiH$_2$—CH$_2$—SiH$_2$(OMe))$_2$, and HN(SiH$_2$—CH$_2$—SiH$_2$(OEt))$_2$. The N—H bond is more reactive than an N-alkyl bond, which may provide improved reactivity with the substrate or co-reactant.

Exemplary precursors wherein a=1 and R$^1$=a halide include (Cl)N(SiH$_2$—CH$_2$SiH$_3$)$_2$, (Cl)N(SiH$_2$—CH$_2$—SiH$_2$(Cl))$_2$, (Cl)N(SiH$_2$—CH$_2$—SiH$_2$(Br))$_2$, (Cl)N(SiH$_2$—CH$_2$—SiH$_2$(I))$_2$, (Cl)N(SiH$_2$—CH$_2$—SiH$_2$(NH$_2$))$_2$, (Cl)N(SiH$_2$—CH$_2$—SiH$_2$(NMe$_2$))$_2$, (Cl)N(SiH$_2$—CH$_2$—SiH$_2$(NMeH))$_2$, (Cl)N(SiH$_2$—CH$_2$—SiH$_2$(NEtH))$_2$, (Cl)N(SiH$_2$—CH$_2$—SiH$_2$(NMeEt))$_2$, (Cl)N(SiH$_2$—CH$_2$—SiH$_2$(NiPrH))$_2$, (Cl)N(SiH$_2$—CH$_2$—SiH$_2$(pyridine))$_2$, (Cl)N(SiH$_2$—CH$_2$—SiH$_2$(pyrole))$_2$, (Cl)N(SiH$_2$—CH$_2$—SiH$_2$(pyrrolidine))$_2$, (Cl)N(SiH$_2$—CH$_2$—SiH$_2$(imidazole))$_2$, (Cl)N(SiH$_2$—CH$_2$—SiH$_2$(OMe))$_2$, (Cl)N(SiH$_2$—CH$_2$—SiH$_2$(OEt))$_2$, (Br)N(SiH$_2$—CH$_2$SiH$_3$)$_2$, (Br)N(SiH$_2$—CH$_2$—SiH$_2$(Cl))$_2$, (Br)N(SiH$_2$—CH$_2$—SiH$_2$(Br))$_2$, (Br)N(SiH$_2$—CH$_2$—SiH$_2$(I))$_2$, (Br)N(SiH$_2$—CH$_2$—SiH$_2$(NH$_2$))$_2$, (Br)N(SiH$_2$—CH$_2$—SiH$_2$(NMe$_2$))$_2$, (Br)N(SiH$_2$—CH$_2$—SiH$_2$(NMeH))$_2$, (Br)N(SiH$_2$—CH$_2$—SiH$_2$(NEtH))$_2$, (Br)N(SiH$_2$—CH$_2$—SiH$_2$(NMeEt))$_2$, (Br)N(SiH$_2$—CH$_2$—SiH$_2$(NiPrH))$_2$, (Br)N(SiH$_2$—CH$_2$—SiH$_2$(pyridine))$_2$, (Br)N(SiH$_2$—CH$_2$—SiH$_2$(pyrole))$_2$, (Br)N(SiH$_2$—CH$_2$—SiH$_2$(pyrrolidine))$_2$, (Br)N(SiH$_2$—CH$_2$—SiH$_2$(imidazole))$_2$, (Br)N(SiH$_2$—CH$_2$—SiH$_2$(OMe))$_2$, (Br)N(SiH$_2$—CH$_2$—SiH$_2$(OEt))$_2$, (I)N(SiH$_2$—CH$_2$SiH$_3$)$_2$, (I)N(SiH$_2$—CH$_2$—SiH$_2$(Cl))$_2$, (I)N(SiH$_2$—CH$_2$—SiH$_2$(Br))$_2$, (I)N(SiH$_2$—CH$_2$—SiH$_2$(I))$_2$, (I)N(SiH$_2$—CH$_2$—SiH$_2$(NH$_2$))$_2$, (I)N(SiH$_2$—CH$_2$—SiH$_2$(NMe$_2$))$_2$, (I)N(SiH$_2$—CH$_2$—SiH$_2$(NMeH))$_2$, (I)N(SiH$_2$—CH$_2$—SiH$_2$(NEtH))$_2$, (I)N(SiH$_2$—CH$_2$—SiH$_2$(NMeEt))$_2$, (I)N(SiH$_2$—CH$_2$—SiH$_2$(NiPrH))$_2$, (I)N(SiH$_2$—CH$_2$—SiH$_2$(pyridine))$_2$, (I)N(SiH$_2$—CH$_2$—SiH$_2$(pyrole))$_2$, (I)N(SiH$_2$—CH$_2$—SiH$_2$(pyrrolidine))$_2$, (I)N(SiH$_2$—CH$_2$—SiH$_2$(imidazole))$_2$, (I)N(SiH$_2$—CH$_2$—SiH$_2$(OMe))$_2$, and (I)N(SiH$_2$—CH$_2$—SiH$_2$(OEt))$_2$. The N—X bond, wherein X is Cl, Br, or I, is more reactive than a N—H or an N-alkyl bond, which may provide improved reactivity with the substrate or co-reactant. It may not be desirable, however, to have any halide contamination in the resulting Si-containing films.

Exemplary precursors wherein a=1, R$^1$=alkyl, and R$^3$=H include, (Me)N(SiH$_2$—CH$_2$SiH$_3$)$_2$, (Et)N(SiH$_2$—CH$_2$SiH$_3$)$_2$, (nPr)N(SiH$_2$—CH$_2$SiH$_3$)$_2$, (iPr)N(SiH$_2$—CH$_2$SiH$_3$)$_2$, (Bu)N(SiH$_2$—CH$_2$SiH$_3$)$_2$, (iBu)N(SiH$_2$—CH$_2$SiH$_3$)$_2$, (tBu)N(SiH$_2$—CH$_2$SiH$_3$)$_2$, (amyl)N(SiH$_2$—CH$_2$SiH$_3$)$_2$, (hexyl)N(SiH$_2$—CH$_2$SiH$_3$)$_2$, (Me)N(Si(H)(Cl)—CH$_2$—SiH$_3$)$_2$, (Et)N(Si(H)(Cl)—CH$_2$—SiH$_3$)$_2$, (nPr)N(Si(H)(Cl)—CH$_2$—SiH$_3$)$_2$, (iPr)N(Si(H)(Cl)—CH$_2$—SiH$_3$)$_2$, (Bu)N(Si(H)(Cl)—CH$_2$—SiH$_3$)$_2$, (iBu)N(Si(H)(Cl)—CH$_2$—SiH$_3$)$_2$, (tBu)N(Si(H)(Cl)—CH$_2$—SiH$_3$)$_2$, (amyl)N(Si(H)(Cl)—CH$_2$—SiH$_3$)$_2$, (hexyl)N(Si(H)(Cl)—CH$_2$—SiH$_3$)$_2$, (Me)N(Si(H)(Br)—CH$_2$—SiH$_3$)$_2$, (Et)N(Si(H)(Br)—CH$_2$—SiH$_3$)$_2$, (nPr)N(Si(H)(Br)—CH$_2$—SiH$_3$)$_2$, (iPr)N(Si(H)(Br)—CH$_2$—SiH$_3$)$_2$, (Bu)N(Si(H)(Br)—CH$_2$—SiH$_3$)$_2$, (iBu)N(Si(H)(Br)—CH$_2$—SiH$_3$)$_2$, (tBu)N(Si(H)(Br)—CH$_2$—SiH$_3$)$_2$, (amyl)N(Si(H)(Br)—CH$_2$—SiH$_3$)$_2$, (hexyl)N(Si(H)(Br)—CH$_2$—SiH$_3$)$_2$, (Me)N(Si(H)(I)—CH$_2$—SiH$_3$)$_2$, (Et)N(Si(H)(I)—CH$_2$—SiH$_3$)$_2$, (nPr)N(Si(H)(I)—CH$_2$—SiH$_3$)$_2$, (iPr)N(Si(H)(I)—CH$_2$—SiH$_3$)$_2$, (Bu)N(Si(H)(I)—CH$_2$—SiH$_3$)$_2$, (iBu)N(Si(H)(I)—CH$_2$—SiH$_3$)$_2$, (tBu)N(Si(H)(I)—CH$_2$—SiH$_3$)$_2$, (amyl)N(Si(H)(I)—CH$_2$—SiH$_3$)$_2$, (hexyl)N(Si(H)(I)—CH$_2$—SiH$_3$)$_2$, (Me)N(Si(H)(NH$_2$)—CH$_2$—SiH$_3$)$_2$, (Et)N(Si(H)(NH$_2$)—CH$_2$—SiH$_3$)$_2$, (nPr)N(Si(H)(NH$_2$)—CH$_2$—SiH$_3$)$_2$, (iPr)N(Si(H)(NH$_2$)—CH$_2$—SiH$_3$)$_2$, (Bu)N(Si(H)(NH$_2$)—CH$_2$—SiH$_3$)$_2$, (iBu)N(Si(H)(NH$_2$)—CH$_2$—SiH$_3$)$_2$, (tBu)N(Si(H)(NH$_2$)—CH$_2$—SiH$_3$)$_2$, (amyl)N(Si(H)(NH$_2$)—CH$_2$—SiH$_3$)$_2$, (hexyl)N(Si(H)(NH$_2$)—CH$_2$—SiH$_3$)$_2$, (Me)N(Si(H)(NMe$_2$)-CH$_2$—SiH$_3$)$_2$, (Et)N(Si(H)(NMe$_2$)-CH$_2$—SiH$_3$)$_2$, (nPr)N(Si(H)(NMe$_2$)-CH$_2$—SiH$_3$)$_2$, (iPr)N(Si(H)(NMe$_2$)-CH$_2$—SiH$_3$)$_2$, (Bu)N(Si(H)(NMe$_2$)-CH$_2$—SiH$_3$)$_2$, (iBu)N (Si(H)(NMe₂)-CH₂—SiH₃)₂, (tBu)N(Si(H)(NMe₂)-CH₂—SiH₃)₂, (amyl)N(Si(H)(NMe₂)-CH₂—SiH₃)₂, (hexyl)N(Si(H)(NMe₂)-CH₂—SiH₃)₂, (Me)N(Si(H)(NMeEt)-CH₂—SiH₃)₂, (Et)N(Si(H)(NMeEt)-CH₂—SiH₃)₂, (nPr)N(Si(H)(NMeEt)-CH₂—SiH₃)₂, (iPr)N(Si(H)(NMeEt)-CH₂—SiH₃)₂, (Bu)N(Si(H)(NMeEt)-CH₂—SiH₃)₂, (iBu)N(Si(H)(NMeEt)-CH₂—SiH₃)₂, (tBu)N(Si(H)(NMeEt)-CH₂—SiH₃)₂, (amyl)N(Si(H)(NMeEt)-CH₂—SiH₃)₂, (hexyl)N(Si(H)(NMeEt)-CH₂—SiH₃)₂, (Me)N(Si(H)(NMeH)—CH₂—SiH₃)₂, (Et)N(Si(H)(NMeH)—CH₂—SiH₃)₂, (nPr)N(Si(H)(NMeH)—CH₂—SiH₃)₂, (iPr)N(Si(H)(NMeH)—CH₂—SiH₃)₂, (Bu)N(Si(H)(NMeH)—CH₂—SiH₃)₂, (iBu)N(Si(H)(NMeH)—CH₂—SiH₃)₂, (tBu)N(Si(H)(NMeH)—CH₂—SiH₃)₂, (amyl)N(Si(H)(NMeH)—CH₂—SiH₃)₂, (hexyl)N(Si(H)(NMeH)—CH₂—SiH₃)₂, (Me)N(Si(H)(NEtH)—CH₂—SiH₃)₂, (Et)N(Si(H)(NEtH)—CH₂—SiH₃)₂, (nPr)N(Si(H)(NEtH)—CH₂—SiH₃)₂, (iPr)N(Si(H)(NEtH)—CH₂—SiH₃)₂, (Bu)N(Si(H)(NEtH)—CH₂—SiH₃)₂, (iBu)N(Si(H)(NEtH)—CH₂—SiH₃)₂, (tBu)N(Si(H)(NEtH)—CH₂—SiH₃)₂, (amyl)N(Si(H)(NEtH)—CH₂—SiH₃)₂, (hexyl)N(Si(H)(NEtH)—CH₂—SiH₃)₂, (Me)N(Si(H)(NiPrH)—CH₂—SiH₃)₂, (Et)N(Si(H)(NiPrH)—CH₂—SiH₃)₂, (nPr)N(Si(H)(NiPrH)—CH₂—SiH₃)₂, (iPr)N(Si(H)(NiPrH)—CH₂—SiH₃)₂, (Bu)N(Si(H)(NiPrH)—CH₂—SiH₃)₂, (iBu)N(Si(H)(NiPrH)—CH₂—SiH₃)₂, (tBu)N(Si(H)(NiPrH)—CH₂—SiH₃)₂, (amyl)N(Si(H)(NiPrH)—CH₂—SiH₃)₂, (hexyl)N(Si(H)(NiPrH)—CH₂—SiH₃)₂, (Me)N(Si(H)(NtBuH)—CH₂—SiH₃)₂, (Et)N(Si(H)(NtBuH)—CH₂—SiH₃)₂, (nPr)N(Si(H)(NtBuH)—CH₂—SiH₃)₂, (iPr)N(Si(H)(NtBuH)—CH₂—SiH₃)₂, (Bu)N(Si(H)(NtBuH)—CH₂—SiH₃)₂, (iBu)N(Si(H)(NtBuH)—CH₂—SiH₃)₂, (tBu)N(Si(H)(NtBuH)—CH₂—SiH₃)₂, (amyl)N(Si(H)(NtBuH)—CH₂—SiH₃)₂, (hexyl)N(Si(H)(NtBuH)—CH₂—SiH₃)₂, (Me)N(Si(H)(OEt)-CH₂—SiH₃)₂, (Et)N(Si(H)(OEt)-CH₂—SiH₃)₂, (nPr)N(Si(H)(OEt)-CH₂—SiH₃)₂, (iPr)N(Si(H)(OEt)-CH₂—SiH₃)₂, (Bu)N(Si(H)(OEt)-CH₂—SiH₃)₂, (iBu)N(Si(H)(OEt)-CH₂—SiH₃)₂, (tBu)N(Si(H)(OEt)-CH₂—SiH₃)₂, (amyl)N(Si(H)(OEt)-CH₂—SiH₃)₂, and (hexyl)N(Si(H)(OEt)-CH₂—SiH₃)₂. The R¹ group being an alkyl may be desired to incorporate some carbon in the resulting Si-containing film.

Exemplary precursors wherein a=1, R¹=alkyl, and R²=H include (Me)N(SiH₂—CH₂—SiH₂(Cl))₂, (Et)N(SiH₂—CH₂—SiH₂(Cl))₂, (nPr)N(SiH₂—CH₂—SiH₂(Cl))₂, (iPr)N(SiH₂—CH₂—SiH₂(Cl))₂, (Bu)N(SiH₂—CH₂—SiH₂(Cl))₂, (iBu)N(SiH₂—CH₂—SiH₂(Cl))₂, (tBu)N(SiH₂—CH₂—SiH₂(Cl))₂, (amyl)N(SiH₂—CH₂—SiH₂(Cl))₂, (hexyl)N(SiH₂—CH₂—SiH₂(Cl))₂, (Me)N(SiH₂—CH₂—SiH₂(Br))₂, (Et)N(SiH₂—CH₂—SiH₂(Br))₂, (nPr)N(SiH₂—CH₂—SiH₂(Br))₂, (iPr)N(SiH₂—CH₂—SiH₂(Br))₂, (Bu)N(SiH₂—CH₂—SiH₂(Br))₂, (iBu)N(SiH₂—CH₂—SiH₂(Br))₂, (tBu)N(SiH₂—CH₂—SiH₂(Br))₂, (amyl)N(SiH₂—CH₂—SiH₂(Br))₂, (hexyl)N(SiH₂—CH₂—SiH₂(Br))₂, (Me)N(SiH₂—CH₂—SiH₂(I))₂, (Et)N(SiH₂—CH₂—SiH₂(I))₂, (nPr)N(SiH₂—CH₂—SiH₂(I))₂, (iPr)N(SiH₂—CH₂—SiH₂(I))₂, (Bu)N(SiH₂—CH₂—SiH₂(I))₂, (iBu)N(SiH₂—CH₂—SiH₂(I))₂, (tBu)N(SiH₂—CH₂—SiH₂(I))₂, (amyl)N(SiH₂—CH₂—SiH₂(I))₂, (hexyl)N(SiH₂—CH₂—SiH₂(I))₂, (Me)N(SiH₂—CH₂—SiH₂(NH₂))₂, (Et)N(SiH₂—CH₂—SiH₂(NH₂))₂, (nPr)N(SiH₂—CH₂—SiH₂(NH₂))₂, (iPr)N(SiH₂—CH₂—SiH₂(NH₂))₂, (Bu)N(SiH₂—CH₂—SiH₂(NH₂))₂, (iBu)N(SiH₂—CH₂—SiH₂(NH₂))₂, (tBu)N(SiH₂—CH₂—SiH₂(NH₂))₂, (amyl)N(SiH₂—CH₂—SiH₂(NH₂))₂, (hexyl)N(SiH₂—CH₂—SiH₂(NH₂))₂, (Me)N(SiH₂—CH₂—SiH₂(NMe₂))₂, (Et)N(SiH₂—CH₂—SiH₂(NMe₂))₂, (nPr)N(SiH₂—CH₂—SiH₂(NMe₂))₂, (iPr)N(SiH₂—CH₂—SiH₂(NMe₂))₂, (Bu)N(SiH₂—CH₂—SiH₂(NMe₂))₂, (iBu)N(SiH₂—CH₂—SiH₂(NMe₂))₂, (tBu)N(SiH₂—CH₂—SiH₂(NMe₂))₂, (amyl)N(SiH₂—CH₂—SiH₂(NMe₂))₂, (hexyl)N(SiH₂—CH₂—SiH₂(NMe₂))₂, (Me)N(SiH₂—CH₂—SiH₂(NMeH))₂, (Et)N(SiH₂—CH₂—SiH₂(NMeH))₂, (nPr)N(SiH₂—CH₂—SiH₂(NMeH))₂, (iPr)N(SiH₂—CH₂—SiH₂(NMeH))₂, (Bu)N(SiH₂—CH₂—SiH₂(NMeH))₂, (iBu)N(SiH₂—CH₂—SiH₂(NMeH))₂, (tBu)N(SiH₂—CH₂—SiH₂(NMeH))₂, (amyl)N(SiH₂—CH₂—SiH₂(NMeH))₂, (hexyl)N(SiH₂—CH₂—SiH₂(NMeH))₂, (Me)N(SiH₂—CH₂—SiH₂(NMeEt))₂, (Et)N(SiH₂—CH₂—SiH₂(NMeEt))₂, (nPr)N(SiH₂—CH₂—SiH₂(NMeEt))₂, (iPr)N(SiH₂—CH₂—SiH₂(NMeEt))₂, (Bu)N(SiH₂—CH₂—SiH₂(NMeEt))₂, (iBu)N(SiH₂—CH₂—SiH₂(NMeEt))₂, (tBu)N(SiH₂—CH₂—SiH₂(NMeEt))₂, (amyl)N(SiH₂—CH₂—SiH₂(NMeEt))₂, (hexyl)N(SiH₂—CH₂—SiH₂(NMeEt))₂, (Me)N(SiH₂—CH₂—SiH₂(NEtH))₂, (Et)N(SiH₂—CH₂—SiH₂(NEtH))₂, (nPr)N(SiH₂—CH₂—SiH₂(NEtH))₂, (iPr)N(SiH₂—CH₂—SiH₂(NEtH))₂, (Bu)N(SiH₂—CH₂—SiH₂(NEtH))₂, (iBu)N(SiH₂—CH₂—SiH₂(NEtH))₂, (tBu)N(SiH₂—CH₂—SiH₂(NEtH))₂, (amyl)N(SiH₂—CH₂—SiH₂(NEtH))₂, (hexyl)N(SiH₂—CH₂—SiH₂(NEtH))₂, (Me)N(SiH₂—CH₂—SiH₂(NiPrH))₂, (Et)N(SiH₂—CH₂—SiH₂(NiPrH))₂, (nPr)N(SiH₂—CH₂—SiH₂(NiPrH))₂, (iPr)N(SiH₂—CH₂—SiH₂(NiPrH))₂, (Bu)N(SiH₂—CH₂—SiH₂(NiPrH))₂, (iBu)N(SiH₂—CH₂—SiH₂(NiPrH))₂, (tBu)N(SiH₂—CH₂—SiH₂(NiPrH))₂, (amyl)N(SiH₂—CH₂—SiH₂(NiPrH))₂, (hexyl)N(SiH₂—CH₂—SiH₂(NiPrH))₂, (Me)N(SiH₂—CH₂—SiH₂(pyridine))₂, (Et)N(SiH₂—CH₂—SiH₂(pyridine))₂, (nPr)N(SiH₂—CH₂—SiH₂(pyridine))₂, (iPr)N(SiH₂—CH₂—SiH₂(pyridine))₂, (Bu)N(SiH₂—CH₂—SiH₂(pyridine))₂, (iBu)N(SiH₂—CH₂—SiH₂(pyridine))₂, (tBu)N(SiH₂—CH₂—SiH₂(pyridine))₂, (amyl)N(SiH₂—CH₂—SiH₂(pyridine))₂, (hexyl)N(SiH₂—CH₂—SiH₂(pyridine))₂, (Me)N(SiH₂—CH₂—SiH₂(pyrole))₂, (Et)N(SiH₂—CH₂—SiH₂(pyrole))₂, (nPr)N(SiH₂—CH₂—SiH₂(pyrole))₂, (iPr)N(SiH₂—CH₂—SiH₂(pyrole))₂, (Bu)N(SiH₂—CH₂—SiH₂(pyrole))₂, (iBu)N(SiH₂—CH₂—SiH₂(pyrole))₂, (tBu)N(SiH₂—CH₂—SiH₂(pyrole))₂, (amyl)N(SiH₂—CH₂—SiH₂(pyrole))₂, (hexyl)N(SiH₂—CH₂—SiH₂(pyrole))₂, (Me)N(SiH₂—CH₂—SiH₂(pyrrolidine))₂, (Et)N(SiH₂—CH₂—SiH₂(pyrrolidine))₂, (nPr)N(SiH₂—CH₂—SiH₂(pyrrolidine))₂, (iPr)N(SiH₂—CH₂—SiH₂(pyrrolidine))₂, (Bu)N(SiH₂—CH₂—SiH₂(pyrrolidine))₂, (iBu)N(SiH₂—CH₂—SiH₂(pyrrolidine))₂, (tBu)N(SiH₂—CH₂—SiH₂(pyrrolidine))₂, (amyl)N(SiH₂—CH₂—SiH₂(pyrrolidine))₂, (hexyl)N(SiH₂—CH₂—SiH₂(pyrrolidine))₂, (Me)N(SiH₂—CH₂—SiH₂(imidazole))₂, (Et)N(SiH₂—CH₂—SiH₂(imidazole))₂, (nPr)N(SiH₂—CH₂—SiH₂(imidazole))₂, (iPr)N(SiH₂—CH₂—SiH₂(imidazole))₂, (Bu)N(SiH₂—CH₂—SiH₂(imidazole))₂, (iBu)N(SiH₂—CH₂—SiH₂(imidazole))₂, (tBu)N(SiH₂—CH₂—SiH₂(imidazole))₂, (amyl)N(SiH₂—CH₂—SiH₂(imidazole))₂, (hexyl)N(SiH₂—CH₂—SiH₂(imidazole))₂, (Me)N(SiH₂—CH₂—SiH₂(OMe))₂, (Et)N(SiH₂—CH₂—SiH₂(OMe))₂, (nPr)N(SiH₂—CH₂—SiH₂(OMe))₂, (iPr)N(SiH₂—CH₂—SiH₂(OMe))₂, (Bu)N(SiH₂—CH₂—SiH₂(OMe))₂, (iBu)N(SiH₂—CH₂—SiH₂(OMe))₂, (tBu)N(SiH₂—CH₂—SiH₂(OMe))₂, (amyl)N(SiH₂—CH₂—SiH₂(OMe))₂, (hexyl)N(SiH₂—CH₂—SiH₂(OMe))₂, (Me)N(SiH₂—CH₂—SiH₂(OEt))₂, (Et)N(SiH₂—CH₂—SiH₂(OEt))₂, (nPr)N(SiH₂—CH₂—SiH₂(OEt))₂, (iPr)N(SiH₂—CH₂—SiH₂(OEt))₂, (Bu)N(SiH₂—CH₂—SiH₂(OEt))₂, (iBu)N(SiH₂—CH₂—SiH₂(OEt))₂, (tBu)N(SiH₂—CH₂—SiH₂(OEt))₂, (amyl)N(SiH₂—CH₂—SiH₂(OEt))₂, and (hexyl)N(SiH₂—CH₂—SiH₂(OEt))₂.

The disclosed carbosilane substituted amine precursor may also include mixed carbosilane ligands, such as, HN(Si(H)(Cl)—CH₂—SiH₃)(SiH₂—CH₂SiH₃), MeN(Si(H)

(Cl)—CH$_2$—SiH$_3$)(SiH$_2$—CH$_2$SiH$_3$), EtN(Si(H)(Cl)—CH$_2$—SiH$_3$)(SiH$_2$—CH$_2$SiH$_3$), iPrN(Si(H)(Cl)—CH$_2$—SiH$_3$)(SiH$_2$—CH$_2$SiH$_3$), (Cl)N(Si(H)(Cl)—CH$_2$—SiH$_3$)(SiH$_2$—CH$_2$SiH$_3$), (Br)N(Si(H)(Cl)—CH$_2$—SiH$_3$)(SiH$_2$—CH$_2$SiH$_3$), (I)N(Si(H)(Cl)—CH$_2$—SiH$_3$)(SiH$_2$—CH$_2$SiH$_3$), HN(Si(H)(Br)—CH$_2$—SiH$_3$)(SiH$_2$—CH$_2$SiH$_3$), MeN(Si(H)(Br)—CH$_2$—SiH$_3$)(SiH$_2$—CH$_2$SiH$_3$), EtN(Si(H)(Br)—CH$_2$—SiH$_3$)(SiH$_2$—CH$_2$SiH$_3$), iPrN(Si(H)(Br)—CH$_2$—SiH$_3$)(SiH$_2$—CH$_2$SiH$_3$), (Cl)N(Si(H)(Br)—CH$_2$—SiH$_3$)(SiH$_2$—CH$_2$SiH$_3$), (Br)N(Si(H)(Br)—CH$_2$—SiH$_3$)(SiH$_2$—CH$_2$SiH$_3$), (I)N(Si(H)(Br)—CH$_2$—SiH$_3$)(SiH$_2$—CH$_2$SiH$_3$), HN(Si(H)(I)—CH$_2$—SiH$_3$)(SiH$_2$—CH$_2$SiH$_3$), MeN(Si(H)(I)—CH$_2$—SiH$_3$)(SiH$_2$—CH$_2$SiH$_3$), EtN(Si(H)(I)—CH$_2$—SiH$_3$)(SiH$_2$—CH$_2$SiH$_3$), iPrN(Si(H)(I)—CH$_2$—SiH$_3$)(SiH$_2$—CH$_2$SiH$_3$), (Cl)N(Si(H)(I)—CH$_2$—SiH$_3$)(SiH$_2$—CH$_2$SiH$_3$), (Br)N(Si(H)(I)—CH$_2$—SiH$_3$)(SiH$_2$—CH$_2$SiH$_3$), (I)N(Si(H)(I)—CH$_2$—SiH$_3$)(SiH$_2$—CH$_2$SiH$_3$), HN(Si(H)(NH$_2$)—CH$_2$—SiH$_3$)(SiH$_2$—CH$_2$SiH$_3$), MeN(Si(H)(NH$_2$)—CH$_2$—SiH$_3$)(SiH$_2$—CH$_2$SiH$_3$), EtN(Si(H)(NH$_2$)—CH$_2$—SiH$_3$)(SiH$_2$—CH$_2$SiH$_3$), iPrN(Si(H)(NH$_2$)—CH$_2$—SiH$_3$)(SiH$_2$—CH$_2$SiH$_3$), (Cl)N(Si(H)(NH$_2$)—CH$_2$—SiH$_3$)(SiH$_2$—CH$_2$SiH$_3$), (Br)N(Si(H)(NH$_2$)—CH$_2$—SiH$_3$)(SiH$_2$—CH$_2$SiH$_3$), (I)N(Si(H)(NH$_2$)—CH$_2$—SiH$_3$)(SiH$_2$—CH$_2$SiH$_3$), HN(Si(H)(NMe$_2$)-CH$_2$—SiH$_3$)(SiH$_2$—CH$_2$SiH$_3$), MeN(Si(H)(NMe$_2$)-CH$_2$—SiH$_3$)(SiH$_2$—CH$_2$SiH$_3$), EtN(Si(H)(NMe$_2$)-CH$_2$—SiH$_3$)(SiH$_2$—CH$_2$SiH$_3$), iPrN(Si(H)(NMe$_2$)-CH$_2$—SiH$_3$)(SiH$_2$—CH$_2$SiH$_3$), (Cl)N(Si(H)(NMe$_2$)-CH$_2$—SiH$_3$)(SiH$_2$—CH$_2$SiH$_3$), (Br)N(Si(H)(NMe$_2$)-CH$_2$—SiH$_3$)(SiH$_2$—CH$_2$SiH$_3$), (I)N(Si(H)(NMe$_2$)-CH$_2$—SiH$_3$)(SiH$_2$—CH$_2$SiH$_3$), HN(Si(H)(OMe)-CH$_2$—SiH$_3$)(SiH$_2$—CH$_2$SiH$_3$), MeN(Si(H)(OMe)-CH$_2$—SiH$_3$)(SiH$_2$—CH$_2$SiH$_3$), EtN(Si(H)(OMe)-CH$_2$—SiH$_3$)(SiH$_2$—CH$_2$SiH$_3$), iPrN(Si(H)(OMe)-CH$_2$—SiH$_3$)(SiH$_2$—CH$_2$SiH$_3$), (Cl)N(Si(H)(OMe)-CH$_2$—SiH$_3$)(SiH$_2$—CH$_2$SiH$_3$), (Br)N(Si(H)(OMe)-CH$_2$—SiH$_3$)(SiH$_2$—CH$_2$SiH$_3$), (I)N(Si(H)(OMe)-CH$_2$—SiH$_3$)(SiH$_2$—CH$_2$SiH$_3$), HN(Si(H)(OEt)-CH$_2$—SiH$_3$)(SiH$_2$—CH$_2$SiH$_3$), MeN(Si(H)(OEt)-CH$_2$—SiH$_3$)(SiH$_2$—CH$_2$SiH$_3$), EtN(Si(H)(OEt)-CH$_2$—SiH$_3$)(SiH$_2$—CH$_2$SiH$_3$), iPrN(Si(H)(OEt)-CH$_2$—SiH$_3$)(SiH$_2$—CH$_2$SiH$_3$), (Cl)N(Si(H)(OEt)-CH$_2$—SiH$_3$)(SiH$_2$—CH$_2$SiH$_3$), (Br)N(Si(H)(OEt)-CH$_2$—SiH$_3$)(SiH$_2$—CH$_2$SiH$_3$), or (I)N(Si(H)(OEt)-CH$_2$—SiH$_3$)(SiH$_2$—CH$_2$SiH$_3$), HN(SiH$_2$—CH$_2$—SiH$_2$(Cl))(SiH$_2$—CH$_2$SiH$_3$), MeN(SiH$_2$—CH$_2$—SiH$_2$(Cl))(SiH$_2$—CH$_2$SiH$_3$), EtN(SiH$_2$—CH$_2$—SiH$_2$(Cl))(SiH$_2$—CH$_2$SiH$_3$), iPrN(SiH$_2$—CH$_2$—SiH$_2$(Cl))(SiH$_2$—CH$_2$SiH$_3$), (Cl)N(SiH$_2$—CH$_2$—SiH$_2$(Cl))(SiH$_2$—CH$_2$SiH$_3$), (Br)N(SiH$_2$—CH$_2$—SiH$_2$(Cl))(SiH$_2$—CH$_2$SiH$_3$), (I)N(SiH$_2$—CH$_2$—SiH$_2$(Cl))(SiH$_2$—CH$_2$SiH$_3$), HN(SiH$_2$—CH$_2$—SiH$_2$(Br))(SiH$_2$—CH$_2$SiH$_3$), MeN(SiH$_2$—CH$_2$—SiH$_2$(Br))(SiH$_2$—CH$_2$SiH$_3$), EtN(SiH$_2$—CH$_2$—SiH$_2$(Br))(SiH$_2$—CH$_2$SiH$_3$), iPrN(SiH$_2$—CH$_2$—SiH$_2$(Br))(SiH$_2$—CH$_2$SiH$_3$), (Cl)N(SiH$_2$—CH$_2$—SiH$_2$(Br))(SiH$_2$—CH$_2$SiH$_3$), (Br)N(SiH$_2$—CH$_2$—SiH$_2$(Br))(SiH$_2$—CH$_2$SiH$_3$), (I)N(SiH$_2$—CH$_2$—SiH$_2$(Br))(SiH$_2$—CH$_2$SiH$_3$), HN(SiH$_2$—CH$_2$—SiH$_2$(I))(SiH$_2$—CH$_2$SiH$_3$), MeN(SiH$_2$—CH$_2$—SiH$_2$(I))(SiH$_2$—CH$_2$SiH$_3$), EtN(SiH$_2$—CH$_2$—SiH$_2$(I))(SiH$_2$—CH$_2$SiH$_3$), iPrN(SiH$_2$—CH$_2$—SiH$_2$(I))(SiH$_2$—CH$_2$SiH$_3$), (Cl)N(SiH$_2$—CH$_2$—SiH$_2$(I))(SiH$_2$—CH$_2$SiH$_3$), (Br)N(SiH$_2$—CH$_2$—SiH$_2$(I))(SiH$_2$—CH$_2$SiH$_3$), (I)N(SiH$_2$—CH$_2$—SiH$_2$(I))(SiH$_2$—CH$_2$SiH$_3$), HN(SiH$_2$—CH$_2$—SiH$_2$(NH$_2$))(SiH$_2$—CH$_2$SiH$_3$), MeN(SiH$_2$—CH$_2$—SiH$_2$(NH$_2$))(SiH$_2$—CH$_2$SiH$_3$), EtN(SiH$_2$—CH$_2$—SiH$_2$(NH$_2$))(SiH$_2$—CH$_2$SiH$_3$), iPrN(SiH$_2$—CH$_2$—SiH$_2$(NH$_2$))(SiH$_2$—CH$_2$SiH$_3$), (Cl)N(SiH$_2$—CH$_2$—SiH$_2$(NH$_2$))(SiH$_2$—CH$_2$SiH$_3$), (Br)N(SiH$_2$—CH$_2$—SiH$_2$(NH$_2$))(SiH$_2$—CH$_2$SiH$_3$), (I)N(SiH$_2$—CH$_2$—SiH$_2$(NH$_2$))(SiH$_2$—CH$_2$SiH$_3$), HN(SiH$_2$—CH$_2$—SiH$_2$(NMe$_2$))(SiH$_2$—CH$_2$SiH$_3$), MeN(SiH$_2$—CH$_2$—SiH$_2$(NMe$_2$))(SiH$_2$—CH$_2$SiH$_3$), EtN(SiH$_2$—CH$_2$—SiH$_2$(NMe$_2$))(SiH$_2$—CH$_2$SiH$_3$), iPrN(SiH$_2$—CH$_2$—SiH$_2$(NMe$_2$))(SiH$_2$—CH$_2$SiH$_3$), (Cl)N(SiH$_2$—CH$_2$—SiH$_2$(NMe$_2$))(SiH$_2$—CH$_2$SiH$_3$), (Br)N(SiH$_2$—CH$_2$—SiH$_2$(NMe$_2$))(SiH$_2$—CH$_2$SiH$_3$), (I)N(SiH$_2$—CH$_2$—SiH$_2$(NMe$_2$))(SiH$_2$—CH$_2$SiH$_3$), HN(SiH$_2$—CH$_2$—SiH$_2$(OMe))(SiH$_2$—CH$_2$SiH$_3$), MeN(SiH$_2$—CH$_2$—SiH$_2$(OMe))(SiH$_2$—CH$_2$SiH$_3$), EtN(SiH$_2$—CH$_2$—SiH$_2$(OMe))(SiH$_2$—CH$_2$SiH$_3$), iPrN(SiH$_2$—CH$_2$—SiH$_2$(OMe))(SiH$_2$—CH$_2$SiH$_3$), (Cl)N(SiH$_2$—CH$_2$—SiH$_2$(OMe))(SiH$_2$—CH$_2$SiH$_3$), (BON(SiH$_2$—CH$_2$—SiH$_2$(OMe))(SiH$_2$—CH$_2$SiH$_3$), (I)N(SiH$_2$—CH$_2$—SiH$_2$(OMe))(SiH$_2$—CH$_2$SiH$_3$), HN(SiH$_2$—CH$_2$—SiH$_2$(OEt))(SiH$_2$—CH$_2$SiH$_3$), MeN(SiH$_2$—CH$_2$—SiH$_2$(OEt))(SiH$_2$—CH$_2$SiH$_3$), EtN(SiH$_2$—CH$_2$—SiH$_2$(OEt))(SiH$_2$—CH$_2$SiH$_3$), iPrN(SiH$_2$—CH$_2$—SiH$_2$(OEt))(SiH$_2$—CH$_2$SiH$_3$), (Cl)N(SiH$_2$—CH$_2$—SiH$_2$(OEt))(SiH$_2$—CH$_2$SiH$_3$), (Br)N(SiH$_2$—CH$_2$—SiH$_2$(OEt))(SiH$_2$—CH$_2$SiH$_3$), and (I)N(SiH$_2$—CH$_2$—SiH$_2$(OEt))(SiH$_2$—CH$_2$SiH$_3$). The disclosed mixed ligand bis(1,3-disilapropane)amine precursors may provide the desired combination of reactivity and minimized film contamination.

The bis(1,3-disilapropane) amine precursors (R$^1$N(—SiHR$^2$—CH$_2$—SiH$_2$R$^3$)$_2$) may be synthesized at temperatures (−78° C. to 20° C.) by mixing or dissolving 1-halo-1,3-disilapropane, 1,1-dihalo-1,3-disilapropane or 1,3-dihalo-1,3-disilapropane in a non-polar solvent. 1-halo-1,3-disilapropane may be synthesized as described in J. Organomet. Chem. 92, 1975 163-168. 1,1-dihalo-1,3-disilapropane or 1,3-dihalo-1,3-disilapropane may be synthesized according to the same method by changing the stoichiometry of the reagents. Primary amine (R$^1$NH$_2$) is slowly added to the mixture to form the R$^1$N(—SiHR$^2$—CH$_2$—SiH$_2$R$^3$)$_2$ compound, wherein each R$^2$ and R$^3$ is independently a H or halogen (Cl, Br or I).

Alternatively, the R$^1$N(—SiHR$^2$—CH$_2$—SiH$_2$R$^3$)$_2$ precursors, wherein R$^2$ and R$^3$ is independently a H or halogen (Cl, Br or I), may be formed from R$^1$N(SiH$_2$—CH$_2$—SiH$_3$)$_2$; a disproportionation catalyst, such as nBu$_4$PCl, nBu$_4$NCl, or a weakly basic anion exchange resin containing dialkylamino groups; and the appropriate R$_n$SiX$_{4-n}$ source (wherein n=0-3, R=H or an alkyl group, and X=Cl, Br or I). N(SiH$_2$—CH$_2$—SiH$_3$)$_3$ may be synthesized by reacting NH$_3$ with 1-Cl—SiH$_2$—CH$_2$—SiH$_3$, which may be synthesized according to the method disclosed in J. Organomet. Chem. 92, 1975 163-168.

The halide groups (Cl, Br or I) on the disilapropane chain may then be substituted as necessary.

For example, the halide group may be substituted by an amide group by reacting with a primary or secondary amine (NH$_2$R or NHR$_2$) in excess in a non-polar solvent at temperatures (approximately −78° C. to 20° C.), thus producing the desired compound.

Alternatively, the halide group may be substituted by an alkoxy group by reacting with the appropriate alcohol in the presence of a base such as pyridine in a non-polar solvent at low temperatures (approximately −78° C. to 20° C.), thus producing the desired compound.

In another alternative, the halide groups (Cl, Br or I) may be substituted using the appropriate lithium amide. The lithium amide can be formed by combining alkyl lithium with a primary or secondary amine (NH$_2$R or NHR$_2$) in a solvent, such as ether or any other polar solvents, at temperatures from approximately −78° C. to 20° C. to form lithium amide. The lithium amide may be isolated and reacted with $R^1N(—SiHR^2—CH_2—SiH_2R^3)_2$, where $R^2$ and $R^3$ are independently H or a halogen (Cl, Br, I) to form the desired compound. Alternatively, the lithium amide solution may be added to $R^1N(—SiHR^2—CH_2—SiH_2R^3)_2$, where $R^2$ and $R^3$ are independently H or a halogen (Cl, Br or I) to form the desired compound.

$XN(—SiHR^2—CH_2—SiH_2R^3)_2$ precursors, where X=Cl, Br or I, may be formed from the $HN(—SiHR^2—CH_2—SiH_2R^3)_2$ compounds using known chlorination methods from the literature. For example, but not limited to, reacting $HN(—SiHR^2—CH_2—SiH_2R^3)_2$ with the halogenating agent N-chloro-, bromo-, or iodo-succinimide in toluene for 1 to 12 hours at temperatures ranging from 0° C. to reflux; according to Warren et al., Nature, 508, 2014, 402-405, and references therein.

The reactants are commercially available or may be synthesized according to J. Organomet. Chem. 92, 1975 163-168.

To ensure process reliability, the resulting Si-containing film forming composition may be purified by continuous or fractional batch distillation or sublimation prior to use to a purity ranging from approximately 90% w/w to approximately 100% w/w, preferably ranging from approximately 99% w/w to approximately 100% w/w. The Si-containing film forming compositions may contain any of the following impurities: undesired congeneric species; solvents; chlorinated metal compounds; or other reaction products. Preferably, the total quantity of these impurities is below 0.1% w/w.

The concentration of each of hexane, substituted hexane, pentane, substituted pentane, dimethoxy ether, or anisole in the purified material may range from approximately 0% w/w to approximately 5% w/w, preferably from approximately 0% w/w to approximately 0.1% w/w. Solvents may be used in the composition's synthesis. Separation of the solvents from the composition may be difficult if both have similar boiling points. Cooling the mixture may produce solid precursor in liquid solvent, which may be separated by filtration. Vacuum distillation may also be used, provided the precursor product is not heated above approximately its decomposition point.

In one embodiment the disclosed Si-containing film forming composition contains less than 5% v/v, preferably less than 1% v/v, more preferably less than 0.1% v/v, and even more preferably less than 0.01% v/v of any of its undesired congeneric species, reactants, or other reaction products. This embodiment may provide better process repeatability. This embodiment may be produced by distillation of the Si-containing film forming composition. In an alternate embodiment, the disclosed Si-containing film forming compositions may contain between 5% v/v and 50% v/v of the carbosilane substituted amine precursor, particularly when the mixture provides improved process parameters or isolation of the target precursor is too difficult or expensive. For example, a mixture of reaction products may produce a stable, liquid mixture suitable for spin-on or vapor deposition.

The concentration of trace metals and metalloids in the Si-containing film forming composition may each range from approximately 0 ppb to approximately 100 ppb, and more preferably from approximately 0 ppb to approximately 10 ppb. The concentration of X (wherein X=Cl, Br, I, or F) in the purified Si-containing film forming composition may range from approximately 0 ppm to approximately 100 ppm and more preferably from approximately 0 ppm to approximately 10 ppm.

Also disclosed are methods of using the disclosed carbosilane substituted amine precursors for vapor deposition methods. The disclosed methods provide for the use of the Si-containing film forming composition for deposition of silicon-containing films. The disclosed methods may be useful in the manufacture of semiconductor, photovoltaic, LCD-TFT, or flat panel type devices. The method includes: introducing the vapor of the disclosed Si-containing film forming composition into a reactor having a substrate disposed therein: and depositing at least part of the disclosed carbosilane substituted amine precursor onto the substrate via a deposition process to form a Si-containing layer.

The disclosed methods also provide for forming a bimetal-containing layer on a substrate using a vapor deposition process and, more particularly, for deposition of $SiMO_x$ films, wherein x may be 0-4 and M is Ta, Hf, Nb, Mg, Al, Sr, Y, Ba, Ca, As, Sb, Bi, Sn, Pb, Co, lanthanides (such as Er), or combinations thereof.

The disclosed methods of forming silicon-containing layers on substrates may be useful in the manufacture of semiconductor, photovoltaic, LCD-TFT, or flat panel type devices. The disclosed Si-containing film forming compositions may deposit Si-containing films using any vapor deposition methods known in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LP-CVD), sub-atmospheric CVD (SACVD) or atmospheric pressure CVD (APCVD), flowable CVD (f-CVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably ALD, spatial ALD, or PE-ALD in order to provide suitable step coverage and film thickness control.

The vapor of the Si-containing film forming composition is introduced into a reaction chamber containing a substrate. The temperature and the pressure within the reaction chamber and the temperature of the substrate are held at conditions suitable for vapor deposition of at least part of the carbosilane substituted amine precursor onto the substrate. In other words, after introduction of the vaporized composition into the chamber, conditions within the chamber are such that at least part of the vaporized precursor is deposited onto the substrate to form the silicon-containing film. A co-reactant may also be used to help in formation of the Si-containing layer.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr to about 20 Torr. In addition, the temperature within the reaction chamber may range from about 20° C. to about 600° C. One of ordinary skill in the art will recognize that the temperature may be optimized through mere experimentation to achieve the desired result.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 300° C. to approximately 600° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 150° C. to 600° C. Preferably, the temperature of the substrate remains less than or equal to 500° C.

The type of substrate upon which the silicon-containing film will be deposited will vary depending on the final use intended. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, Ge, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combinations thereof. Additionally, the wafers may include copper layers, tungsten layers or metal layers (e.g. platinum, palladium, nickel, rhodium, or gold). The wafers may include barrier layers, such as manganese, manganese oxide, tantalum, tantalum nitride, etc. Plastic layers, such as poly(3,4-ethylenedioxythiophene)poly (styrenesulfonate) [PEDOT:PSS] may also be used. The layers may be planar or patterned. In some embodiments, the substrate may be a patterned photoresist film made of hydrogenated carbon, for example $CH_x$, wherein x is greater than zero (e.g., x≤4). In some embodiments, the substrate may include layers of oxides which are used as dielectric materials in MIM, DRAM, or FeRam technologies (for example, $ZrO_2$ based materials, $HfO_2$ based materials, $TiO_2$ based materials, rare earth oxide based materials, ternary oxide based materials, etc.) or from nitride-based films (for example, TaN) that are used as an oxygen barrier between copper and the low-k layer. The disclosed processes may deposit the silicon-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. The actual substrate utilized may also depend upon the specific precursor embodiment utilized. In many instances though, the preferred substrate utilized will be selected from hydrogenated carbon, TiN, SRO, Ru, and Si type substrates, such as polysilicon or crystalline silicon substrates.

The substrate may be patterned to include vias or trenches having high aspect ratios. For example, a conformal Si-containing film, such as $SiO_2$, may be deposited using any ALD technique on a through silicon via (TSV) having an aspect ratio ranging from approximately 20:1 to approximately 100:1.

The Si-containing film forming compositions may be supplied either in neat form or in a blend with a solvent suitable for vapor deposition, such as toluene, ethyl benzene, xylene, mesitylene, decane, dodecane, octane, hexane, pentane, tertiary amines, acetone, tetrahydrofuran, ethanol, ethylmethylketone, 1,4-dioxane, or others. Alternatively, the Si-containing film forming composition may comprise a solvent suitable for casting deposition, such as water, ethanol, isopropanol, naphtha, methylisobutylketone (MIBK), n-methylisobutylketon (NMIBK), or combinations thereof. One of ordinary skill in the art will recognize that the casting deposition solution may further comprise pH regulators or surfactants. The disclosed precursors may be present in varying concentrations in the solvent. For example, the resulting concentration of the vapor deposition solution may range from approximately 0.05 M to approximately 2 M. One of ordinary skill in the art will recognize that the molarity of the casting deposition solution is directly proportional to the desired film thickness and may adjust the molarity accordingly.

For vapor deposition, the neat or blended Si-containing film forming compositions are introduced into a reactor in vapor form by conventional means, such as tubing and/or flow meters. The composition in vapor form may be produced by vaporizing the neat or blended composition through a conventional vaporization step such as direct vaporization, distillation, by bubbling, or by using a sublimator such as the one disclosed in PCT Publication WO2009/087609 to Xu et al. The neat or blended composition may be fed in liquid state to a vaporizer where it is vaporized before it is introduced into the reactor. Alternatively, the neat or blended composition may be vaporized by passing a carrier gas into a container containing the precursor or by bubbling the carrier gas into the precursor. The carrier gas may include, but is not limited to, Ar, He, or $N_2$, and mixtures thereof. Bubbling with a carrier gas may also remove any dissolved oxygen present in the neat or blended composition. The carrier gas and precursor are then introduced into the reactor as a vapor.

If necessary, the container may be heated to a temperature that permits the Si-containing film forming composition to be in its liquid phase and to have a sufficient vapor pressure. The container may be maintained at temperatures in the range of, for example, 0-150° C. Those skilled in the art recognize that the temperature of the container may be adjusted in a known manner to control the amount of Si-containing film forming composition vaporized.

In addition to the disclosed composition, a reaction gas may also be introduced into the reactor. The reaction gas may be an oxidizing agent such as one of $O_2$; $O_3$; $H_2O$; $H_2O_2$; oxygen containing radicals such as O. or OH.; NO; $NO_2$; carboxylic acids such as formic acid, acetic acid, propionic acid; radical species of NO, $NO_2$, or the carboxylic acids; para-formaldehyde; and mixtures thereof. Preferably, the oxidizing agent is selected from the group consisting of $O_2$, $O_3$, $H_2O$, $H_2O_2$, oxygen containing radicals thereof such as O. or OH., and mixtures thereof. Preferably, when an ALD process is performed, the co-reactant is plasma treated oxygen, ozone, or combinations thereof. When an oxidizing gas is used, the resulting silicon containing film will also contain oxygen.

Alternatively, the reaction gas may be a reducing agent such as one of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkylsilanes (such as $(CH_3)_2SiH_2$, $(C_2H_5)_2SiH_2$, $(CH_3)SiH_3$, $(C_2H_5)SiH_3$), hydrazines (such as $N_2H_4$, $MeHNNH_2$, MeHNNHMe), organic amines (such as $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$), pyrazoline, pyridine, B-containing molecules (such as $B_2H_6$, 9-borabicyclo[3,3,1]none, trimethylboron, triethylboron, borazine), alkyl metals (such as trimethylaluminum, triethylaluminum, dimethylzinc, diethylzinc), radical species thereof, and mixtures thereof. Preferably, the reducing agent is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof. When a reducing agent is used, the resulting silicon containing film may be pure Si.

The reaction gas may be treated by a plasma, in order to decompose the reaction gas into its radical form. $N_2$ may also be utilized as a reducing agent when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

When the desired silicon-containing film also contains another element, such as, for example and without limitation, Ta, Hf, Nb, Mg, Al, Sr, Y, Ba, Ca, As, Sb, Bi, Sn, Pb, Co, lanthanides (such as Er), or combinations thereof, the co-reactants may include a precursor selected from, but not limited to, alkyls, such as $Ln(RCp)_3$ or $Co(RCp)_2$, amines, such as $Nb(Cp)(NtBu)(NMe_2)_3$ and any combination thereof.

The disclosed Si-containing film forming compositions may also be used with a halosilane or polyhalodisilane or polyhalotrisilane, such as hexachlorodisilane, pentachlorodisilane, or tetrachlorodisilane, or octachlorotrisilane, and one or more co-reactant gases to form SiN or SiCN films, as disclosed in PCT Publication Number WO2011/123792, the entire contents of which are incorporated herein in their entireties.

The Si-containing film forming composition and one or more co-reactants may be introduced into the reaction chamber simultaneously (chemical vapor deposition), sequentially (atomic layer deposition), or in other combinations. For example, the Si-containing film forming composition may be introduced in one pulse and two additional metal sources may be introduced together in a separate pulse [modified atomic layer deposition]. Alternatively, the reaction chamber may already contain the co-reactant prior to introduction of the Si-containing film forming composition. The co-reactant may be passed through a plasma system localized or remotely from the reaction chamber, and decomposed to radicals. Alternatively, the Si-containing film forming composition may be introduced to the reaction chamber continuously while other metal sources are introduced by pulse (pulsed-chemical vapor deposition). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s. In another alternative, the Si-containing film forming composition and one or more co-reactants may be simultaneously sprayed from a shower head under which a susceptor holding several wafers is spun (spatial ALD).

In one non-limiting exemplary atomic layer deposition type process, the vapor phase of the Si-containing film forming composition is introduced into the reaction chamber, where it is contacted with a suitable substrate. Excess composition may then be removed from the reaction chamber by purging and/or evacuating the reaction chamber. An oxygen source is introduced into the reaction chamber where it reacts with the absorbed carbosilane substituted amine precursor in a self-limiting manner. Any excess oxygen source is removed from the reaction chamber by purging and/or evacuating the reaction chamber. If the desired film is a silicon oxide film, this two-step process may provide the desired film thickness or may be repeated until a film having the necessary thickness has been obtained.

Alternatively, if the desired film is a silicon metal/metalloid oxide film (i.e., $SiMO_x$, wherein x may be 0-4 and M is Ta, Hf, Nb, Mg, Al, Sr, Y, Ba, Ca, As, Sb, Bi, Sn, Pb, Co, lanthanides (such as Er), or combinations thereof), the two-step process above may be followed by introduction of a second vapor of a metal- or metalloid-containing precursor into the reaction chamber. The metal- or metalloid-containing precursor will be selected based on the nature of the silicon metal/metalloid oxide film being deposited. After introduction into the reaction chamber, the metal- or metalloid-containing precursor is contacted with the substrate. Any excess metal- or metalloid-containing precursor is removed from the reaction chamber by purging and/or evacuating the reaction chamber. Once again, an oxygen source may be introduced into the reaction chamber to react with the metal- or metalloid-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the Si-containing film forming composition, metal- or metalloid-containing precursor, and oxygen source, a film of desired composition and thickness can be deposited.

Additionally, by varying the number of pulses, films having a desired stoichiometric M:Si ratio may be obtained. For example, a $SiMO_2$ film may be obtained by having one pulse of the Si-containing film forming composition and one pulse of the metal- or metalloid-containing precursor, with each pulse being followed by a pulse of the oxygen source. However, one of ordinary skill in the art will recognize that the number of pulses required to obtain the desired film may not be identical to the stoichiometric ratio of the resulting film.

In another alternative, Si or dense SiCN films may be deposited via an ALD or modified ALD process using the disclosed compositions and a halosilane compound having the formula $Si_aH_{2a+2-b}X_b$, wherein X is F, Cl, Br, or I; $a=1$ through 6; and $b=1$ through $(2a+2)$; or a cyclic halosilane compound having the formula $Si_cH_{2c-d}X_d$—, wherein X is F, Cl, Br, or I; $c=3-8$; and $d=1$ through $2c$. Preferably the halosilane compound is trichlorosilane, hexachlorodisilane (HCDS), pentachlorodisilane (PCDS), tetrachlorodisilane, or hexachlorocyclohexasilane. One of ordinary skill in the art will recognize that the Cl in these compounds may be substituted by Br or I when lower deposition temperatures are necessary, due to the lower bond energy in the Si—X bond (i.e., Si—Cl=456 kJ/mol; Si—Br=343 kJ/mol; Si—I=339 kJ/mol). If necessary, the deposition may further utilize an N-containing co-reactant, such as $NH_3$. Vapors of the disclosed Si-containing film forming composition and the halosilane compounds may be introduced sequentially or simultaneously into the reactor, depending on the desired concentration of the final film. The selected sequence of precursor injection will be determined based upon the desired film composition targeted. The precursor introduction steps may be repeated until the deposited layer achieves a suitable thickness. One of ordinary skill in the art will recognize that the introductory pulses may be simultaneous when using a spatial ALD device. As described in PCT Pub No WO2011/123792, the order of the introduction of the precursors may be varied and the deposition may be performed with or without the $NH_3$ co-reactant in order to tune the amounts of carbon and nitrogen in the SiCN film.

In yet another alternative, a silicon-containing film may be deposited by the flowable PECVD method disclosed in U.S. Pat. App. Pub. No. 2014/0051264 using the disclosed Si-containing film forming compositions and a radical nitrogen- or oxygen-containing co-reactant. The radical nitrogen- or oxygen-containing co-reactant, such as $NH_3$ or $H_2O$ respectively, is generated in a remote plasma system. The radical co-reactant and the vapor phase of the disclosed compositions are introduced into the reaction chamber where they react and deposit the initially flowable film on the substrate. Applicants believe that the nitrogen atom of the disclosed compounds help to further improve the flowability of the deposited film, resulting in films having less voids.

Also disclosed are methods of using the disclosed carbosilane substituted amine precursors in casting deposition methods, such as spin coating, spray coating, dip coating or slit coating techniques. The disclosed methods provide for the use of the Si-containing film forming composition for deposition of silicon-containing films. The disclosed methods may be useful in the manufacture of semiconductor, photovoltaic, LCD-TFT, or flat panel type devices. The method includes: applying the liquid form of the disclosed Si-containing film forming composition on a substrate in a reactor: and forming the Si-containing layer on the substrate. As discussed previously, the liquid form of the disclosed Si-containing thin film may be a neat solution of the carbosilane substituted amine precursor or a mixture of the precursor with a solvent and optional pH adjusters or surfactants. The liquid form of the disclosed Si-containing film forming composition may be applied directly to the center of the substrate or may be applied to the entire substrate by spraying. When applied directly to the center of the substrate, the substrate may be spun to utilize centrifugal forces to evenly distribute the composition over the substrate. Alternatively, the substrate may be dipped in the Si-containing film forming composition. The resulting film may be dried at room temperature for a period of time to vaporize any solvent or volatile components of the film. During the drying process, a mist of water may be sprayed onto the substrate to promote the hydrolysis reaction of the film.

The disclosed carbosilane substituted amine precursors in the Si-containing film forming compositions may prove useful as monomers for the synthesis of carbosilane containing polymers. The Si-containing film forming compositions may be used to form spin-on dielectric film formulations, for patternable films, or for anti-reflective films. For example, the disclosed Si-containing film forming compositions may be included in a solvent and applied to a substrate to form a film. If necessary, the substrate may be rotated to evenly distribute the Si-containing film forming composition across the substrate. One of ordinary skill in the art will recognize that the viscosity of the Si-containing film forming compositions will contribute as to whether rotation of the substrate is necessary. The resulting film may be heated under an inert gas, such as Argon, Helium, or nitrogen and/or under reduced pressure. Alternatively, electron beams or ultraviolet radiation may be applied to the resulting film. The 11-18 hydrolysable groups of the disclosed carbosilane substituted amine precursors (i.e., the direct Si—N or Si—H or Si—X bonds) may prove useful to increase the connectivity of the polymer obtained.

The silicon-containing films resulting from the processes discussed above may include Si, SiC, $SiO_2$, SiN, SiON, SiCN, SiCOH, pSiCOH, or $MSiO_x$, wherein M is an element such as Hf, Zr, Ti, Nb, Ta, or Ge, and x may be 0-4, depending of course on the oxidation state of M. One of ordinary skill in the art will recognize that by judicial selection of the appropriate Si-containing film forming composition and co-reactants, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the silicon-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 600° C. for less than 3600 seconds under a H-containing atmosphere. The resulting film may contain fewer impurities and therefore may have improved performance characteristics. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the silicon-containing film.

EXAMPLES

The following non-limiting examples are provided to further illustrate embodiments of the invention. However, the examples are not intended to be all inclusive and are not intended to limit the scope of the inventions described herein.

Example 1: Synthesis of iPrN(—$SiH_2$—$CH_2$—$SiH_3$)$_2$ClSiH$_2$—$CH_2$—$SiH_3$+iPrNH$_2$+iPr$_2$EtN→iPrN(—$SiH_2$—$CH_2$—$SiH_3$)$_2$ A two liter 3-neck flask is equipped with a −78° C. (dry ice/acetone) condensor, charged with pentane (250 mL) and cooled to −78° C. iPrNH$_2$ (14.7 g, 0.248 mol) and iPr$_2$EtN (64 g, 0.497 mol) were added to the flask. 1-chloro-1,3-disilapropane (53.3 g, 0.48 mol) was slowly added dropwise over approximately 1 hour. Formation of white solids in a clear liquid was observed. After completing the addition, the suspension was slowly brought to room temperature with vigorous stirring. Stirring continued overnight. The reaction mixture was filtered over a medium fritted glass filter and solids washed with additional pentane. Solvent removed under reduced pressure yielding a cloudy liquid.

The resulting filtrate was then distilled using a short path column. The final product is distilled at 22° C./170 mTorr as a colorless liquid. Yield: 7 g (14%).

NMR of the final product NMR collected on a 400 MHz instrument. iPrN(—SiH$_2$CH$_2$SiH$_3$)$_2$ in C$_6$D$_6$: $^1$H NMR: δ −0.15 (sext. 4H, —CH$_2$—), 1.07 (d, 6H, 3.69, J$_{HH}$=6.5 Hz, —CHMe$_2$), 3.07 (mult., 1H, —CHMe$_2$), 3.70 (t, 6H, J$_{HH}$=4.5 Hz, —SiH$_3$), 4.57 (t, 4H, J$_{HH}$=4 Hz, —SiH2-); $^{29}$Si NMR: δ −27.1, −65.24. Thermogravimetric analysis (TGA) in open cup (oc) conditions produces less than 1% w/w residue. Closed cup (cc) TGA produces less than 2% w/w residue. See FIG. 1.

Example 2: Synthesis of HN(—SiH$_2$—CH$_2$—SiH$_3$)$_2$ ClSiH$_2$—CH$_2$—SiH$_3$+NH$_3$→HN(—SiH$_2$—CH$_2$—SiH$_3$)$_2$ A 1.21 M solution of ClSiH$_2$—CH$_2$—SiH$_3$ (53.6 g) was prepared in Toluene at −15° C. The mixture was warmed to +5° C. and NH$_3$ (11.5 g) was bubbled slowly into the mixture over ~1.5 h. The reaction mixture was allowed to warm of its own. After addition the mix was allowed to stir for 0.5 h at room temperature (approx. 23° C.) followed by GC sampling. GC shows only single product NHDSP$_2$. The GC showed the product at 9.032 minutes retention time, as well as the solvent and reactant peaks.

Example 3: Synthesis of N(—SiH$_2$—CH$_2$—SiH$_3$)$_3$ ClSiH$_2$—CH$_2$—SiH$_3$+NH$_3$→N(—SiH$_2$—CH$_2$—SiH$_3$)$_3$ A 500 mL 3-neck flask, equipped with a −78° C. (dry ice/acetone) condenser, was charged with dry pentane (100 mL) and 1-chloro-1,3-disilapropane (15 g, 0.135 mol) and cooled to 0° C. Gaseous ammonia was condensed into the flask (2.5 g, 0.147 mol). Initially some fuming was observed followed by formation of a large amount of white solids in a clear liquid. The suspension was slowly brought to room temperature with vigorous stirring. Stirring continued at room temperature for approximately 60 hours. The reaction mixture was filtered over a medium fritted glass filter and solids washed with an additional 100 mL of dry pentane to afford a clear colorless liquid. Solvents and high volatiles are removed using a short path column under atmospheric pressure at 32-37° C. The final product is distilled using a short path column at 26-36° C./40-45 mTorr as a colorless liquid. Yield: 4.3 g (50%).

Figure 2:
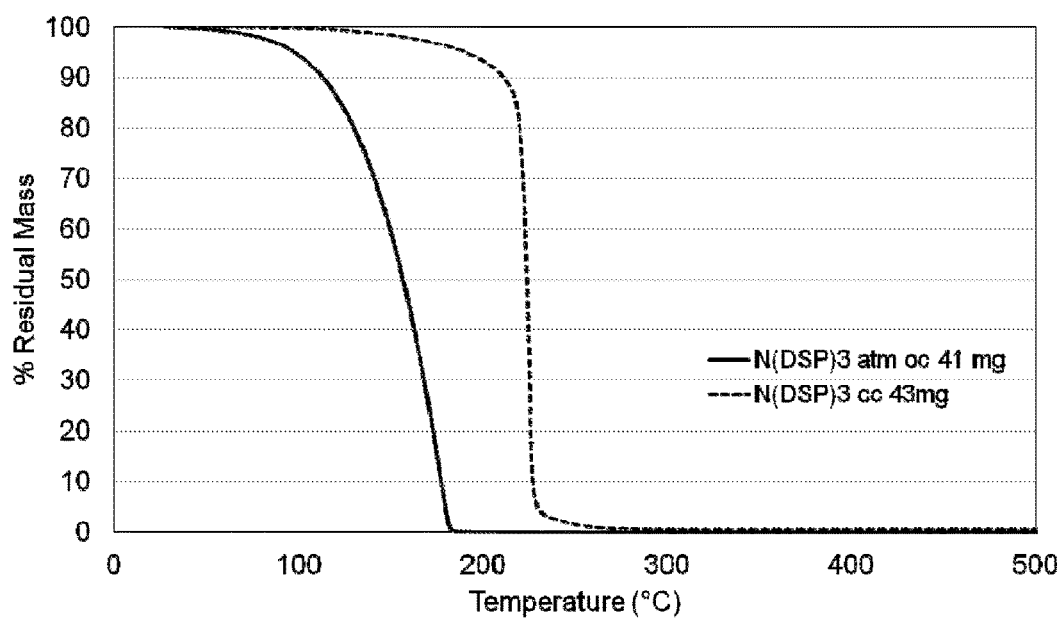
FIG. 2 is a TGA graph demonstrating the percentage of weight loss with temperature change for N(—$SiH_2$—$CH_2$—$SiH_3$)$_3$.

NMR of the final product NMR collected on a 400 MHz instrument. N(—SiH$_2$—CH$_2$—SiH$_3$)$_3$ in C$_6$D$_6$: $^1$H NMR: δ −0.16 (sext. 6H, —CH$_2$—), 3.69 (t, 9H, J$_{HH}$=4.5 Hz, —SiH$_3$), 4.60 (t, 6H, J$_{HH}$=4 Hz, —SiH2-); $^{29}$Si NMR: δ −21.6, −65.23. Thermogravimetric analysis (TGA) in open cup (oc) and closed cup (cc) conditions produces less than 1% w/w residue. See FIG. 2.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A Si-containing film forming composition comprising a carbosilane substituted amine precursor having the formula (R$^1$)$_a$N(—SiHR$^2$—CH$_2$—SiH$_2$R$^3$)$_{3-a}$, wherein a=0 or 1; R$^1$ is H, a C1 to C6 alkyl group, or a halogen; R$^2$ and R$^3$ is each independently H, a halogen, an alkoxy group having the formula OR', wherein R' is an alkyl group (C1 to C6), or an alkylamino group having the formula NR"$_2$, wherein each R" is independently H, a C1-C6 alkyl group, a C1-C6 alkenyl group, or a C3-C10 aryl or heterocycle group.

2. The Si-containing film forming composition of claim 1, wherein a=0 and the carbosilane substituted amine precursor has the formula N(—SiHR$^2$—CH$_2$—SiH$_2$R$^3$)$_3$.

3. The Si-containing film forming composition of claim 2, wherein the carbosilane substituted amine precursor is selected from the group consisting of N(SiH$_2$—CH$_2$—SiH$_2$(Cl))$_3$, N(SiH$_2$—CH$_2$—SiH$_2$(Br))$_3$, N(SiH$_2$—CH$_2$—SiH$_2$(I))$_3$, N(SiH$_2$—CH$_2$—SiH$_2$(NH$_2$))$_3$, N(SiH$_2$—CH$_2$—SiH$_2$(NMe$_2$))$_3$, N(SiH$_2$—CH$_2$—SiH$_2$(NMeEt))$_3$, N(SiH$_2$—CH$_2$—SiH$_2$(NEt$_2$))$_3$, N(SiH$_2$—CH$_2$—SiH$_2$(NnPr$_2$))$_3$, N(SiH$_2$—CH$_2$—SiH$_2$(NiPr$_2$))$_3$, N(SiH$_2$—CH$_2$—SiH$_2$(NBu$_2$))$_3$, N(SiH$_2$—CH$_2$—SiH$_2$(NiBu$_2$))$_3$, N(SiH$_2$—CH$_2$—SiH$_2$(NtBu$_2$))$_3$, N(SiH$_2$—CH$_2$—SiH$_2$(NAm$_2$))$_3$, N(SiH$_2$—CH$_2$—SiH$_2$(NCyPentyl$_2$))$_3$, N(SiH$_2$—CH$_2$—SiH$_2$(Nhexyl$_2$))$_3$, N(SiH$_2$—CH$_2$—SiH$_2$(NCyHex$_2$))$_3$, N(SiH$_2$—CH$_2$—SiH$_2$(NMeH))$_3$, N(SiH$_2$—CH$_2$—SiH$_2$(NEtH))$_3$, N(SiH$_2$—CH$_2$—SiH$_2$(NnPrH))$_3$, N(SiH$_2$—CH$_2$—SiH$_2$(NiPrH))$_3$, N(SiH$_2$—CH$_2$—SiH$_2$(NBuH))$_3$, N(SiH$_2$—CH$_2$—SiH$_2$(NiBuH))$_3$, N(SiH$_2$—CH$_2$—SiH$_2$(Nt-BuH))$_3$, N(SiH$_2$—CH$_2$—SiH$_2$(NAmH))$_3$, N(SiH$_2$—CH$_2$—SiH$_2$(OH))$_3$, N(SiH$_2$—CH$_2$—SiH$_2$(OMe))$_3$, N(SiH$_2$—CH$_2$—SiH$_2$(OEt))$_3$, N(SiH$_2$—CH$_2$—SiH$_2$(OnPr))$_3$, N(SiH$_2$—CH$_2$—SiH$_2$(OiPr))$_3$, N(SiH$_2$—CH$_2$—SiH$_2$(OBu))$_3$, N(SiH$_2$—CH$_2$—SiH$_2$(OiBu))$_3$, N(SiH$_2$—CH$_2$—SiH$_2$(OtBu))$_3$, N(SiH$_2$—CH$_2$—SiH$_2$(OAm))$_3$, N(SiH$_2$—CH$_2$—SiH$_2$(OHexyl))$_3$, N(SiH$_2$—CH$_2$—SiH$_2$(Cl))$_2$(SiH$_2$—CH$_2$SiH$_3$), N(SiH$_2$—CH$_2$—SiH$_2$(Br))$_2$(SiH$_2$—CH$_2$SiH$_3$), N(SiH$_2$—CH$_2$—SiH$_2$(I))$_2$(SiH$_2$—CH$_2$SiH$_3$), N(SiH$_2$—CH$_2$—SiH$_2$(NH$_2$))$_2$(SiH$_2$—CH$_2$SiH$_3$), N(SiH$_2$—CH$_2$—SiH$_2$(NMe$_2$))$_2$(SiH$_2$—CH$_2$SiH$_3$), N(SiH$_2$—CH$_2$—SiH$_2$(NMeEt))$_2$(SiH$_2$—CH$_2$SiH$_3$), N(SiH$_2$—CH$_2$—SiH$_2$(NEt$_2$))$_2$(SiH$_2$—CH$_2$SiH$_3$), N(SiH$_2$—CH$_2$—SiH$_2$(NnPr$_2$))$_2$(SiH$_2$—CH$_2$SiH$_3$), N(SiH$_2$—CH$_2$—SiH$_2$(NiPr$_2$))$_2$(SiH$_2$—CH$_2$SiH$_3$), N(SiH$_2$—CH$_2$—SiH$_2$(NBu$_2$))$_2$(SiH$_2$—CH$_2$SiH$_3$), N(SiH$_2$—CH$_2$—SiH$_2$(NiBu$_2$))$_2$(SiH$_2$—CH$_2$SiH$_3$), N(SiH$_2$—CH$_2$—SiH$_2$(NtBu$_2$))$_2$(SiH$_2$—CH$_2$SiH$_3$), N(SiH$_2$—CH$_2$—SiH$_2$(NHtBu))$_2$(SiH$_2$—CH$_2$SiH$_3$), N(SiH$_2$—CH$_2$—SiH$_2$(NAm$_2$))$_2$(SiH$_2$—CH$_2$SiH$_3$), N(SiH$_2$—CH$_2$—SiH$_2$(NHAm))$_2$(SiH$_2$—CH$_2$SiH$_3$), N(SiH$_2$—CH$_2$—SiH$_2$(NCyPentyl$_2$))$_2$(SiH$_2$—CH$_2$SiH$_3$), N(SiH$_2$—CH$_2$—SiH$_2$(Nhexyl$_2$))$_2$(SiH$_2$—CH$_2$SiH$_3$), N(SiH$_2$—CH$_2$—SiH$_2$(NCyHex$_2$))$_2$(SiH$_2$—CH$_2$SiH$_3$), N(SiH$_2$—CH$_2$—SiH$_2$(NMeH))$_2$(SiH$_2$—CH$_2$SiH$_3$), N(SiH$_2$—CH$_2$—SiH$_2$(NEtH))$_2$(SiH$_2$—CH$_2$SiH$_3$), N(SiH$_2$—CH$_2$—SiH$_2$(NnPrH))$_2$(SiH$_2$—CH$_2$SiH$_3$), N(SiH$_2$—CH$_2$—SiH$_2$(NiPrH))$_2$(SiH$_2$—CH$_2$SiH$_3$), N(SiH$_2$—CH$_2$—SiH$_2$(OH))$_2$(SiH$_2$—CH$_2$SiH$_3$), N(SiH$_2$—CH$_2$—SiH$_2$(OMe))$_2$(SiH$_2$—CH$_2$SiH$_3$), N(SiH$_2$—CH$_2$—SiH$_2$(OEt))$_2$(SiH$_2$—CH$_2$SiH$_3$), N(SiH$_2$—CH$_2$—SiH$_2$(OnPr))$_2$(SiH$_2$—CH$_2$SiH$_3$), N(SiH$_2$—CH$_2$—SiH$_2$(OiPr))$_2$(SiH$_2$—CH$_2$SiH$_3$), N(SiH$_2$—CH$_2$—SiH$_2$(OBu))$_2$(SiH$_2$—CH$_2$SiH$_3$), N(SiH$_2$—CH$_2$—SiH$_2$(OiBu))$_2$(SiH$_2$—CH$_2$SiH$_3$), N(SiH$_2$—CH$_2$—SiH$_2$(OtBu))$_2$(SiH$_2$—CH$_2$SiH$_3$), N(SiH$_2$—CH$_2$—SiH$_2$(OAm))$_2$(SiH$_2$—CH$_2$SiH$_3$), N(SiH$_2$—CH$_2$—SiH$_2$(OHexyl))$_2$(SiH$_2$—CH$_2$SiH$_3$), N(SiH$_2$—CH$_2$—SiH$_2$(Cl))(SiH$_2$—CH$_2$SiH$_3$)$_2$, N(SiH$_2$—CH$_2$—SiH$_2$(Br))(SiH$_2$—CH$_2$SiH$_3$)$_2$, N(SiH$_2$—CH$_2$—SiH$_2$(I))(SiH$_2$—CH$_2$SiH$_3$)$_2$, N(SiH$_2$—CH$_2$—SiH$_2$(NH$_2$))(SiH$_2$—CH$_2$SiH$_3$)$_2$, N(SiH$_2$—CH$_2$—SiH$_2$(NMe$_2$))(SiH$_2$—CH$_2$SiH$_3$)$_2$, N(SiH$_2$—CH$_2$—SiH$_2$(NMeEt))(SiH$_2$—CH$_2$SiH$_3$)$_2$, N(SiH$_2$—CH$_2$—SiH$_2$(NEt$_2$))(SiH$_2$—CH$_2$SiH$_3$)$_2$, N(SiH$_2$—CH$_2$—SiH$_2$(NnPr$_2$))(SiH$_2$—

CH$_2$SiH$_3$)$_2$, N(SiH$_2$—CH$_2$—SiH$_2$(NiPr$_2$))(SiH$_2$—CH$_2$SiH$_3$)$_2$, N(SiH$_2$—CH$_2$—SiH$_2$(NBu$_2$))(SiH$_2$—CH$_2$SiH$_3$)$_2$, N(SiH$_2$—CH$_2$—SiH$_2$(NiBu$_2$))(SiH$_2$—CH$_2$SiH$_3$)$_2$, N(SiH$_2$—CH$_2$—SiH$_2$(NtBu$_2$))(SiH$_2$—CH$_2$SiH$_3$)$_2$, N(SiH$_2$—CH$_2$—SiH$_2$(NHtBu))(SiH$_2$—CH$_2$SiH$_3$)$_2$, N(SiH$_2$—CH$_2$—SiH$_2$(NAm$_2$))(SiH$_2$—CH$_2$SiH$_3$)$_2$, N(SiH$_2$—CH$_2$—SiH$_2$(NHAm))(SiH$_2$—CH$_2$SiH$_3$)$_2$, N(SiH$_2$—CH$_2$—SiH$_2$(NCyPentyl$_2$))(SiH$_2$—CH$_2$SiH$_3$)$_2$, N(SiH$_2$—CH$_2$—SiH$_2$(Nhexyl$_2$))(SiH$_2$—CH$_2$SiH$_3$)$_2$, N(SiH$_2$—CH$_2$—SiH$_2$(NCyHex$_2$))(SiH$_2$—CH$_2$SiH$_3$)$_2$, N(SiH$_2$—CH$_2$—SiH$_2$(NMeH))(SiH$_2$—CH$_2$SiH$_3$)$_2$, N(SiH$_2$—CH$_2$—SiH$_2$(NEtH))(SiH$_2$—CH$_2$SiH$_3$)$_2$, N(SiH$_2$—CH$_2$—SiH$_2$(NnPrH))(SiH$_2$—CH$_2$SiH$_3$)$_2$, N(SiH$_2$—CH$_2$—SiH$_2$(NiPrH))(SiH$_2$—CH$_2$SiH$_3$)$_2$, N(SiH$_2$—CH$_2$—SiH$_2$(OH))(SiH$_2$—CH$_2$SiH$_3$)$_2$, N(SiH$_2$—CH$_2$—SiH$_2$(OMe))(SiH$_2$—CH$_2$SiH$_3$)$_2$, N(SiH$_2$—CH$_2$—SiH$_2$(OEt))(SiH$_2$—CH$_2$SiH$_3$)$_2$, N(SiH$_2$—CH$_2$—SiH$_2$(OnPr))(SiH$_2$—CH$_2$SiH$_3$)$_2$, N(SiH$_2$—CH$_2$—SiH$_2$(OiPr))(SiH$_2$—CH$_2$SiH$_3$)$_2$, N(SiH$_2$—CH$_2$—SiH$_2$(OBu))(SiH$_2$—CH$_2$SiH$_3$)$_2$, N(SiH$_2$—CH$_2$—SiH$_2$(OiBu))(SiH$_2$—CH$_2$SiH$_3$)$_2$, N(SiH$_2$—CH$_2$—SiH$_2$(OtBu))(SiH$_2$—CH$_2$SiH$_3$)$_2$, N(SiH$_2$—CH$_2$—SiH$_2$(OAm))(SiH$_2$—CH$_2$SiH$_3$)$_2$, and N(SiH$_2$—CH$_2$—SiH$_2$(OHexyl))(SiH$_2$—CH$_2$SiH$_3$)$_2$.

4. The Si-containing film forming composition of claim 2, wherein the carbosilane substituted amine precursor is selected from the group consisting of N(SiH$_2$—CH$_2$—SiH$_3$)$_3$, N(Si(H)(Cl)—CH$_2$—SiH$_3$)$_3$, N(Si(H)(Br)—CH$_2$—SiH$_3$)$_3$, N(Si(H)(I)—CH$_2$—SiH$_3$)$_3$, N(Si(H)(NH$_2$)—CH$_2$—SiH$_3$)$_3$, N(Si(H)(NMe$_2$)-CH$_2$—SiH$_3$)$_3$, N(Si(H)(NEtMe)-CH$_2$—SiH$_3$)$_3$, N(Si(H)(NEt$_2$)-CH$_2$—SiH$_3$)$_3$, N(Si(H)(NnPr$_2$)—CH$_2$—SiH$_3$)$_3$, N(Si(H)(NiPr$_2$)—CH$_2$—SiH$_3$)$_3$, N(Si(H)(NBu$_2$)-CH$_2$—SiH$_3$)$_3$, N(Si(H)(NiBu$_2$)-CH$_2$—SiH$_3$)$_3$, N(Si(H)(NtBu$_2$)-CH$_2$—SiH$_3$)$_3$, N(Si(H)(NHtBu)-CH$_2$—SiH$_3$)$_3$, N(Si(H)(NAm$_2$)—CH$_2$—SiH$_3$)$_3$, N(Si(H)(NHAm)—CH$_2$—SiH$_3$)$_3$, N(Si(H)(NCyPentyl$_2$)-CH$_2$—SiH$_3$)$_3$, N(Si(H)(Nhexyl$_2$)-CH$_2$—SiH$_3$)$_3$, N(Si(H)(NCyHex$_2$)-CH$_2$—SiH$_3$)$_3$, N(Si(H)(NMeH)—CH$_2$—SiH$_3$)$_3$, N(Si(H)(NEtH)—CH$_2$—SiH$_3$)$_3$, N(Si(H)(NnPrH)—CH$_2$—SiH$_3$)$_3$, N(Si(H)(NiPrH)—CH$_2$—SiH$_3$)$_3$, N(Si(H)(NBuH)—CH$_2$—SiH$_3$)$_3$, N(Si(H)(NtBuH)—CH$_2$—SiH$_3$)$_3$, N(Si(H)(OH)—CH$_2$—SiH$_3$)$_3$, N(Si(H)(OMe)-CH$_2$—SiH$_3$)$_3$, N(Si(H)(OEt)-CH$_2$—SiH$_3$)$_3$, N(Si(H)(OnPr)—CH$_2$—SiH$_3$)$_3$, N(Si(H)(OiPr)—CH$_2$—SiH$_3$)$_3$, N(Si(H)(OBu)-CH$_2$—SiH$_3$)$_3$, N(Si(H)(OiBu)-CH$_2$—SiH$_3$)$_3$, N(Si(H)(OtBu)-CH$_2$—SiH$_3$)$_3$, N(Si(H)(OAm)—CH$_2$—SiH$_3$)$_3$, N(Si(H)(OHexyl)-CH$_2$—SiH$_3$)$_3$, N(Si(H)(Cl)—CH$_2$—SiH$_3$)$_2$(SiH$_2$—CH$_2$SiH$_3$), N(Si(H)(Br)—CH$_2$—SiH$_3$)$_2$(SiH$_2$—CH$_2$SiH$_3$), N(Si(H)(I)—CH$_2$—SiH$_3$)$_2$(SiH$_2$—CH$_2$SiH$_3$), N(Si(H)(NH$_2$)—CH$_2$—SiH$_3$)$_2$(SiH$_2$—CH$_2$SiH$_3$), N(Si(H)(NMe$_2$)-CH$_2$—SiH$_3$)$_2$(SiH$_2$—CH$_2$SiH$_3$), N(Si(H)(NMeEt)-CH$_2$—SiH$_3$)$_2$(SiH$_2$—CH$_2$SiH$_3$), N(Si(H)(NEt$_2$)-CH$_2$—SiH$_3$)$_2$(SiH$_2$—CH$_2$SiH$_3$), N(Si(H)(NnPr$_2$)—CH$_2$—SiH$_3$)$_2$(SiH$_2$—CH$_2$SiH$_3$), N(Si(H)(NiPr$_2$)—CH$_2$—SiH$_3$)$_2$(SiH$_2$—CH$_2$SiH$_3$), N(Si(H)(NBu$_2$)-CH$_2$—SiH$_3$)$_2$(SiH$_2$—CH$_2$SiH$_3$), N(Si(H)(NiBu$_2$)-CH$_2$—SiH$_3$)$_2$(SiH$_2$—CH$_2$SiH$_3$), N(Si(H)(NtBu$_2$)-CH$_2$—SiH$_3$)$_2$(SiH$_2$—CH$_2$SiH$_3$), N(Si(H)(NHtBu)-CH$_2$—SiH$_3$)$_2$(SiH$_2$—CH$_2$SiH$_3$), N(Si(H)(NAm$_2$)—CH$_2$—SiH$_3$)$_2$(SiH$_2$—CH$_2$SiH$_3$), N(Si(H)(NHAm)—CH$_2$—SiH$_3$)$_2$(SiH$_2$—CH$_2$SiH$_3$), N(Si(H)(NCyPentyl$_2$)-CH$_2$—SiH$_3$)$_2$(SiH$_2$—CH$_2$SiH$_3$), N(Si(H)(Nhexyl$_2$)-CH$_2$—SiH$_3$)$_2$(SiH$_2$—CH$_2$SiH$_3$), N(Si(H)(NCyHex$_2$)-CH$_2$—SiH$_3$)$_2$(SiH$_2$—CH$_2$SiH$_3$), N(Si(H)(NMeH)—CH$_2$—SiH$_3$)$_2$(SiH$_2$—CH$_2$SiH$_3$), N(Si(H)(NEtH)—CH$_2$—SiH$_3$)$_2$(SiH$_2$—CH$_2$SiH$_3$), N(Si(H)(NnPrH)—CH$_2$—SiH$_3$)$_2$(SiH$_2$—CH$_2$SiH$_3$), N(Si(H)(NiPrH)—CH$_2$—SiH$_3$)$_2$(SiH$_2$—CH$_2$SiH$_3$), N(Si(H)(OH)—CH$_2$—SiH$_3$)$_2$(SiH$_2$—CH$_2$SiH$_3$), N(Si(H)(OMe)-CH$_2$—SiH$_3$)$_2$(SiH$_2$—CH$_2$SiH$_3$), N(Si(H)(OEt)-CH$_2$—SiH$_3$)$_2$(SiH$_2$—CH$_2$SiH$_3$), N(Si(H)(OnPr)—CH$_2$—SiH$_3$)$_2$(SiH$_2$—CH$_2$SiH$_3$), N(Si(H)(OiPr)—CH$_2$—SiH$_3$)$_2$(SiH$_2$—CH$_2$SiH$_3$), N(Si(H)(OBu)-CH$_2$—SiH$_3$)$_2$(SiH$_2$—CH$_2$SiH$_3$), N(Si(H)(OiBu)-CH$_2$—SiH$_3$)$_2$(SiH$_2$—CH$_2$SiH$_3$), N(Si(H)(OtBu)-CH$_2$—SiH$_3$)$_2$(SiH$_2$—CH$_2$SiH$_3$), N(Si(H)(OAm)—CH$_2$—SiH$_3$)$_2$(SiH$_2$—CH$_2$SiH$_3$), N(Si(H)(NMe$_2$)-CH$_2$—SiH$_3$)(SiH$_2$—CH$_2$SiH$_3$)$_2$, N(Si(H)(NMeEt)-CH$_2$—SiH$_3$)(SiH$_2$—CH$_2$SiH$_3$)$_2$, N(Si(H)(NEt$_2$)-CH$_2$—SiH$_3$)(SiH$_2$—CH$_2$SiH$_3$)$_2$, N(Si(H)(NnPr$_2$)—CH$_2$—SiH$_3$)(SiH$_2$—CH$_2$SiH$_3$)$_2$, N(Si(H)(NiPr$_2$)—CH$_2$—SiH$_3$)(SiH$_2$—CH$_2$SiH$_3$)$_2$, N(Si(H)(NBu$_2$)-CH$_2$—SiH$_3$)(SiH$_2$—CH$_2$SiH$_3$)$_2$, N(Si(H)(NiBu$_2$)-CH$_2$—SiH$_3$)(SiH$_2$—CH$_2$SiH$_3$)$_2$, N(Si(H)(NtBu$_2$)-CH$_2$—SiH$_3$)(SiH$_2$—CH$_2$SiH$_3$)$_2$, N(Si(H)(NHtBu)-CH$_2$—SiH$_3$)(SiH$_2$—CH$_2$SiH$_3$)$_2$, N(Si(H)(NAm$_2$)—CH$_2$—SiH$_3$)(SiH$_2$—CH$_2$SiH$_3$)$_2$, N(Si(H)(NHAm)—CH$_2$—SiH$_3$)(SiH$_2$—CH$_2$SiH$_3$)$_2$, N(Si(H)(NCyPentyl$_2$)-CH$_2$—SiH$_3$)(SiH$_2$—CH$_2$SiH$_3$)$_2$, N(Si(H)(Nhexyl$_2$)-CH$_2$—SiH$_3$)(SiH$_2$—CH$_2$SiH$_3$)$_2$, N(Si(H)(NCyHex$_2$)-CH$_2$—SiH$_3$)(SiH$_2$—CH$_2$SiH$_3$)$_2$, N(Si(H)(NMeH)—CH$_2$—SiH$_3$)(SiH$_2$—CH$_2$SiH$_3$)$_2$, N(Si(H)(NEtH)—CH$_2$—SiH$_3$)(SiH$_2$—CH$_2$SiH$_3$)$_2$, N(Si(H)(NnPrH)—CH$_2$—SiH$_3$)(SiH$_2$—CH$_2$SiH$_3$)$_2$, N(Si(H)(NiPrH)—CH$_2$—SiH$_3$)(SiH$_2$—CH$_2$SiH$_3$)$_2$, N(Si(H)(OH)—CH$_2$—SiH$_3$)(SiH$_2$—CH$_2$SiH$_3$)$_2$, N(Si(H)(OMe)-CH$_2$—SiH$_3$)(SiH$_2$—CH$_2$SiH$_3$)$_2$, N(Si(H)(OEt)-CH$_2$—SiH$_3$)(SiH$_2$—CH$_2$SiH$_3$)$_2$, N(Si(H)(OnPr)—CH$_2$—SiH$_3$)(SiH$_2$—CH$_2$SiH$_3$)$_2$, N(Si(H)(OiPr)—CH$_2$—SiH$_3$)(SiH$_2$—CH$_2$SiH$_3$)$_2$, N(Si(H)(OBu)-CH$_2$—SiH$_3$)(SiH$_2$—CH$_2$SiH$_3$)$_2$, N(Si(H)(OiBu)-CH$_2$—SiH$_3$)(SiH$_2$—CH$_2$SiH$_3$)$_2$, N(Si(H)(OtBu)-CH$_2$—SiH$_3$)(SiH$_2$—CH$_2$SiH$_3$)$_2$, N(Si(H)(OAm)—CH$_2$—SiH$_3$)(SiH$_2$—CH$_2$SiH$_3$)$_2$, and N(Si(H)(OHexyl)-CH$_2$—SiH$_3$)(SiH$_2$—CH$_2$SiH$_3$)$_2$.

5. The Si-containing film forming composition of claim 2, wherein the carbosilane substituted amine precursor is N(—SiH$_2$—CH$_2$—SiH$_3$)$_3$.

6. The Si-containing film forming composition of claim 1, wherein a=1 and the carbosilane substituted amine precursor has the formula R$^1$N(—SiHR$^2$—CH$_2$—SiH$_2$R$^3$)$_2$.

7. The Si-containing film forming composition of claim 6, wherein the carbosilane substituted amine precursor is selected from the group consisting of HN(SiH$_2$—CH$_2$—SiH$_2$(Cl))$_2$, (Me)N(SiH$_2$—CH$_2$—SiH$_2$(Cl))$_2$, (Et)N(SiH$_2$—CH$_2$—SiH$_2$(Cl))$_2$, (nPr)N(SiH$_2$—CH$_2$—SiH$_2$(Cl))$_2$, (iPr)N(SiH$_2$—CH$_2$—SiH$_2$(Cl))$_2$, (Bu)N(SiH$_2$—CH$_2$—SiH$_2$(Cl))$_2$, (iBu)N(SiH$_2$—CH$_2$—SiH$_2$(Cl))$_2$, (tBu)N(SiH$_2$—CH$_2$—SiH$_2$(Cl))$_2$, (amyl)N(SiH$_2$—CH$_2$—SiH$_2$(Cl))$_2$, (hexyl)N(SiH$_2$—CH$_2$—SiH$_2$(Cl))$_2$, HN(SiH$_2$—CH$_2$—SiH$_2$(Br))$_2$, (Me)N(SiH$_2$—CH$_2$—SiH$_2$(Br))$_2$, (Et)N(SiH$_2$—CH$_2$—SiH$_2$(Br))$_2$, (nPr)N(SiH$_2$—CH$_2$—SiH$_2$(Br))$_2$, (iPr)N(SiH$_2$—CH$_2$—SiH$_2$(Br))$_2$, (Bu)N(SiH$_2$—CH$_2$—SiH$_2$(Br))$_2$, (iBu)N(SiH$_2$—CH$_2$—SiH$_2$(Br))$_2$, (tBu)N(SiH$_2$—CH$_2$—SiH$_2$(Br))$_2$, (amyl)N(SiH$_2$—CH$_2$—SiH$_2$(Br))$_2$, (hexyl)N(SiH$_2$—CH$_2$—SiH$_2$(Br))$_2$, HN(SiH$_2$—CH$_2$—SiH$_2$(I))$_2$, (Me)N(SiH$_2$—CH$_2$—SiH$_2$(I))$_2$, (Et)N(SiH$_2$—CH$_2$—SiH$_2$(I))$_2$, (nPr)N(SiH$_2$—CH$_2$—SiH$_2$(I))$_2$, (iPr)N(SiH$_2$—CH$_2$—SiH$_2$(I))$_2$, (Bu)N(SiH$_2$—CH$_2$—SiH$_2$(I))$_2$, (iBu)N(SiH$_2$—CH$_2$—SiH$_2$(I))$_2$, (tBu)N(SiH$_2$—CH$_2$—SiH$_2$(I))$_2$, (amyl)N(SiH$_2$—CH$_2$—SiH$_2$(I))$_2$, (hexyl)N(SiH$_2$—CH$_2$—SiH$_2$(I))$_2$, HN(SiH$_2$—CH$_2$—SiH$_2$(NH$_2$))$_2$, (Me)N(SiH$_2$—CH$_2$—SiH$_2$(NH$_2$))$_2$, (Et)N(SiH$_2$—CH$_2$—SiH$_2$(NH$_2$))$_2$, (nPr)N(SiH$_2$—CH$_2$—SiH$_2$(NH$_2$))$_2$, (iPr)N(SiH$_2$—CH$_2$—SiH$_2$(NH$_2$))$_2$, (Bu)N(SiH$_2$—CH$_2$—SiH$_2$(NH$_2$))$_2$, (iBu)N(SiH$_2$—CH$_2$—

SiH$_2$(NH$_2$))$_2$, (tBu)N(SiH$_2$—CH$_2$—SiH$_2$(NH$_2$))$_2$, (amyl)N(SiH$_2$—CH$_2$—SiH$_2$(NH$_2$))$_2$, (hexyl)N(SiH$_2$—CH$_2$—SiH$_2$(NH$_2$))$_2$, HN(SiH$_2$—CH$_2$—SiH$_2$(NMe$_2$))$_2$, (Me)N(SiH$_2$—CH$_2$—SiH$_2$(NMe$_2$))$_2$, (Et)N(SiH$_2$—CH$_2$—SiH$_2$(NMe$_2$))$_2$, (nPr)N(SiH$_2$—CH$_2$—SiH$_2$(NMe$_2$))$_2$, (iPr)N(SiH$_2$—CH$_2$—SiH$_2$(NMe$_2$))$_2$, (Bu)N(SiH$_2$—CH$_2$—SiH$_2$(NMe$_2$))$_2$, (iBu)N(SiH$_2$—CH$_2$—SiH$_2$(NMe$_2$))$_2$, (tBu)N(SiH$_2$—CH$_2$—SiH$_2$(NMe$_2$))$_2$, (amyl)N(SiH$_2$—CH$_2$—SiH$_2$(NMe$_2$))$_2$, (hexyl)N(SiH$_2$—CH$_2$—SiH$_2$(NMe$_2$))$_2$, HN(SiH$_2$—CH$_2$—SiH$_2$(NMeH))$_2$, (Me)N(SiH$_2$—CH$_2$—SiH$_2$(NMeH))$_2$, (Et)N(SiH$_2$—CH$_2$—SiH$_2$(NMeH))$_2$, (nPr)N(SiH$_2$—CH$_2$—SiH$_2$(NMeH))$_2$, (iPr)N(SiH$_2$—CH$_2$—SiH$_2$(NMeH))$_2$, (Bu)N(SiH$_2$—CH$_2$—SiH$_2$(NMeH))$_2$, (iBu)N(SiH$_2$—CH$_2$—SiH$_2$(NMeH))$_2$, (tBu)N(SiH$_2$—CH$_2$—SiH$_2$(NMeH))$_2$, (amyl)N(SiH$_2$—CH$_2$—SiH$_2$(NMeH))$_2$, (hexyl)N(SiH$_2$—CH$_2$—SiH$_2$(NMeH))$_2$, HN(SiH$_2$—CH$_2$—SiH$_2$(NMeEt))$_2$, (Me)N(SiH$_2$—CH$_2$—SiH$_2$(NMeEt))$_2$, (Et)N(SiH$_2$—CH$_2$—SiH$_2$(NMeEt))$_2$, (nPr)N(SiH$_2$—CH$_2$—SiH$_2$(NMeEt))$_2$, (iPr)N(SiH$_2$—CH$_2$—SiH$_2$(NMeEt))$_2$, (Bu)N(SiH$_2$—CH$_2$—SiH$_2$(NMeEt))$_2$, (iBu)N(SiH$_2$—CH$_2$—SiH$_2$(NMeEt))$_2$, (tBu)N(SiH$_2$—CH$_2$—SiH$_2$(NMeEt))$_2$, (amyl)N(SiH$_2$—CH$_2$—SiH$_2$(NMeEt))$_2$, (hexyl)N(SiH$_2$—CH$_2$—SiH$_2$(NMeEt))$_2$, HN(SiH$_2$—CH$_2$—SiH$_2$(NEtH))$_2$, (Me)N(SiH$_2$—CH$_2$—SiH$_2$(NEtH))$_2$, (Et)N(SiH$_2$—CH$_2$—SiH$_2$(NEtH))$_2$, (nPr)N(SiH$_2$—CH$_2$—SiH$_2$(NEtH))$_2$, (iPr)N(SiH$_2$—CH$_2$—SiH$_2$(NEtH))$_2$, (Bu)N(SiH$_2$—CH$_2$—SiH$_2$(NEtH))$_2$, (iBu)N(SiH$_2$—CH$_2$—SiH$_2$(NEtH))$_2$, (tBu)N(SiH$_2$—CH$_2$—SiH$_2$(NEtH))$_2$, (amyl)N(SiH$_2$—CH$_2$—SiH$_2$(NEtH))$_2$, (hexyl)N(SiH$_2$—CH$_2$—SiH$_2$(NEtH))$_2$, HN(SiH$_2$—CH$_2$—SiH$_2$(NiPrH))$_2$, (Me)N(SiH$_2$—CH$_2$—SiH$_2$(NiPrH))$_2$, (Et)N(SiH$_2$—CH$_2$—SiH$_2$(NiPrH))$_2$, (nPr)N(SiH$_2$—CH$_2$—SiH$_2$(NiPrH))$_2$, (iPr)N(SiH$_2$—CH$_2$—SiH$_2$(NiPrH))$_2$, (Bu)N(SiH$_2$—CH$_2$—SiH$_2$(NiPrH))$_2$, (iBu)N(SiH$_2$—CH$_2$—SiH$_2$(NiPrH))$_2$, (tBu)N(SiH$_2$—CH$_2$—SiH$_2$(NiPrH))$_2$, (amyl)N(SiH$_2$—CH$_2$—SiH$_2$(NiPrH))$_2$, (hexyl)N(SiH$_2$—CH$_2$—SiH$_2$(NiPrH))$_2$, HN(SiH$_2$—CH$_2$—SiH$_2$(OMe))$_2$, (Me)N(SiH$_2$—CH$_2$—SiH$_2$(OMe))$_2$, (Et)N(SiH$_2$—CH$_2$—SiH$_2$(OMe))$_2$, (nPr)N(SiH$_2$—CH$_2$—SiH$_2$(OMe))$_2$, (iPr)N(SiH$_2$—CH$_2$—SiH$_2$(OMe))$_2$, (Bu)N(SiH$_2$—CH$_2$—SiH$_2$(OMe))$_2$, (iBu)N(SiH$_2$—CH$_2$—SiH$_2$(OMe))$_2$, (tBu)N(SiH$_2$—CH$_2$—SiH$_2$(OMe))$_2$, (amyl)N(SiH$_2$—CH$_2$—SiH$_2$(OMe))$_2$, (hexyl)N(SiH$_2$—CH$_2$—SiH$_2$(OMe))$_2$, HN(SiH$_2$—CH$_2$—SiH$_2$(OEt))$_2$, (Me)N(SiH$_2$—CH$_2$—SiH$_2$(OEt))$_2$, (Et)N(SiH$_2$—CH$_2$—SiH$_2$(OEt))$_2$, (nPr)N(SiH$_2$—CH$_2$—SiH$_2$(OEt))$_2$, (iPr)N(SiH$_2$—CH$_2$—SiH$_2$(OEt))$_2$, (Bu)N(SiH$_2$—CH$_2$—SiH$_2$(OEt))$_2$, (iBu)N(SiH$_2$—CH$_2$—SiH$_2$(OEt))$_2$, (tBu)N(SiH$_2$—CH$_2$—SiH$_2$(OEt))$_2$, (amyl)N(SiH$_2$—CH$_2$—SiH$_2$(OEt))$_2$, (hexyl)N(SiH$_2$—CH$_2$—SiH$_2$(OEt))$_2$, HN(SiH$_2$—CH$_2$—SiH$_2$(Cl))(SiH$_2$—CH$_2$SiH$_3$), MeN(SiH$_2$—CH$_2$—SiH$_2$(Cl))(SiH$_2$—CH$_2$SiH$_3$), EtN(SiH$_2$—CH$_2$—SiH$_2$(Cl))(SiH$_2$—CH$_2$SiH$_3$), iPrN(SiH$_2$—CH$_2$—SiH$_2$(Cl))(SiH$_2$—CH$_2$SiH$_3$), (Cl)N(SiH$_2$—CH$_2$—SiH$_2$(Cl))(SiH$_2$—CH$_2$SiH$_3$), (Br)N(SiH$_2$—CH$_2$—SiH$_2$(Cl))(SiH$_2$—CH$_2$SiH$_3$), (I)N(SiH$_2$—CH$_2$—SiH$_2$(Cl))(SiH$_2$—CH$_2$SiH$_3$), HN(SiH$_2$—CH$_2$—SiH$_2$(Br))(SiH$_2$—CH$_2$SiH$_3$), MeN(SiH$_2$—CH$_2$—SiH$_2$(Br))(SiH$_2$—CH$_2$SiH$_3$), EtN(SiH$_2$—CH$_2$—SiH$_2$(Br))(SiH$_2$—CH$_2$SiH$_3$), iPrN(SiH$_2$—CH$_2$—SiH$_2$(Br))(SiH$_2$—CH$_2$SiH$_3$), (Cl)N(SiH$_2$—CH$_2$—SiH$_2$(Br))(SiH$_2$—CH$_2$SiH$_3$), (Br)N(SiH$_2$—CH$_2$—SiH$_2$(Br))(SiH$_2$—CH$_2$SiH$_3$), (I)N(SiH$_2$—CH$_2$—SiH$_2$(Br))(SiH$_2$—CH$_2$SiH$_3$), HN(SiH$_2$—CH$_2$—SiH$_2$(I))(SiH$_2$—CH$_2$SiH$_3$), MeN(SiH$_2$—CH$_2$—SiH$_2$(I))(SiH$_2$—CH$_2$SiH$_3$), EtN(SiH$_2$—CH$_2$—SiH$_2$(I))(SiH$_2$—CH$_2$SiH$_3$), iPrN(SiH$_2$—CH$_2$—SiH$_2$(I))(SiH$_2$—CH$_2$SiH$_3$), (Cl)N(SiH$_2$—CH$_2$—SiH$_2$(I))(SiH$_2$—CH$_2$SiH$_3$), (Br)N(SiH$_2$—CH$_2$—SiH$_2$(I))(SiH$_2$—CH$_2$SiH$_3$), (I)N(SiH$_2$—CH$_2$—SiH$_2$(I))(SiH$_2$—CH$_2$SiH$_3$), HN(SiH$_2$—CH$_2$—SiH$_2$(NH$_2$))(SiH$_2$—CH$_2$SiH$_3$), MeN(SiH$_2$—CH$_2$—SiH$_2$(NH$_2$))(SiH$_2$—CH$_2$SiH$_3$), EtN(SiH$_2$—CH$_2$—SiH$_2$(NH$_2$))(SiH$_2$—CH$_2$SiH$_3$), iPrN(SiH$_2$—CH$_2$—SiH$_2$(NH$_2$))(SiH$_2$—CH$_2$SiH$_3$), (Cl)N(SiH$_2$—CH$_2$—SiH$_2$(NH$_2$))(SiH$_2$—CH$_2$SiH$_3$), (Br)N(SiH$_2$—CH$_2$—SiH$_2$(NH$_2$))(SiH$_2$—CH$_2$SiH$_3$), (I)N(SiH$_2$—CH$_2$—SiH$_2$(NH$_2$))(SiH$_2$—CH$_2$SiH$_3$), HN(SiH$_2$—CH$_2$—SiH$_2$(NMe$_2$))(SiH$_2$—CH$_2$SiH$_3$), MeN(SiH$_2$—CH$_2$—SiH$_2$(NMe$_2$))(SiH$_2$—CH$_2$SiH$_3$), EtN(SiH$_2$—CH$_2$—SiH$_2$(NMe$_2$))(SiH$_2$—CH$_2$SiH$_3$), iPrN(SiH$_2$—CH$_2$—SiH$_2$(NMe$_2$))(SiH$_2$—CH$_2$SiH$_3$), Cl)N(SiH$_2$—CH$_2$—SiH$_2$(NMe$_2$))(SiH$_2$—CH$_2$SiH$_3$), (Br)N(SiH$_2$—CH$_2$—SiH$_2$(NMe$_2$))(SiH$_2$—CH$_2$SiH$_3$), (I)N(SiH$_2$—CH$_2$—SiH$_2$(NMe$_2$))(SiH$_2$—CH$_2$SiH$_3$), HN(SiH$_2$—CH$_2$—SiH$_2$(OMe))(SiH$_2$—CH$_2$SiH$_3$), MeN(SiH$_2$—CH$_2$—SiH$_2$(OMe))(SiH$_2$—CH$_2$SiH$_3$), EtN(SiH$_2$—CH$_2$—SiH$_2$(OMe))(SiH$_2$—CH$_2$SiH$_3$), iPrN(SiH$_2$—CH$_2$—SiH$_2$(OMe))(SiH$_2$—CH$_2$SiH$_3$), (Cl)N(SiH$_2$—CH$_2$—SiH$_2$(OMe))(SiH$_2$—CH$_2$SiH$_3$), (Br)N(SiH$_2$—CH$_2$—SiH$_2$(OMe))(SiH$_2$—CH$_2$SiH$_3$), (I)N(SiH$_2$—CH$_2$—SiH$_2$(OMe))(SiH$_2$—CH$_2$SiH$_3$), HN(SiH$_2$—CH$_2$—SiH$_2$(OEt))(SiH$_2$—CH$_2$SiH$_3$), MeN(SiH$_2$—CH$_2$—SiH$_2$(OEt))(SiH$_2$—CH$_2$SiH$_3$), EtN(SiH$_2$—CH$_2$—SiH$_2$(OEt))(SiH$_2$—CH$_2$SiH$_3$), iPrN(SiH$_2$—CH$_2$—SiH$_2$(OEt))(SiH$_2$—CH$_2$SiH$_3$), (Cl)N(SiH$_2$—CH$_2$—SiH$_2$(OEt))(SiH$_2$—CH$_2$SiH$_3$), (Br)N(SiH$_2$—CH$_2$—SiH$_2$(OEt))(SiH$_2$—CH$_2$SiH$_3$), and (I)N(SiH$_2$—CH$_2$—SiH$_2$(OEt))(SiH$_2$—CH$_2$SiH$_3$).

8. The Si-containing film forming composition of claim 6, wherein the carbosilane substituted amine precursor selected from the group consisting of (Cl)N(SiH$_2$—CH$_2$SiH$_3$)$_2$, (Br)N(SiH$_2$—CH$_2$SiH$_3$)$_2$, (I)N(SiH$_2$—CH$_2$SiH$_3$)$_2$, (H)N(SiH$_2$—CH$_2$SiH$_3$)$_2$, (Me)N(SiH$_2$—CH$_2$SiH$_3$)$_2$, (Et)N(SiH$_2$—CH$_2$SiH$_3$)$_2$, (nPr)N(SiH$_2$—CH$_2$SiH$_3$)$_2$, (iPr)N(SiH$_2$—CH$_2$SiH$_3$)$_2$, (Bu)N(SiH$_2$—CH$_2$SiH$_3$)$_2$, (iBu)N(SiH$_2$—CH$_2$SiH$_3$)$_2$, (tBu)N(SiH$_2$—CH$_2$SiH$_3$)$_2$, (amyl)N(SiH$_2$—CH$_2$SiH$_3$)$_2$, (hexyl)N(SiH$_2$—CH$_2$SiH$_3$)$_2$, (Me)N(Si(H)(Cl)—CH$_2$—SiH$_3$)$_2$, (Et)N(Si(H)(Cl)—CH$_2$—SiH$_3$)$_2$, (nPr)N(Si(H)(Cl)—CH$_2$—SiH$_3$)$_2$, (iPr)N(Si(H)(Cl)—CH$_2$—SiH$_3$)$_2$, (Bu)N(Si(H)(Cl)—CH$_2$—SiH$_3$)$_2$, (iBu)N(Si(H)(Cl)—CH$_2$—SiH$_3$)$_2$, (tBu)N(Si(H)(Cl)—CH$_2$—SiH$_3$)$_2$, (amyl)N(Si(H)(Cl)—CH$_2$—SiH$_3$)$_2$, (hexyl)N(Si(H)(Cl)—CH$_2$—SiH$_3$)$_2$, (Me)N(Si(H)(Br)—CH$_2$—SiH$_3$)$_2$, (Et)N(Si(H)(Br)—CH$_2$—SiH$_3$)$_2$, (nPr)N(Si(H)(Br)—CH$_2$—SiH$_3$)$_2$, (iPr)N(Si(H)(Br)—CH$_2$—SiH$_3$)$_2$, (Bu)N(Si(H)(Br)—CH$_2$—SiH$_3$)$_2$, (iBu)N(Si(H)(Br)—CH$_2$—SiH$_3$)$_2$, (tBu)N(Si(H)(Br)—CH$_2$—SiH$_3$)$_2$, (amyl)N(Si(H)(Br)—CH$_2$—SiH$_3$)$_2$, (hexyl)N(Si(H)(Br)—CH$_2$—SiH$_3$)$_2$, (Me)N(Si(H)(I)—CH$_2$—SiH$_3$)$_2$, (Et)N(Si(H)(I)—CH$_2$—SiH$_3$)$_2$, (nPr)N(Si(H)(I)—CH$_2$—SiH$_3$)$_2$, (iPr)N(Si(H)(I)—CH$_2$—SiH$_3$)$_2$, (Bu)N(Si(H)(I)—CH$_2$—SiH$_3$)$_2$, (iBu)N(Si(H)(I)—CH$_2$—SiH$_3$)$_2$, (tBu)N(Si(H)(I)—CH$_2$—SiH$_3$)$_2$, (amyl)N(Si(H)(I)—CH$_2$—SiH$_3$)$_2$, (hexyl)N(Si(H)(I)—CH$_2$—SiH$_3$)$_2$, (Me)N(Si(H)(NH$_2$)—CH$_2$—SiH$_3$)$_2$, (Et)N(Si(H)(NH$_2$)—CH$_2$—SiH$_3$)$_2$, (nPr)N(Si(H)(NH$_2$)—CH$_2$—SiH$_3$)$_2$, (iPr)N(Si(H)(NH$_2$)—CH$_2$—SiH$_3$)$_2$, (Bu)N(Si(H)(NH$_2$)—CH$_2$—SiH$_3$)$_2$, (iBu)N(Si(H)(NH$_2$)—CH$_2$—SiH$_3$)$_2$, (tBu)N(Si(H)(NH$_2$)—CH$_2$—SiH$_3$)$_2$, (amyl)N(Si(H)(NH$_2$)—CH$_2$—SiH$_3$)$_2$, (hexyl)N(Si(H)(NH$_2$)—CH$_2$—SiH$_3$)$_2$, (Me)N(Si(H)(NMe$_2$)-CH$_2$—SiH$_3$)$_2$, (Et)N(Si(H)(NMe$_2$)-CH$_2$—SiH$_3$)$_2$, (nPr)N(Si(H)(NMe$_2$)-CH$_2$—SiH$_3$)$_2$, (iPr)N(Si(H)(NMe$_2$)-CH$_2$—SiH$_3$)$_2$, (Bu)N(Si(H)(NMe$_2$)-CH$_2$—SiH$_3$)$_2$, (iBu)N(Si(H)(NMe$_2$)-CH$_2$—SiH$_3$)$_2$, (tBu)N(Si(H)(NMe$_2$)-CH$_2$—SiH$_3$)$_2$, (amyl)N(Si(H)(NMe$_2$)-CH$_2$—SiH$_3$)$_2$, (hexyl)N(Si(H)(NMe$_2$)-CH$_2$—SiH$_3$)$_2$, (Me)N(Si(H)(NMeEt)-CH$_2$—SiH$_3$)$_2$, (Et)N(Si(H)(NMeEt)-CH$_2$—SiH$_3$)$_2$, (nPr)N(Si(H)(NMeEt)-CH$_2$—SiH$_3$)$_2$, (iPr)N(Si(H)(NMeEt)-CH$_2$—

SiH$_3$)$_2$, (Bu)N(Si(H)(NMeEt)-CH$_2$—SiH$_3$)$_2$, (iBu)N(Si(H)(NMeEt)-CH$_2$—SiH$_3$)$_2$, (tBu)N(Si(H)(NMeEt)-CH$_2$—SiH$_3$)$_2$, (amyl)N(Si(H)(NMeEt)-CH$_2$—SiH$_3$)$_2$, (hexyl)N(Si(H)(NMeEt)-CH$_2$—SiH$_3$)$_2$, (Me)N(Si(H)(NMeH)—CH$_2$—SiH$_3$)$_2$, (Et)N(Si(H)(NMeH)—CH$_2$—SiH$_3$)$_2$, (nPr)N(Si(H)(NMeH)—CH$_2$—SiH$_3$)$_2$, (iPr)N(Si(H)(NMeH)—CH$_2$—SiH$_3$)$_2$, (Bu)N(Si(H)(NMeH)—CH$_2$—SiH$_3$)$_2$, (iBu)N(Si(H)(NMeH)—CH$_2$—SiH$_3$)$_2$, (tBu)N(Si(H)(NMeH)—CH$_2$—SiH$_3$)$_2$, (amyl)N(Si(H)(NMeH)—CH$_2$—SiH$_3$)$_2$, (hexyl)N(Si(H)(NMeH)—CH$_2$—SiH$_3$)$_2$, (Me)N(Si(H)(NEtH)—CH$_2$—SiH$_3$)$_2$, (Et)N(Si(H)(NEtH)—CH$_2$—SiH$_3$)$_2$, (nPr)N(Si(H)(NEtH)—CH$_2$—SiH$_3$)$_2$, (iPr)N(Si(H)(NEtH)—CH$_2$—SiH$_3$)$_2$, (Bu)N(Si(H)(NEtH)—CH$_2$—SiH$_3$)$_2$, (iBu)N(Si(H)(NEtH)—CH$_2$—SiH$_3$)$_2$, (tBu)N(Si(H)(NEtH)—CH$_2$—SiH$_3$)$_2$, (amyl)N(Si(H)(NEtH)—CH$_2$—SiH$_3$)$_2$, (hexyl)N(Si(H)(NEtH)—CH$_2$—SiH$_3$)$_2$, (Me)N(Si(H)(NiPrH)—CH$_2$—SiH$_3$)$_2$, (Et)N(Si(H)(NiPrH)—CH$_2$—SiH$_3$)$_2$, (nPr)N(Si(H)(NiPrH)—CH$_2$—SiH$_3$)$_2$, (iPr)N(Si(H)(NiPrH)—CH$_2$—SiH$_3$)$_2$, (Bu)N(Si(H)(NiPrH)—CH$_2$—SiH$_3$)$_2$, (iBu)N(Si(H)(NiPrH)—CH$_2$—SiH$_3$)$_2$, (tBu)N(Si(H)(NiPrH)—CH$_2$—SiH$_3$)$_2$, (amyl)N(Si(H)(NiPrH)—CH$_2$—SiH$_3$)$_2$, (hexyl)N(Si(H)(NiPrH)—CH$_2$—SiH$_3$)$_2$, (Me)N(Si(H)(NtBuH)—CH$_2$—SiH$_3$)$_2$, (Et)N(Si(H)(NtBuH)—CH$_2$—SiH$_3$)$_2$, (nPr)N(Si(H)(NtBuH)—CH$_2$—SiH$_3$)$_2$, (iPr)N(Si(H)(NtBuH)—CH$_2$—SiH$_3$)$_2$, (Bu)N(Si(H)(NtBuH)—CH$_2$—SiH$_3$)$_2$, (iBu)N(Si(H)(NtBuH)—CH$_2$—SiH$_3$)$_2$, (tBu)N(Si(H)(NtBuH)—CH$_2$—SiH$_3$)$_2$, (amyl)N(Si(H)(NtBuH)—CH$_2$—SiH$_3$)$_2$, (hexyl)N(Si(H)(NtBuH)—CH$_2$—SiH$_3$)$_2$, (Me)N(Si(H)(OEt)-CH$_2$—SiH$_3$)$_2$, (Et)N(Si(H)(OEt)-CH$_2$—SiH$_3$)$_2$, (nPr)N(Si(H)(OEt)-CH$_2$—SiH$_3$)$_2$, (iPr)N(Si(H)(OEt)-CH$_2$—SiH$_3$)$_2$, (Bu)N(Si(H)(OEt)-CH$_2$—SiH$_3$)$_2$, (iBu)N(Si(H)(OEt)-CH$_2$—SiH$_3$)$_2$, (tBu)N(Si(H)(OEt)-CH$_2$—SiH$_3$)$_2$, (amyl)N(Si(H)(OEt)-CH$_2$—SiH$_3$)$_2$, (hexyl)N(Si(H)(OEt)-CH$_2$—SiH$_3$)$_2$, HN(Si(H)(Cl)—CH$_2$—SiH$_3$)(SiH$_2$—CH$_2$SiH$_3$), MeN(Si(H)(Cl)—CH$_2$—SiH$_3$)(SiH$_2$—CH$_2$SiH$_3$), EtN(Si(H)(Cl)—CH$_2$—SiH$_3$)(SiH$_2$—CH$_2$SiH$_3$), iPrN(Si(H)(Cl)—CH$_2$—SiH$_3$)(SiH$_2$—CH$_2$SiH$_3$), (Cl)N(Si(H)(Cl)—CH$_2$—SiH$_3$)(SiH$_2$—CH$_2$SiH$_3$), (Br)N(Si(H)(Cl)—CH$_2$—SiH$_3$)(SiH$_2$—CH$_2$SiH$_3$), (I)N(Si(H)(Cl)—CH$_2$—SiH$_3$)(SiH$_2$—CH$_2$SiH$_3$), HN(Si(H)(Br)—CH$_2$—SiH$_3$)(SiH$_2$—CH$_2$SiH$_3$), MeN(Si(H)(Br)—CH$_2$—SiH$_3$)(SiH$_2$—CH$_2$SiH$_3$), EtN(Si(H)(Br)—CH$_2$—SiH$_3$)(SiH$_2$—CH$_2$SiH$_3$), iPrN(Si(H)(Br)—CH$_2$—SiH$_3$)(SiH$_2$—CH$_2$SiH$_3$), (Cl)N(Si(H)(Br)—CH$_2$—SiH$_3$)(SiH$_2$—CH$_2$SiH$_3$), (Br)N(Si(H)(Br)—CH$_2$—SiH$_3$)(SiH$_2$—CH$_2$SiH$_3$), (I)N(Si(H)(Br)—CH$_2$—SiH$_3$)(SiH$_2$—CH$_2$SiH$_3$), HN(Si(H)(I)—CH$_2$—SiH$_3$)(SiH$_2$—CH$_2$SiH$_3$), MeN(Si(H)(I)—CH$_2$—SiH$_3$)(SiH$_2$—CH$_2$SiH$_3$), EtN(Si(H)(I)—CH$_2$—SiH$_3$)(SiH$_2$—CH$_2$SiH$_3$), iPrN(Si(H)(I)—CH$_2$—SiH$_3$)(SiH$_2$—CH$_2$SiH$_3$), (Cl)N(Si(H)(I)—CH$_2$—SiH$_3$)(SiH$_2$—CH$_2$SiH$_3$), (Br)N(Si(H)(I)—CH$_2$—SiH$_3$)(SiH$_2$—CH$_2$SiH$_3$), (I)N(Si(H)(I)—CH$_2$—SiH$_3$)(SiH$_2$—CH$_2$SiH$_3$), HN(Si(H)(NH$_2$)—CH$_2$—SiH$_3$)(SiH$_2$—CH$_2$SiH$_3$), MeN(Si(H)(NH$_2$)—CH$_2$—SiH$_3$)(SiH$_2$—CH$_2$SiH$_3$), EtN(Si(H)(NH$_2$)—CH$_2$—SiH$_3$)(SiH$_2$—CH$_2$SiH$_3$), iPrN(Si(H)(NH$_2$)—CH$_2$—SiH$_3$)(SiH$_2$—CH$_2$SiH$_3$), (Cl)N(Si(H)(NH$_2$)—CH$_2$—SiH$_3$)(SiH$_2$—CH$_2$SiH$_3$), (Br)N(Si(H)(NH$_2$)—CH$_2$—SiH$_3$)(SiH$_2$—CH$_2$SiH$_3$), (I)N(Si(H)(NH$_2$)—CH$_2$—SiH$_3$)(SiH$_2$—CH$_2$SiH$_3$), HN(Si(H)(NMe$_2$)-CH$_2$—SiH$_3$)(SiH$_2$—CH$_2$SiH$_3$), MeN(Si(H)(NMe$_2$)-CH$_2$—SiH$_3$)(SiH$_2$—CH$_2$SiH$_3$), tN(Si(H)(NMe$_2$)-CH$_2$—SiH$_3$)(SiH$_2$—CH$_2$SiH$_3$), iPrN(Si(H)(NMe$_2$)-CH$_2$—SiH$_3$)(SiH$_2$—CH$_2$SiH$_3$), (Cl)N(Si(H)(NMe$_2$)-CH$_2$—SiH$_3$)(SiH$_2$—CH$_2$SiH$_3$), (Br)N(Si(H)(NMe$_2$)-CH$_2$—SiH$_3$)(SiH$_2$—CH$_2$SiH$_3$), (I)N(Si(H)(NMe$_2$)-CH$_2$—SiH$_3$)(SiH$_2$—CH$_2$SiH$_3$), HN(Si(H)(OMe)-CH$_2$—SiH$_3$)(SiH$_2$—CH$_2$SiH$_3$), MeN(Si(H)(OMe)-CH$_2$—SiH$_3$)(SiH$_2$—CH$_2$SiH$_3$), EtN(Si(H)(OMe)-CH$_2$—SiH$_3$)(SiH$_2$—CH$_2$SiH$_3$), iPrN(Si(H)(OMe)-CH$_2$—SiH$_3$)(SiH$_2$—CH$_2$SiH$_3$), Cl)N(Si(H)(OMe)-CH$_2$—SiH$_3$)(SiH$_2$—CH$_2$SiH$_3$), (Br)N(Si(H)(OMe)-CH$_2$—SiH$_3$)(SiH$_2$—CH$_2$SiH$_3$), (I)N(Si(H)(OMe)-CH$_2$—SiH$_3$)(SiH$_2$—CH$_2$SiH$_3$), HN(Si(H)(OEt)-CH$_2$—SiH$_3$)(SiH$_2$—CH$_2$SiH$_3$), MeN(Si(H)(OEt)-CH$_2$—SiH$_3$)(SiH$_2$—CH$_2$SiH$_3$), EtN(Si(H)(OEt)-CH$_2$—SiH$_3$)(SiH$_2$—CH$_2$SiH$_3$), iPrN(Si(H)(OEt)-CH$_2$—SiH$_3$)(SiH$_2$—CH$_2$SiH$_3$), (Cl)N(Si(H)(OEt)-CH$_2$—SiH$_3$)(SiH$_2$—CH$_2$SiH$_3$), (Br)N(Si(H)(OEt)-CH$_2$—SiH$_3$)(SiH$_2$—CH$_2$SiH$_3$), and (I)N(Si(H)(OEt)-CH$_2$—SiH$_3$)(SiH$_2$—CH$_2$SiH$_3$).

9. The Si-containing film forming composition of claim 6, wherein the carbosilane substituted amine precursor is selected from the group consisting of HN(SiH$_2$—CH$_2$—SiH$_3$)$_2$, (Me)N(SiH$_2$—CH$_2$—SiH$_3$)$_2$, (Et)N(SiH$_2$—CH$_2$—SiH$_3$)$_2$, (nPr)N(SiH$_2$—CH$_2$—SiH$_3$)$_2$, (iPr)N(SiH$_2$—CH$_2$—SiH$_3$)$_2$, (Bu)N(SiH$_2$—CH$_2$—SiH$_3$)$_2$, (iBu)N(SiH$_2$—CH$_2$—SiH$_3$)$_2$, (tBu)N(SiH$_2$—CH$_2$—SiH$_3$)$_2$, (amyl)N(SiH$_2$—CH$_2$—SiH$_3$)$_2$, (hexyl)N(SiH$_2$—CH$_2$—SiH$_3$)$_2$, (Br)N(SiH$_2$—CH$_2$—SiH$_3$)$_2$, (Cl)N(SiH$_2$—CH$_2$—SiH$_3$)$_2$, and (I)N(SiH$_2$—CH$_2$—SiH$_3$)$_2$.

10. A method of deposition a Si-containing layer on a substrate, the method comprising:
introducing a vapor of the Si-containing film forming composition of claim 1 into a reactor having a substrate disposed therein; and
depositing at least part of the carbosilane substituted amine precursor onto the substrate to form a Si-containing layer using a vapor deposition method.

11. The method of claim 10, further comprising introducing a co-reactant into the reactor.

12. The method of claim 10, wherein the vapor deposition process is a chemical vapor deposition process.

13. The method of claim 10, wherein the vapor deposition process is an atomic layer deposition (ALD) process.

14. A method of forming a Si-containing film on a substrate, the method comprising forming a solution comprising the Si-containing film forming composition of claim 1; and contacting the solution with the substrate via a spin coating, spray coating, dip coating, or slit coating technique to form the Si-containing film.

15. The method of claim 10, wherein the Si-containing film forming composition comprises a carbosilane substituted amine precursor having the formula N(—SiHR$^2$—CH$_2$—SiH$_2$R$^3$)$_3$.

16. The method of claim 15, wherein the Si-containing film forming composition comprises a carbosilane substituted amine precursor having the formula N(—SiH$_2$—CH$_2$—SiH$_3$)$_3$.

17. The method of claim 10, wherein the Si-containing film forming composition comprises a carbosilane substituted amine precursor having the formula R$^1$N(—SiHR$^2$—CH$_2$—SiH$_2$R$^3$)$_2$.

18. The method of claim 17, wherein the Si-containing film forming composition comprises a carbosilane substituted amine precursor having the formula HN(SiH$_2$—CH$_2$—SiH$_3$)$_2$.

19. The method of claim 14, wherein the Si-containing film forming composition comprises a carbosilane substituted amine precursor having the formula N(—SiHR$^2$—CH$_2$—SiH$_2$R$^3$)$_3$.

20. The method of claim 19, wherein the Si-containing film forming composition comprises a carbosilane substituted amine precursor having the formula N(SiH$_2$—CH$_2$SiH$_3$)$_3$.

* * * * *